US007001763B1

(12) United States Patent
Walke et al.

(10) Patent No.: US 7,001,763 B1
(45) Date of Patent: Feb. 21, 2006

(54) HUMAN SEMAPHORIN PROTEINS AND POLYNUCLEOTIDES ENCODING THE SAME

(75) Inventors: D. Wade Walke, Spring, TX (US); John Scoville, Houston, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 524 days.

(21) Appl. No.: 09/981,318

(22) Filed: Oct. 17, 2001

Related U.S. Application Data

(60) Provisional application No. 60/241,194, filed on Oct. 17, 2000.

(51) Int. Cl.
   *C12N 15/63* (2006.01)
   *C12N 5/10* (2006.01)
   *C07H 21/04* (2006.01)

(52) U.S. Cl. .................. 435/320.1; 435/325; 536/23.5

(58) Field of Classification Search ............. 435/320.1, 435/325; 536/23.5
   See application file for complete search history.

(56) References Cited

U.S. PATENT DOCUMENTS

| | | | |
|---|---|---|---|
| 4,215,051 | A | 7/1980 | Schroeder et al. |
| 4,376,110 | A | 3/1983 | David et al. |
| 4,594,595 | A | 6/1986 | Struckman |
| 4,631,211 | A | 12/1986 | Houghten |
| 4,689,405 | A | 8/1987 | Frank et al. |
| 4,713,326 | A | 12/1987 | Dattagupta et al. |
| 4,873,191 | A | 10/1989 | Wagner et al. |
| 4,946,778 | A | 8/1990 | Ladner et al. |
| 5,252,743 | A | 10/1993 | Barrett et al. |
| 5,272,057 | A | 12/1993 | Smulson et al. |
| 5,424,186 | A | 6/1995 | Fodor et al. |
| 5,445,934 | A | 8/1995 | Fodor et al. |
| 5,459,127 | A | 10/1995 | Felgner et al. |
| 5,556,752 | A | 9/1996 | Lockhart et al. |
| 5,700,637 | A | 12/1997 | Southern |
| 5,744,305 | A | 4/1998 | Fodor et al. |
| 5,830,721 | A | 11/1998 | Stemmer et al. |
| 5,837,458 | A | 11/1998 | Minshull et al. |
| 5,869,336 | A | 2/1999 | Meyer et al. |
| 5,877,397 | A | 3/1999 | Lonberg et al. |
| 5,948,767 | A | 9/1999 | Scheule et al. |
| 6,075,181 | A | 6/2000 | Kucherlapati et al. |
| 6,110,490 | A | 8/2000 | Thierry |
| 6,136,566 | A | 10/2000 | Sands et al. |
| 6,139,833 | A | 10/2000 | Burgess |
| 6,150,584 | A | 11/2000 | Kucherlapati et al. |
| 6,207,371 | B1 | 3/2001 | Zambrowicz et al. |
| 2003/0073129 | A1 * | 4/2003 | Baker et al. .................. 435/7.1 |

OTHER PUBLICATIONS

Püschel et al. *Neuron*, vol. 14, pp. 941-948, 1995.*
Tessier-Lavigne et al, *Science*, vol. 274, pp. 1123-1133, 1996.*
Bird et al, 1988, "Single-Chain Antigen-Binding Proteins", Science 242:423-426.
Bitter et al, 1987, "Expression and Secretion Vectors for Yeast", Methods in Enzymology 153:516-544.
Colbere-Garapin et al, 1981, "A New Dominant Hybrid Selective Marker for Higher Eukaryotic Cells", J. Mol. Biol. 150:1-14.
Gautier et al, 1987, "α-DNA IV:α-anomeric and β-anomeric tetrathymidylates covalently linked to intercalating oxazolopyridocarbazole. Synthesis, physiochemical properties and poly (rA) binding", Nucleic Acids Research 15(16): 6625-6641.
Gordon, 1989, "Transgenic Animals", International Review of Cytology, 115:171-229.
Greenspan et al, 1993, "Idiotypes: structure and immunogenicity", FASEB Journal 7:437-444.
Gu et al, 1994, "Deletion of a DNA Polymerase β Gene Segment in T Cells Using Cell Type-Specific Gene Targeting", Science 265:103-106.
Huse et al, 1989, "Generation of a Large Combinatorial Library of the Immunoglobulin Repertoire in Phage Lambda", Science 246:1275-1281.
Huston et al, 1988, "Protein engineering of antibody binding sites: Recovery of specific activity in an anti-digoxin single-chain Fv analogue produced in *Escherichia coli*", Proc. Natl. Acad. Sci. USA 85:5879-5883.
Inoue et al, 1987, "Sequence-dependent hydrolysis of RNA using modified oligonucleotide splints and R Nase H", FEBS Letters 215(2):327-330.
Inoue et al, 1987, "Synthesis and hybridization studies on two complementary nona(2'-O-methyl)ribonucleotides", Nucleic Acids Research 15(15):6131-6149.
Inouye & Inouye, 1985, "Up-promoter mutations in the lpp gene of *Escherichia coli*", Nucleic Acids Research 13(9): 3101-3110.
Janknecht et al, 1991, "Rapid and efficient purification of native histidine-tagged protein expressed by recombinant vaccinia virus", PNAS 88:8972-8976.
Kohler & Milstein, 1975, "Continuous cultures of fused cells secreting antibody of predefined specificity", Nature 256:495-497.
Lakso et al, 1992, "Targeted oncogene activation by site-specific recombination in transgenic mice", Proc. Natl. Acad. Sci. USA 89:6232-6236.

(Continued)

*Primary Examiner*—Janet L. Andres
*Assistant Examiner*—Stephen Gucker

(57) ABSTRACT

Novel human polynucleotide and polypeptide sequences are disclosed that can be used in therapeutic, diagnostic, and pharmacogenomic applications.

8 Claims, No Drawings

OTHER PUBLICATIONS

Lavitrano et al, 1989, "Sperm Cells as Vectors for Introducing Foreign DNA into Eggs: Genetic Transformation of Mice", Cell 57:717-723.

Lo, 1983, "Transformation by Iontophoretic Microinjection of DNA: Multiple Integrations without Tandem Insertions", Mol. & Cell. Biology 3(10):1803-1814.

Logan et al, 1984, "Adenovirus tripartite leader sequence enhances translation of mRNAs late after infection", Proc. Natl. Acad. Sci. USA 81:3655-3659.

Lowy et al, 1980, "Isolation of Trasforming DNA: Cloning the Hamster aprt Gene", Cell 22:817-823.

Morrison et al, 1984, "Chimeric human antibody molecules: Mouse antigen-binding domains with human constant region domains", Proc. Natl. Acad. Sci. USA 81:6851-6855.

Mulligan & Berg, 1981, "Selection for animal cells that express the *Escherichia coli* gene coding for xanthine-guanine phosphoribosyltransferase", Proc. Natl. Acad. Sci. USA 78(4):2072-2076.

Nueberger et al, 1984, "Recombinant antibodies possessing novel effector functions", Nature 312:604-608.

Nisonoff, 1991, "Idiotypes: Concepts and Applications", J. of Immunology 147:2429-2438.

O'Hare et al, "Transformation of mouse fibroblasts to methotrexate resistance by a recombinant plasmid expressing a prokaryotic dihydrofolate reductase", Proc. Natl. Acad. Sci. USA 78(3): 1527-1531.

Ruther et al, 1983, "Easy identification of cDNA clones", EMBO Journal 2(10):1791-1794.

Santerre et al, 1984, "Expression of prokaryotic genes for hygromycin B and G418 resistance as dominant-selection markers in mouse L cells", Gene 30:147-156.

Sarin et al, 1988, "Inhibition of acquired immunodeficiency syndrome virus by oligodeoxynucleoside methylphosphonates", Proc. Natl. Acad. Sci. USA 85:7448-7451.

Smith et al, 1983, "Molecular Engineering of the Autographa california Nuclear Polyhedrosis Virus Genome: Deletion Mutations within the Polyhedrin Gene", J. Virol. 46(2):584-593.

Stein et al, "Physiochemical properties of phosphorothioate oligodeoxynucleotides", Nucleic Acids Research 16(8): 3209-3221.

Szybalska & Szybalski, 1962, "Genetics of Human Cell Lines, IV. DNA-Mediated Heritable Transformation of a Biochemical Trait", Proc. Natl. Acad. Sci. USA 48:2026-2034.

Takeda et al, 1985, "Construction of chimaeric processed immunoglobulin genes containing mouse variable and human constant region sequences", Nature 314:452-454.

Thompson et al, 1989, "Germ Line Transmission and Expression of a Corrected HPRT Gene Produced by Gene Targeting in Embryonic Stem Cells", Cell 56:313-321.

Van Der Putten et al, 1985, "Efficient insertion of genes into the mouse germ line via retroviral vectors", Proc. Natl. Acad. Sci. USA 82:6148-6152.

Van Heeke et al, 1989, "Expression of Human Asparagine Synthetase in *Escherichia coli*", J. Biol. Chemistry 264(10): 5503-5509.

Ward et al, 1989, "Binding activities of a repertoire of single immunoglobulin variable domains secreted from *Escherichia coli*", Nature 341:544-546.

Wigler et al, 1977, "Transfer of Purified Herpes Virus Thymidine Kinase Gene to Cultured Mouse Cells", Cell 11:223-232.

Wigler et al, 1980, "Transformation of mammalian cells with an amplifiable dominant-acting gene", Proc. Natl. Acad. Sci. USA 77(6):3567-3570.

* cited by examiner

SEQUENCE LISTING

<160> NUMBER OF SEQ ID NOS: 35

<210> SEQ ID NO 1
<211> LENGTH: 2304
<212> TYPE: DNA
<213> ORGANISM: homo sapiens

<400> SEQUENCE: 1

| | | | | | |
|---|---|---|---|---|---|
| atgcccagcc | agggcagggt | ggagagctgc | agctgcaggt | ccggaggcgg | gggcccccgg | 60 |
| ggcgactcgg | gggcggaccg | cggggcggag | ctgccgcccg | tgagtccggc | cgagccacct | 120 |
| gagcccgagc | cgcgggacac | cgtcgctcct | gctctccgaa | tgctgcgcac | cgcgatgggc | 180 |
| ctgaggagct | ggctcgccgc | cccatggggc | gcgctgccgc | ctcggccacc | gctgctgctg | 240 |
| ctcctgctgc | tgctgctcct | gctgcagccg | ccgcctccga | cctgggcgct | cagccccgg | 300 |
| atcagcctgc | ctctgggctc | tgaagagcgg | ccattcctca | gattcgaagc | tgaacacatc | 360 |
| tccaactaca | cagcccttct | gctgagcagg | gatggcagga | ccctgtacgt | gggtgctcga | 420 |
| gaggccctct | ttgcactcag | tagcaacctc | agcttcctgc | caggcgggga | gtaccaggag | 480 |
| ctgctttggg | gtgcagacgc | agagaagaaa | cagcagtgca | gcttcaaggg | caaggaccca | 540 |
| cagcgcgact | gtcaaaacta | catcaagatc | ctcctgccgc | tcagcggcag | tcacctgttc | 600 |
| acctgtggca | cagcagcctt | cagcccccatg | tgtacctaca | tcaacatgga | gaacttcacc | 660 |
| ctggcaaggg | acgagaaggg | gaatgtcctc | ctggaagatg | gcaagggccg | ttgtcccttc | 720 |
| gacccgaatt | tcaagtccac | tgccctggtg | gttgatggcg | agctctacac | tggaacagtc | 780 |
| agcagcttcc | aagggaatga | cccggccatc | tcgcggagcc | aaagccttcg | ccccaccaag | 840 |
| accgagagct | ccctcaactg | gctgcaagac | ccagcttttg | tggcctcagc | ctacattcct | 900 |
| gagagcctgg | gcagcttgca | aggcgatgat | gacaagatct | acttttttctt | cagcgagact | 960 |
| ggccaggaat | ttgagttctt | tgagaacacc | attgtgtccc | gcattgcccg | catctgcaag | 1020 |
| ggcgatgagg | gtggagagcg | ggtgctacag | cagcgctgga | cctccttcct | caaggcccag | 1080 |
| ctgctgtgct | cacggcccga | cgatggcttc | cccttcaacg | tgctgcagga | tgtcttcacg | 1140 |
| ctgagcccca | gcccccagga | ctggcgtgac | acccttttct | atgggggtctt | cacttcccag | 1200 |
| tggcacaggg | gaactacaga | aggctctgcc | gtctgtgtct | tcacaatgaa | ggatgtgcag | 1260 |
| agagtcttca | gcggcctcta | caaggaggtg | aaccgtgaga | cacagcagtg | gtacaccgtg | 1320 |
| acccacccgg | tgcccacacc | ccggcctgga | gcgtgcatca | ccaacagtgc | ccgggaaagg | 1380 |
| aagatcaact | catccctgca | gctcccagac | cgcgtgctga | acttcctcaa | ggaccacttc | 1440 |
| ctgatggacg | ggcaggtccg | aagccgcatg | ctgctgctgc | agcccaggc | tcgctaccag | 1500 |
| cgcgtggctg | tacaccgcgt | ccctggcctg | caccacacct | acgatgtcct | cttcctgggc | 1560 |

```
actggtgacg gccggctcca caaggcagtg agcgtgggcc cccgggtgca catcattgag    1620
gagctgcaga tcttctcatc gggacagccc gtgcagaatc tgctcctgga cacccacagg    1680
gggctgctgt atgcggcctc acactcgggc gtagtccagg tgcccatggc caactgcagc    1740
ctgtacagga gctgtgggga ctgcctcctc gcccgggacc cctactgtgc ttggagcggc    1800
tccagctgca agcacgtcag cctctaccag cctcagctgg ccaccaggcc gtggatccag    1860
gacatcgagg gagccagcgc caaggacctt tgcagcgcgt cttcggttgt gtccccgtct    1920
tttgtaccaa caggggagaa gccatgtgag caagtccagt tccagcccaa cacagtgaac    1980
actttggcct gcccgctcct ctccaacctg gcgacccgac tctggctacg caacggggcc    2040
cccgtcaatg cctcggcctc ctgccacgtg ctacccactg gggacctgct gctggtgggc    2100
acccaacagc tgggggagtt ccagtgctgg tcactagagg agggcttcca gcagctggta    2160
gccagctact gcccagaggt ggtggaggac ggggtggcag accaaacaga tgagggtggc    2220
agtgtacccg tcattatcag cacatcgcgt gtgagtgcac ccagcacccg gctggggcct    2280
gtccctggat gcaggctact ctag                                           2304
```

<210> SEQ ID NO 2
<211> LENGTH: 767
<212> TYPE: PRT
<213> ORGANISM: homo sapiens

<400> SEQUENCE: 2

```
Met Pro Ser Gln Gly Arg Val Glu Ser Cys Ser Cys Arg Ser Gly Gly
 1               5                  10                  15

Gly Gly Pro Arg Gly Asp Ser Gly Ala Asp Arg Gly Ala Glu Leu Pro
            20                  25                  30

Pro Val Ser Pro Ala Glu Pro Glu Pro Glu Pro Arg Asp Thr Val
        35                  40                  45

Ala Pro Ala Leu Arg Met Leu Arg Thr Ala Met Gly Leu Arg Ser Trp
    50                  55                  60

Leu Ala Ala Pro Trp Gly Ala Leu Pro Pro Arg Pro Pro Leu Leu Leu
65                  70                  75                  80

Leu Leu Leu Leu Leu Leu Leu Gln Pro Pro Pro Thr Trp Ala
                85                  90                  95

Leu Ser Pro Arg Ile Ser Leu Pro Leu Gly Ser Glu Glu Arg Pro Phe
            100                 105                 110

Leu Arg Phe Glu Ala Glu His Ile Ser Asn Tyr Thr Ala Leu Leu Leu
        115                 120                 125

Ser Arg Asp Gly Arg Thr Leu Tyr Val Gly Ala Arg Glu Ala Leu Phe
    130                 135                 140

Ala Leu Ser Ser Asn Leu Ser Phe Leu Pro Gly Gly Glu Tyr Gln Glu
145                 150                 155                 160

Leu Leu Trp Gly Ala Asp Ala Glu Lys Lys Gln Gln Cys Ser Phe Lys
                165                 170                 175

Gly Lys Asp Pro Gln Arg Asp Cys Gln Asn Tyr Ile Lys Ile Leu Leu
            180                 185                 190

Pro Leu Ser Gly Ser His Leu Phe Thr Cys Gly Thr Ala Ala Phe Ser
        195                 200                 205

Pro Met Cys Thr Tyr Ile Asn Met Glu Asn Phe Thr Leu Ala Arg Asp
    210                 215                 220

Glu Lys Gly Asn Val Leu Leu Glu Asp Gly Lys Gly Arg Cys Pro Phe
225                 230                 235                 240
```

```
Asp Pro Asn Phe Lys Ser Thr Ala Leu Val Val Asp Gly Glu Leu Tyr
            245                 250                 255

Thr Gly Thr Val Ser Ser Phe Gln Gly Asn Asp Pro Ala Ile Ser Arg
            260                 265                 270

Ser Gln Ser Leu Arg Pro Thr Lys Thr Glu Ser Ser Leu Asn Trp Leu
            275                 280                 285

Gln Asp Pro Ala Phe Val Ala Ser Ala Tyr Ile Pro Glu Ser Leu Gly
            290                 295                 300

Ser Leu Gln Gly Asp Asp Lys Ile Tyr Phe Phe Ser Glu Thr
305                 310                 315                 320

Gly Gln Glu Phe Glu Phe Phe Glu Asn Thr Ile Val Ser Arg Ile Ala
            325                 330                 335

Arg Ile Cys Lys Gly Asp Glu Gly Glu Arg Val Leu Gln Gln Arg
            340                 345                 350

Trp Thr Ser Phe Leu Lys Ala Gln Leu Leu Cys Ser Arg Pro Asp Asp
            355                 360                 365

Gly Phe Pro Phe Asn Val Leu Gln Asp Val Phe Thr Leu Ser Pro Ser
    370                 375                 380

Pro Gln Asp Trp Arg Asp Thr Leu Phe Tyr Gly Val Phe Thr Ser Gln
385                 390                 395                 400

Trp His Arg Gly Thr Thr Glu Gly Ser Ala Val Cys Val Phe Thr Met
            405                 410                 415

Lys Asp Val Gln Arg Val Phe Ser Gly Leu Tyr Lys Glu Val Asn Arg
            420                 425                 430

Glu Thr Gln Gln Trp Tyr Thr Val Thr His Pro Val Pro Thr Pro Arg
            435                 440                 445

Pro Gly Ala Cys Ile Thr Asn Ser Ala Arg Glu Arg Lys Ile Asn Ser
    450                 455                 460

Ser Leu Gln Leu Pro Asp Arg Val Leu Asn Phe Leu Lys Asp His Phe
465                 470                 475                 480

Leu Met Asp Gly Gln Val Arg Ser Arg Met Leu Leu Leu Gln Pro Gln
            485                 490                 495

Ala Arg Tyr Gln Arg Val Ala Val His Arg Val Pro Gly Leu His His
            500                 505                 510

Thr Tyr Asp Val Leu Phe Leu Gly Thr Gly Asp Gly Arg Leu His Lys
            515                 520                 525

Ala Val Ser Val Gly Pro Arg Val His Ile Ile Glu Glu Leu Gln Ile
    530                 535                 540

Phe Ser Ser Gly Gln Pro Val Gln Asn Leu Leu Leu Asp Thr His Arg
545                 550                 555                 560

Gly Leu Leu Tyr Ala Ala Ser His Ser Gly Val Val Gln Val Pro Met
            565                 570                 575

Ala Asn Cys Ser Leu Tyr Arg Ser Cys Gly Asp Cys Leu Leu Ala Arg
            580                 585                 590

Asp Pro Tyr Cys Ala Trp Ser Gly Ser Ser Cys Lys His Val Ser Leu
    595                 600                 605

Tyr Gln Pro Gln Leu Ala Thr Arg Pro Trp Ile Gln Asp Ile Glu Gly
    610                 615                 620

Ala Ser Ala Lys Asp Leu Cys Ser Ala Ser Ser Val Val Ser Pro Ser
625                 630                 635                 640

Phe Val Pro Thr Gly Glu Lys Pro Cys Glu Gln Val Gln Phe Gln Pro
            645                 650                 655
```

```
Asn Thr Val Asn Thr Leu Ala Cys Pro Leu Leu Ser Asn Leu Ala Thr
                660                 665                 670
Arg Leu Trp Leu Arg Asn Gly Ala Pro Val Asn Ala Ser Ala Ser Cys
            675                 680                 685
His Val Leu Pro Thr Gly Asp Leu Leu Leu Val Gly Thr Gln Gln Leu
        690                 695                 700
Gly Glu Phe Gln Cys Trp Ser Leu Glu Glu Gly Phe Gln Gln Leu Val
705                 710                 715                 720
Ala Ser Tyr Cys Pro Glu Val Val Glu Asp Gly Val Ala Asp Gln Thr
                725                 730                 735
Asp Glu Gly Gly Ser Val Pro Val Ile Ile Ser Thr Ser Arg Val Ser
            740                 745                 750
Ala Pro Ser Thr Arg Leu Gly Pro Val Pro Gly Cys Arg Leu Leu
        755                 760                 765
```

<210> SEQ ID NO 3
<211> LENGTH: 3144
<212> TYPE: DNA
<213> ORGANISM: homo sapiens

<400> SEQUENCE: 3

```
atgcccagcc agggcagggt ggagagctgc agctgcaggt ccggaggcgg gggcccccgg      60
ggcgactcgg gggcggaccg cggggcggag ctgccgcccg tgagtccggc cgagccacct     120
gagcccgagc cgcgggacac cgtcgctcct gctctccgaa tgctgcgcac cgcgatgggc     180
ctgaggagct ggctcgccgc ccatggggc gcgctgccgc ctcggccacc gctgctgctg     240
ctcctgctgc tgctgctcct gctgcagccg ccgcctccga cctgggcgct cagccccggg     300
atcagcctgc tctgggctc tgaagagcgg ccattcctca gattcgaagc tgaacacatc     360
tccaactaca cagcccttct gctgagcagg gatggcagga ccctgtacgt gggtgctcga     420
gaggccctct ttgcactcag tagcaacctc agcttcctgc aggcggggga gtaccaggag     480
ctgctttggg gtgcagacgc agagaagaaa cagcagtgca gcttcaaggg caaggaccca     540
cagcgcgact gtcaaaacta catcaagatc ctcctgccgc tcagcggcag tcacctgttc     600
acctgtggca cagcagcctt cagccccatg tgtacctaca tcaacatgga aacttcacc     660
ctggcaaggg acgagaaggg gaatgtcctc tggaagatg caagggccg ttgtcccttc      720
gacccgaatt tcaagtccac tgccctggtg gttgatggcg agctctacac tggaacagtc     780
agcagcttcc aagggaatga cccggccatc tcgcggagcc aaagccttcg ccccaccaag     840
accgagagct ccctcaactg gctgcaagac ccagcttttg tggcctcagc ctacattcct     900
gagagcctgg gcagcttgca aggcgatgat gacaagatct actttttctt cagcgagact     960
ggccaggaat tgagttctt tgagaacacc attgtgtccc gcattgcccg catctgcaag    1020
ggcgatgagg tggagagcg ggtgctacag cagcgctgga cctccttcct caaggcccag    1080
ctgctgtgct cacggcccga cgatggcttc ccctttcacg tgctgcagga tgtcttcacg    1140
ctgagcccca gccccagga ctggcgtgac accctttttct atggggtctt cacttcccag    1200
tggcacaggg gaactacaga aggctctgcc gtctgtgtct tcacaatgaa ggatgtgcag    1260
agagtcttca gcggcctcta caaggaggtg aaccgtgaga cacagcagtg gtacaccgtg    1320
acccacccgg tgcccacacc ccggcctgga gcgtgcatca ccaacagtgc ccgggaaagg    1380
aagatcaact catccctgca gctcccagac cgcgtgctga acttcctcaa ggaccacttc    1440
ctgatggacg gcaggtccgg aagccgcatg ctgctgctgc agcccaggc tcgctaccag    1500
```

-continued

```
cgcgtggctg tacaccgcgt ccctggcctg caccacacct acgatgtcct cttcctgggc   1560
actggtgacg gccggctcca caaggcagtg agcgtgggcc cccgggtgca catcattgag   1620
gagctgcaga tcttctcatc gggacagccc gtgcagaatc tgctcctgga cacccacagg   1680
gggctgctgt atgcggcctc acactcgggc gtagtccagg tgcccatggc caactgcagc   1740
ctgtacagga gctgtgggga ctgcctcctc gcccgggacc cctactgtgc ttggagcggc   1800
tccagctgca agcacgtcag cctctaccag cctcagctgg ccaccaggcc gtggatccag   1860
gacatcgagg gagccagcgc caaggacctt tgcagcgcgt cttcggttgt gtccccgtct   1920
tttgtaccaa caggggagaa gccatgtgag caagtccagt tccagcccaa cacagtgaac   1980
actttggcct gcccgctcct ctccaacctg gcgacccgac tctggctacg caacggggcc   2040
cccgtcaatg cctcggcctc ctgccacgtg ctacccactg ggacctgct gctggtgggc   2100 acccaacagc tgggggagtt ccagtgctgg tcactagagg agggcttcca gcagctggta   2160
gccagctact gcccagaggt ggtggaggac ggggtggcag accaaacaga tacggtgccc   2220 acacccggc ctggagcgtg catcaccaac agtgcccggg aaggaagat caactcatcc   2280 ctgcagctcc cagaccgcgt gctgaacttc ctcaaggacc acttcctgat ggacgggcag   2340
gtccgaagcc gcatgctgct gctgcagccc caggctcgct accagcgcgt ggctgtacac   2400
cgcgtccctg gcctgcacca cacctacgat gtcctcttcc tgggcactgg tgacggccgg   2460
ctccacaagg cagtgagcgt gggcccccgg gtgcacatca ttgaggagct gcagatcttc   2520
tcatcgggac agcccgtgca gaatctgctc tggacacccc acaggggct gctgtatgcg   2580 gcctcacact cgggcgtagt ccaggtgccc atggccaact gcagcctgta caggagctgt   2640
ggggactgcc tcctcgcccg ggacccctac tgtgcttgga gcggctccag ctgcaagcac   2700
gtcagcctct accagcctca gctggccacc aggccgtgga tccaggacat cgagggagcc   2760
agcgccaagg acctttgcag cgcgtcttcg gttgtgtccc cgtcttttgt accaacaggg   2820
gagaagccat gtgagcaagt ccagttccag cccaacacag tgaacacttt ggcctgcccg   2880
ctcctctcca acctgcgac ccgactctgg ctacgcaacg ggccccccgt caatgcctcg   2940
gcctcctgcc acgtgctacc cactggggac ctgctgctgg tgggcactgg agtagcacct   3000
tccacgacca ggagaggcac tggggagggg tcacagggat gccacccggg cagacctgag   3060
gaagagatgg aggtggacgt gtcagcaccc ggctggggcc tgtccctgga tgcaggctac   3120
tctagggcac ctgtcccgcc ttga                                          3144
```

<210> SEQ ID NO 4
<211> LENGTH: 1047
<212> TYPE: PRT
<213> ORGANISM: homo sapiens

<400> SEQUENCE: 4

```
Met Pro Ser Gln Gly Arg Val Glu Ser Cys Ser Cys Arg Ser Gly Gly
 1               5                  10                  15

Gly Gly Pro Arg Gly Asp Ser Gly Ala Asp Arg Gly Ala Glu Leu Pro
            20                  25                  30

Pro Val Ser Pro Ala Glu Pro Glu Pro Glu Pro Arg Asp Thr Val
        35                  40                  45

Ala Pro Ala Leu Arg Met Leu Arg Thr Ala Met Gly Leu Arg Ser Trp
    50                  55                  60

Leu Ala Ala Pro Trp Gly Ala Leu Pro Pro Arg Pro Pro Leu Leu Leu
65                  70                  75                  80
```

-continued

```
Leu Leu Leu Leu Leu Leu Leu Gln Pro Pro Pro Thr Trp Ala
              85                  90              95
Leu Ser Pro Arg Ile Ser Leu Pro Leu Gly Ser Glu Glu Arg Pro Phe
             100             105             110
Leu Arg Phe Glu Ala Glu His Ile Ser Asn Tyr Thr Ala Leu Leu Leu
             115                 120             125
Ser Arg Asp Gly Arg Thr Leu Tyr Val Gly Ala Arg Glu Ala Leu Phe
130             135                 140
Ala Leu Ser Ser Asn Leu Ser Phe Leu Pro Gly Gly Glu Tyr Gln Glu
145                 150             155                 160
Leu Leu Trp Gly Ala Asp Ala Glu Lys Lys Gln Gln Cys Ser Phe Lys
                165             170                 175
Gly Lys Asp Pro Gln Arg Asp Cys Gln Asn Tyr Ile Lys Ile Leu Leu
            180             185             190
Pro Leu Ser Gly Ser His Leu Phe Thr Cys Gly Thr Ala Ala Phe Ser
            195             200             205
Pro Met Cys Thr Tyr Ile Asn Met Glu Asn Phe Thr Leu Ala Arg Asp
    210             215             220
Glu Lys Gly Asn Val Leu Leu Glu Asp Gly Lys Gly Arg Cys Pro Phe
225             230             235             240
Asp Pro Asn Phe Lys Ser Thr Ala Leu Val Val Asp Gly Glu Leu Tyr
            245             250             255
Thr Gly Thr Val Ser Ser Phe Gln Gly Asn Asp Pro Ala Ile Ser Arg
            260             265             270
Ser Gln Ser Leu Arg Pro Thr Lys Thr Glu Ser Ser Leu Asn Trp Leu
            275             280             285
Gln Asp Pro Ala Phe Val Ala Ser Ala Tyr Ile Pro Glu Ser Leu Gly
    290             295             300
Ser Leu Gln Gly Asp Asp Asp Lys Ile Tyr Phe Phe Phe Ser Glu Thr
305             310             315             320
Gly Gln Glu Phe Glu Phe Phe Glu Asn Thr Ile Val Ser Arg Ile Ala
                325             330             335
Arg Ile Cys Lys Gly Asp Glu Gly Gly Glu Arg Val Leu Gln Gln Arg
            340             345             350
Trp Thr Ser Phe Leu Lys Ala Gln Leu Leu Cys Ser Arg Pro Asp Asp
            355             360             365
Gly Phe Pro Phe Asn Val Leu Gln Asp Val Phe Thr Leu Ser Pro Ser
    370             375             380
Pro Gln Asp Trp Arg Asp Thr Leu Phe Tyr Gly Val Phe Thr Ser Gln
385             390             395             400
Trp His Arg Gly Thr Thr Glu Gly Ser Ala Val Cys Val Phe Thr Met
                405             410             415
Lys Asp Val Gln Arg Val Phe Ser Gly Leu Tyr Lys Glu Val Asn Arg
            420             425             430
Glu Thr Gln Gln Trp Tyr Thr Val Thr His Pro Val Pro Thr Pro Arg
            435             440             445
Pro Gly Ala Cys Ile Thr Asn Ser Ala Arg Glu Arg Lys Ile Asn Ser
    450             455             460
Ser Leu Gln Leu Pro Asp Arg Val Leu Asn Phe Leu Lys Asp His Phe
465             470             475             480
Leu Met Asp Gly Gln Val Arg Ser Arg Met Leu Leu Leu Gln Pro Gln
                485             490             495
Ala Arg Tyr Gln Arg Val Ala Val His Arg Val Pro Gly Leu His His
```

```
                500                 505                 510
Thr Tyr Asp Val Leu Phe Leu Gly Thr Gly Asp Gly Arg Leu His Lys
        515                 520                 525
Ala Val Ser Val Gly Pro Arg Val His Ile Ile Glu Glu Leu Gln Ile
530                 535                 540
Phe Ser Ser Gly Gln Pro Val Gln Asn Leu Leu Asp Thr His Arg
545                 550                 555                 560
Gly Leu Leu Tyr Ala Ala Ser His Ser Gly Val Val Gln Val Pro Met
                565                 570                 575
Ala Asn Cys Ser Leu Tyr Arg Ser Cys Gly Asp Cys Leu Leu Ala Arg
            580                 585                 590
Asp Pro Tyr Cys Ala Trp Ser Gly Ser Cys Lys His Val Ser Leu
            595                 600                 605
Tyr Gln Pro Gln Leu Ala Thr Arg Pro Trp Ile Gln Asp Ile Glu Gly
        610                 615                 620
Ala Ser Ala Lys Asp Leu Cys Ser Ala Ser Val Val Ser Pro Ser
625                 630                 635                 640
Phe Val Pro Thr Gly Glu Lys Pro Cys Glu Gln Val Gln Phe Gln Pro
                645                 650                 655
Asn Thr Val Asn Thr Leu Ala Cys Pro Leu Leu Ser Asn Leu Ala Thr
            660                 665                 670
Arg Leu Trp Leu Arg Asn Gly Ala Pro Val Asn Ala Ser Ala Ser Cys
        675                 680                 685
His Val Leu Pro Thr Gly Asp Leu Leu Leu Val Gly Thr Gln Gln Leu
        690                 695                 700
Gly Glu Phe Gln Cys Trp Ser Leu Glu Glu Gly Phe Gln Gln Leu Val
705                 710                 715                 720
Ala Ser Tyr Cys Pro Glu Val Val Glu Asp Gly Val Ala Asp Gln Thr
                725                 730                 735
Asp Thr Val Pro Thr Pro Arg Pro Gly Ala Cys Ile Thr Asn Ser Ala
            740                 745                 750
Arg Glu Arg Lys Ile Asn Ser Ser Leu Gln Leu Pro Asp Arg Val Leu
        755                 760                 765
Asn Phe Leu Lys Asp His Phe Leu Met Asp Gly Gln Val Arg Ser Arg
770                 775                 780
Met Leu Leu Leu Gln Pro Gln Ala Arg Tyr Gln Arg Val Ala Val His
785                 790                 795                 800
Arg Val Pro Gly Leu His His Thr Tyr Asp Val Leu Phe Leu Gly Thr
                805                 810                 815
Gly Asp Gly Arg Leu His Lys Ala Val Ser Val Gly Pro Arg Val His
            820                 825                 830
Ile Ile Glu Glu Leu Gln Ile Phe Ser Ser Gly Gln Pro Val Gln Asn
        835                 840                 845
Leu Leu Leu Asp Thr His Arg Gly Leu Leu Tyr Ala Ala Ser His Ser
        850                 855                 860
Gly Val Val Gln Val Pro Met Ala Asn Cys Ser Leu Tyr Arg Ser Cys
865                 870                 875                 880
Gly Asp Cys Leu Leu Ala Arg Asp Pro Tyr Cys Ala Trp Ser Gly Ser
                885                 890                 895
Ser Cys Lys His Val Ser Leu Tyr Gln Pro Gln Leu Ala Thr Arg Pro
            900                 905                 910
Trp Ile Gln Asp Ile Glu Gly Ala Ser Ala Lys Asp Leu Cys Ser Ala
        915                 920                 925
```

-continued

```
Ser Ser Val Val Ser Pro Ser Phe Val Pro Thr Gly Glu Lys Pro Cys
        930                 935                 940

Glu Gln Val Gln Phe Gln Pro Asn Thr Val Asn Thr Leu Ala Cys Pro
945                 950                 955                 960

Leu Leu Ser Asn Leu Ala Thr Arg Leu Trp Leu Arg Asn Gly Ala Pro
                965                 970                 975

Val Asn Ala Ser Ala Ser Cys His Val Leu Pro Thr Gly Asp Leu Leu
            980                 985                 990

Leu Val Gly Thr Gly Val Ala Pro Ser Thr Thr Arg Arg Gly Thr Gly
        995                 1000                1005

Glu Gly Ser Gln Gly Cys His Pro Gly Arg Pro Glu Glu Met Glu
    1010                1015                1020

Val Asp Val Ser Ala Pro Gly Trp Gly Leu Ser Leu Asp Ala Gly Tyr
1025                1030                1035                1040

Ser Arg Ala Pro Val Pro Pro
                1045
```

<210> SEQ ID NO 5
<211> LENGTH: 3189
<212> TYPE: DNA
<213> ORGANISM: homo sapiens

<400> SEQUENCE: 5

| | |
|---|---|
| atgcccagcc agggcagggt ggagagctgc agctgcaggt ccggaggcgg gggcccccgg | 60 |
| ggcgactcgg gggcggaccg cggggcggag ctgccgcccg tgagtccggc cgagccacct | 120 |
| gagcccgagc cgcgggacac cgtcgctcct gctctccgaa tgctgcgcac cgcgatgggc | 180 |
| ctgaggagct ggctcgccgc ccatggggc gcgctgccgc ctcggccacc gctgctgctg | 240 |
| ctcctgctgc tgctgctcct gctgcagccg ccgcctccga cctgggcgct cagccccgg | 300 |
| atcagcctgc tctgggctc tgaagagcgg ccattcctca gattcgaagc tgaacacatc | 360 |
| tccaactaca cagcccttct gctgagcagg gatggcagga ccctgtacgt gggtgctcga | 420 |
| gaggccctct ttgcactcag tagcaacctc agcttcctgc aggcggggga gtaccaggag | 480 |
| ctgctttggg gtgcagacgc agagaagaaa cagcagtgca gcttcaaggg caaggaccca | 540 |
| cagcgcgact gtcaaaacta catcaagatc tcctgccgc tcagcggcag tcacctgttc | 600 |
| acctgtggca cagcagcctt cagccccatg tgtacctaca tcaacatgga aacttcacc | 660 |
| ctggcaaggg acgagaaggg gaatgtcctc tggaagatg gcaagggccg ttgtcccttc | 720 |
| gacccgaatt tcaagtccac tgccctggtg gttgatggcg agctctacac tggaacagtc | 780 |
| agcagcttcc aagggaatga cccggccatc tcgcggagcc aaagccttcg ccccaccaag | 840 |
| accgagagct ccctcaactg ctgcaagac ccagcttttg tggcctcagc ctacattcct | 900 |
| gagagcctgg gcagcttgca aggcgatgat gacaagatct actttttctt cagcgagact | 960 |
| ggccaggaat ttgagttctt tgagaacacc attgtgtccc gcattgcccg catctgcaag | 1020 |
| ggcgatgagg tggagagcg ggtgctacag cagcgctgga cctccttcct caaggcccag | 1080 |
| ctgctgtgct cacggcccga cgatggcttc cccttcaacg tgctgcagga tgtcttcacg | 1140 |
| ctgagcccca gccccagga ctggcgtgac cccttttct atgggtctt cacttcccag | 1200 |
| tggcacaggg gaactacaga aggctctgcc gtctgtgtct tcacaatgaa ggatgtgcag | 1260 |
| agagtcttca gcggcctcta caaggaggtg aaccgtgaga cacagcagtg gtacaccgtg | 1320 |
| acccacccgg tgcccacacc ccggcctgga gcgtgcatca ccaacagtgc ccgggaaagg | 1380 |

-continued

```
aagatcaact catccctgca gctcccagac cgcgtgctga acttcctcaa ggaccacttc      1440
ctgatggacg ggcaggtccg aagccgcatg ctgctgctgc agccccaggc tcgctaccag      1500
cgcgtggctg tacaccgcgt ccctggcctg caccacacct acgatgtcct cttcctgggc      1560
actggtgacg gccggctcca caaggcagtg agcgtgggcc cccgggtgca catcattgag      1620
gagctgcaga tcttctcatc gggacagccc gtgcagaatc tgctcctgga cacccacagg      1680
gggctgctgt atgcggcctc acactcgggc gtagtccagg tgcccatggc caactgcagc      1740
ctgtacagga gctgtgggga ctgcctcctc gcccgggacc cctactgtgc ttggagcggc      1800
tccagctgca agcacgtcag cctctaccag cctcagctgg ccaccaggcc gtggatccag      1860
gacatcgagg gagccagcgc caaggacctt gcagcgcgt cttcggttgt gtccccgtct       1920
tttgtaccaa caggggagaa gccatgtgag caagtccagt tccagcccaa cacagtgaac      1980
actttggcct gcccgctcct ctccaacctg gcgacccgac tctggctacg caacggggcc      2040
cccgtcaatg cctcggcctc ctgccacgtg ctacccactg gggacctgct gctggtgggc      2100
acccaacagc tgggggagtt ccagtgctgg tcactagagg agggcttcca gcagctggta      2160
gccagctact gcccagaggt ggtggaggac ggggtggcag accaaacaga tacggtgccc      2220
acaccccggc ctggagcgtg catcaccaac agtgcccggg aaaggaagat caactcatcc      2280
ctgcagctcc cagaccgcgt gctgaacttc ctcaaggacc acttcctgat ggacgggcag      2340
gtccgaagcc gcatgctgct gctgcagccc caggctcgct accagcgcgt ggctgtacac      2400
cgcgtccctg gcctgcacca cacctacgat gtcctcttcc tgggcactgg tgacggccgg      2460
ctccacaagg cagtgagcgt gggcccccgg gtgcacatca ttgaggagct gcagatcttc      2520
tcatcgggac agcccgtgca gaatctgctc tggacacccc acaggggct gctgtatgcg      2580 gcctcacact cgggcgtagt ccaggtgccc atggccaact gcagcctgta caggagctgt      2640
ggggactgcc tcctcgcccg ggaccctac tgtgcttgga gcggctccag ctgcaagcac       2700
gtcagcctct accagcctca gctggccacc aggccgtgga tccaggacat cgagggagcc      2760
agcgccaagg acctttgcag cgcgtcttcg gttgtgtccc cgtcttttgt accaacaggg      2820
gagaagccat gtgagcaagt ccagttccag cccaacacag tgaacacttt ggcctgcccg      2880
ctcctctcca acctggcgac ccgactctgg ctacgcaacg ggccccccgt caatgcctcg      2940
gcctcctgcc acgtgctacc cactggggac ctgctgctgg tgggcaccca acagctgggg      3000
gagttccagt gctggtcact agaggagggc ttccagcagc tggtagccag ctactgccca      3060
gaggtggtgg aggacggggt ggcaaaccaa acagatgagg gtggcagtgt acccgtcatt      3120
atcagcacat cgcgtgtgag tgcacccagc acccggctgg ggcctgtccc tggatgcagg      3180
ctactctag                                                              3189
```

<210> SEQ ID NO 6
<211> LENGTH: 1062
<212> TYPE: PRT
<213> ORGANISM: homo sapiens

<400> SEQUENCE: 6

```
Met Pro Ser Gln Gly Arg Val Glu Ser Cys Ser Cys Arg Ser Gly Gly
  1               5                  10                  15

Gly Gly Pro Arg Gly Asp Ser Gly Ala Asp Arg Gly Ala Glu Leu Pro
             20                  25                  30

Pro Val Ser Pro Ala Glu Pro Pro Glu Pro Glu Pro Arg Asp Thr Val
         35                  40                  45
```

```
Ala Pro Ala Leu Arg Met Leu Arg Thr Ala Met Gly Leu Arg Ser Trp
 50                  55                  60
Leu Ala Ala Pro Trp Gly Ala Leu Pro Pro Arg Pro Pro Leu Leu Leu
 65                      70                  75                  80
Leu Leu Leu Leu Leu Leu Leu Gln Pro Pro Pro Thr Trp Ala
                     85                  90                  95
Leu Ser Pro Arg Ile Ser Leu Pro Leu Gly Ser Glu Glu Arg Pro Phe
                100                 105                 110
Leu Arg Phe Glu Ala Glu His Ile Ser Asn Tyr Thr Ala Leu Leu Leu
            115                 120                 125
Ser Arg Asp Gly Arg Thr Leu Tyr Val Gly Ala Arg Glu Ala Leu Phe
        130                 135                 140
Ala Leu Ser Ser Asn Leu Ser Phe Leu Pro Gly Gly Glu Tyr Gln Glu
145                 150                 155                 160
Leu Leu Trp Gly Ala Asp Ala Glu Lys Lys Gln Gln Cys Ser Phe Lys
                165                 170                 175
Gly Lys Asp Pro Gln Arg Asp Cys Gln Asn Tyr Ile Lys Ile Leu Leu
                180                 185                 190
Pro Leu Ser Gly Ser His Leu Phe Thr Cys Gly Thr Ala Ala Phe Ser
                195                 200                 205
Pro Met Cys Thr Tyr Ile Asn Met Glu Asn Phe Thr Leu Ala Arg Asp
210                 215                 220
Glu Lys Gly Asn Val Leu Leu Glu Asp Gly Lys Gly Arg Cys Pro Phe
225                 230                 235                 240
Asp Pro Asn Phe Lys Ser Thr Ala Leu Val Val Asp Gly Glu Leu Tyr
                245                 250                 255
Thr Gly Thr Val Ser Ser Phe Gln Gly Asn Asp Pro Ala Ile Ser Arg
                260                 265                 270
Ser Gln Ser Leu Arg Pro Thr Lys Thr Glu Ser Ser Leu Asn Trp Leu
            275                 280                 285
Gln Asp Pro Ala Phe Val Ala Ser Ala Tyr Ile Pro Glu Ser Leu Gly
        290                 295                 300
Ser Leu Gln Gly Asp Asp Asp Lys Ile Tyr Phe Phe Ser Glu Thr
305                 310                 315                 320
Gly Gln Glu Phe Glu Phe Phe Glu Asn Thr Ile Val Ser Arg Ile Ala
                325                 330                 335
Arg Ile Cys Lys Gly Asp Glu Gly Gly Glu Arg Val Leu Gln Gln Arg
                340                 345                 350
Trp Thr Ser Phe Leu Lys Ala Gln Leu Leu Cys Ser Arg Pro Asp Asp
            355                 360                 365
Gly Phe Pro Phe Asn Val Leu Gln Asp Val Phe Thr Leu Ser Pro Ser
        370                 375                 380
Pro Gln Asp Trp Arg Asp Thr Leu Phe Tyr Gly Val Phe Thr Ser Gln
385                 390                 395                 400
Trp His Arg Gly Thr Thr Glu Gly Ser Ala Val Cys Val Phe Thr Met
                405                 410                 415
Lys Asp Val Gln Arg Val Phe Ser Gly Leu Tyr Lys Glu Val Asn Arg
                420                 425                 430
Glu Thr Gln Gln Trp Tyr Thr Val Thr His Pro Val Pro Thr Pro Arg
            435                 440                 445
Pro Gly Ala Cys Ile Thr Asn Ser Ala Arg Glu Arg Lys Ile Asn Ser
        450                 455                 460
Ser Leu Gln Leu Pro Asp Arg Val Leu Asn Phe Leu Lys Asp His Phe
```

```
                465                 470                 475                 480
Leu Met Asp Gly Gln Val Arg Ser Arg Met Leu Leu Gln Pro Gln
                    485                 490                 495
Ala Arg Tyr Gln Arg Val Ala Val His Arg Val Pro Gly Leu His His
                500                 505                 510
Thr Tyr Asp Val Leu Phe Leu Gly Thr Gly Asp Gly Arg Leu His Lys
                515                 520                 525
Ala Val Ser Val Gly Pro Arg Val His Ile Ile Glu Glu Leu Gln Ile
            530                 535                 540
Phe Ser Ser Gly Gln Pro Val Gln Asn Leu Leu Leu Asp Thr His Arg
545                 550                 555                 560
Gly Leu Leu Tyr Ala Ala Ser His Ser Gly Val Val Gln Val Pro Met
                    565                 570                 575
Ala Asn Cys Ser Leu Tyr Arg Ser Cys Gly Asp Cys Leu Leu Ala Arg
                580                 585                 590
Asp Pro Tyr Cys Ala Trp Ser Gly Ser Ser Cys Lys His Val Ser Leu
            595                 600                 605
Tyr Gln Pro Gln Leu Ala Thr Arg Pro Trp Ile Gln Asp Ile Glu Gly
        610                 615                 620
Ala Ser Ala Lys Asp Leu Cys Ser Ala Ser Val Val Ser Pro Ser
625                 630                 635                 640
Phe Val Pro Thr Gly Glu Lys Pro Cys Glu Gln Val Gln Phe Gln Pro
                    645                 650                 655
Asn Thr Val Asn Thr Leu Ala Cys Pro Leu Leu Ser Asn Leu Ala Thr
                660                 665                 670
Arg Leu Trp Leu Arg Asn Gly Ala Pro Val Asn Ala Ser Ala Ser Cys
            675                 680                 685
His Val Leu Pro Thr Gly Asp Leu Leu Val Gly Thr Gln Gln Leu
        690                 695                 700
Gly Glu Phe Gln Cys Trp Ser Leu Glu Glu Gly Phe Gln Gln Leu Val
705                 710                 715                 720
Ala Ser Tyr Cys Pro Glu Val Val Glu Asp Gly Val Ala Asp Gln Thr
                725                 730                 735
Asp Thr Val Pro Thr Pro Arg Pro Gly Ala Cys Ile Thr Asn Ser Ala
                740                 745                 750
Arg Glu Arg Lys Ile Asn Ser Ser Leu Gln Leu Pro Asp Arg Val Leu
            755                 760                 765
Asn Phe Leu Lys Asp His Phe Leu Met Asp Gly Gln Val Arg Ser Arg
        770                 775                 780
Met Leu Leu Leu Gln Pro Gln Ala Arg Tyr Gln Arg Val Ala Val His
785                 790                 795                 800
Arg Val Pro Gly Leu His His Thr Tyr Asp Val Leu Phe Leu Gly Thr
                    805                 810                 815
Gly Asp Gly Arg Leu His Lys Ala Val Ser Val Gly Pro Arg Val His
                820                 825                 830
Ile Ile Glu Glu Leu Gln Ile Phe Ser Ser Gly Gln Pro Val Gln Asn
            835                 840                 845
Leu Leu Leu Asp Thr His Arg Gly Leu Leu Tyr Ala Ala Ser His Ser
        850                 855                 860
Gly Val Val Gln Val Pro Met Ala Asn Cys Ser Leu Tyr Arg Ser Cys
865                 870                 875                 880
Gly Asp Cys Leu Leu Ala Arg Asp Pro Tyr Cys Ala Trp Ser Gly Ser
                    885                 890                 895
```

| | | | | | | | | | | | |
|---|---|---|---|---|---|---|---|---|---|---|---|
|Ser|Cys|Lys|His|Val|Ser|Leu|Tyr|Gln|Pro|Gln|Leu|Ala|Thr|Arg|Pro|

Ser Cys Lys His Val Ser Leu Tyr Gln Pro Gln Leu Ala Thr Arg Pro
            900                 905                 910
Trp Ile Gln Asp Ile Glu Gly Ala Ser Ala Lys Asp Leu Cys Ser Ala
            915                 920                 925
Ser Ser Val Val Ser Pro Ser Phe Val Pro Thr Gly Glu Lys Pro Cys
            930                 935                 940
Glu Gln Val Gln Phe Gln Pro Asn Thr Val Asn Thr Leu Ala Cys Pro
945                 950                 955                 960
Leu Leu Ser Asn Leu Ala Thr Arg Leu Trp Leu Arg Asn Gly Ala Pro
            965                 970                 975
Val Asn Ala Ser Ala Ser Cys His Val Leu Pro Thr Gly Asp Leu Leu
            980                 985                 990
Leu Val Gly Thr Gln Gln Leu Gly Glu Phe Gln Cys Trp Ser Leu Glu
            995                 1000                1005
Glu Gly Phe Gln Gln Leu Val Ala Ser Tyr Cys Pro Glu Val Val Glu
            1010                1015                1020
Asp Gly Val Ala Asn Gln Thr Asp Glu Gly Gly Ser Val Pro Val Ile
1025                1030                1035                1040
Ile Ser Thr Ser Arg Val Ser Ala Pro Ser Thr Arg Leu Gly Pro Val
            1045                1050                1055
Pro Gly Cys Arg Leu Leu
            1060

<210> SEQ ID NO 7
<211> LENGTH: 2517
<212> TYPE: DNA
<213> ORGANISM: homo sapiens

<400> SEQUENCE: 7

```
atgcccagcc agggcagggt ggagagctgc agctgcaggt ccggaggcgg gggcccccgg      60
ggcgactcgg gggcggaccg cggggcggag ctgccgcccg tgagtccggc cgagccacct     120
gagcccgagc cgcgggacac cgtcgctcct gctctccgaa tgctgcgcac cgcgatgggc     180
ctgaggagct ggctcgccgc cccatggggc gcgctgccgc ctcggccacc gctgctgctg     240
ctcctgctgc tgctgctcct gctgcagccc ccgcctccga cctgggcgct cagcccccgg     300
atcagcctgc tctgggctc tgaagagcgg ccattcctca gattcgaagc tgaacacatc     360
tccaactaca gcccttct gctgagcagg gatggcagga ccctgtacgt gggtgctcga      420
gaggccctct ttgcactcag tagcaacctc agcttcctgc aggcggggga gtaccaggag     480
ctgctttggg gtgcagacgc agagaagaaa cagcagtgca gcttcaaggg caaggaccca     540
cagcgcgact gtcaaaacta catcaagatc ctcctgccgc tcagcggcag tcacctgttc     600
acctgtggca gcagccttc agccccatg tgtacctaca tcaacatgga aacttcacc      660
ctggcaaggg acgagaaggg gaatgtcctc tggaagatgc aagggccg ttgtcccttc      720
gacccgaatt tcaagtccac tgccctggtg gttgatggcg agctctacac tggaacagtc     780
agcagcttcc aagggaatga cccggccatc tcgcggagcc aaagccttcg ccccaccaag     840
accgagagct ccctcaactg gctgcaagac ccagcttttg tggcctcagc ctacattcct     900
gagagcctgg gcagcttgca aggcgatgat gacaagatct acttttctt cagcgagact     960
ggccaggaat tgagttctt tgagaacacc attgtgtccc gcattgcccg catctgcaag    1020
ggcgatgagg tgagagcg ggtgctacag cagcgctgga cctccttcct caaggcccag    1080
ctgctgtgct cacggcccga cgatggcttc cccttcaacg tgctgcagga tgtcttcacg    1140
```

-continued

```
ctgagcccca gcccccagga ctggcgtgac acccttttct atggggtctt cacttcccag   1200
tggcacaggg gaactacaga aggctctgcc gtctgtgtct tcacaatgaa ggatgtgcag   1260
agagtcttca gcggcctcta caaggaggtg aaccgtgaga cacagcagtg gtacaccgtg   1320
acccacccgg tgcccacacc ccggcctgga gcgtgcatca ccaacagtgc ccgggaaagg   1380
aagatcaact catccctgca gctcccagac cgcgtgctga acttcctcaa ggaccacttc   1440
ctgatggacg ggcaggtccg aagccgcatg ctgctgctgc agccccaggc tcgctaccag   1500
cgcgtggctg tacaccgcgt ccctggcctg caccacacct acgatgtcct cttcctgggc   1560
actggtgacg gccggctcca caaggcagtg agcgtgggcc cccgggtgca catcattgag   1620
gagctgcaga tcttctcatc gggacagccc gtgcagaatc tgctcctgga cacccacagg   1680
gggctgctgt atgcggcctc acactcgggc gtagtccagg tgcccatggc caactgcagc   1740
ctgtacagga gctgtgggga ctgcctcctc gcccgggacc cctactgtgc ttggagcggc   1800
tccagctgca agcacgtcag cctctaccag cctcagctgg ccaccaggcc gtggatccag   1860
gacatcgagg gagccagcgc caaggacctt tgcagcgcgt cttcggttgt gtccccgtct   1920
tttgtaccaa cagggggagaa gccatgtgag caagtccagt tccagcccaa cacagtgaac   1980
actttggcct gcccgctcct ctccaacctg gcgacccgac tctggctacg aacggggcc    2040 cccgtcaatg cctcggcctc ctgccacgtg ctacccactg gggacctgct gctggtgggc   2100
acccaacagc tgggggagtt ccagtgctgg tcactagagg agggcttcca gcagctggta   2160
gccagctact gcccagaggt ggtggaggac ggggtggcag accaaacaga tgagggtggc   2220
agtgtacccg tcattatcag cacatcgcgt gtgagtgcac cagctggtgg caaggccagc   2280
tggggtgcag acaggtccta ctggaaggag ttcctggtga tgtgcacgct ctttgtgctg   2340
gccgtgctgc tcccagtttt attcttgctc taccggcacc ggaacagcat gaaagtcttc   2400
ctgaagcagg gggaatgtgc cagcgtgcac cccaagacct gccctgtggt gctgccccct   2460
gagacccgcc ctcggtttca ccgtcaccgc cgacgtcgag gtgactcaac ggcctag     2517
```

<210> SEQ ID NO 8
<211> LENGTH: 838
<212> TYPE: PRT
<213> ORGANISM: homo sapiens

<400> SEQUENCE: 8

```
Met Pro Ser Gln Gly Arg Val Glu Ser Cys Ser Cys Arg Ser Gly Gly
 1               5                  10                  15

Gly Gly Pro Arg Gly Asp Ser Gly Ala Asp Arg Gly Ala Glu Leu Pro
            20                  25                  30

Pro Val Ser Pro Ala Glu Pro Glu Pro Glu Pro Arg Asp Thr Val
        35                  40                  45

Ala Pro Ala Leu Arg Met Leu Arg Thr Ala Met Gly Leu Arg Ser Trp
    50                  55                  60

Leu Ala Ala Pro Trp Gly Ala Leu Pro Pro Arg Pro Leu Leu Leu
65                  70                  75                  80

Leu Leu Leu Leu Leu Leu Leu Gln Pro Pro Pro Thr Trp Ala
                85                  90                  95

Leu Ser Pro Arg Ile Ser Leu Pro Leu Gly Ser Glu Glu Arg Pro Phe
            100                 105                 110

Leu Arg Phe Glu Ala Glu His Ile Ser Asn Tyr Thr Ala Leu Leu Leu
        115                 120                 125
```

```
Ser Arg Asp Gly Arg Thr Leu Tyr Val Gly Ala Arg Glu Ala Leu Phe
130                 135                 140

Ala Leu Ser Ser Asn Leu Ser Phe Leu Pro Gly Gly Glu Tyr Gln Glu
145                 150                 155                 160

Leu Leu Trp Gly Ala Asp Ala Glu Lys Lys Gln Gln Cys Ser Phe Lys
                165                 170                 175

Gly Lys Asp Pro Gln Arg Asp Cys Gln Asn Tyr Ile Lys Ile Leu Leu
                180                 185                 190

Pro Leu Ser Gly Ser His Leu Phe Thr Cys Gly Thr Ala Ala Phe Ser
                195                 200                 205

Pro Met Cys Thr Tyr Ile Asn Met Glu Asn Phe Thr Leu Ala Arg Asp
210                 215                 220

Glu Lys Gly Asn Val Leu Leu Glu Asp Gly Lys Gly Arg Cys Pro Phe
225                 230                 235                 240

Asp Pro Asn Phe Lys Ser Thr Ala Leu Val Val Asp Gly Glu Leu Tyr
                245                 250                 255

Thr Gly Thr Val Ser Ser Phe Gln Gly Asn Asp Pro Ala Ile Ser Arg
                260                 265                 270

Ser Gln Ser Leu Arg Pro Thr Lys Thr Glu Ser Ser Leu Asn Trp Leu
                275                 280                 285

Gln Asp Pro Ala Phe Val Ala Ser Ala Tyr Ile Pro Glu Ser Leu Gly
290                 295                 300

Ser Leu Gln Gly Asp Asp Lys Ile Tyr Phe Phe Ser Glu Thr
305                 310                 315                 320

Gly Gln Glu Phe Glu Phe Glu Asn Thr Ile Val Ser Arg Ile Ala
                325                 330                 335

Arg Ile Cys Lys Gly Asp Glu Gly Glu Arg Val Leu Gln Gln Arg
                340                 345                 350

Trp Thr Ser Phe Leu Lys Ala Gln Leu Leu Cys Ser Arg Pro Asp Asp
                355                 360                 365

Gly Phe Pro Phe Asn Val Leu Gln Asp Val Phe Thr Leu Ser Pro Ser
370                 375                 380

Pro Gln Asp Trp Arg Asp Thr Leu Phe Tyr Gly Val Phe Thr Ser Gln
385                 390                 395                 400

Trp His Arg Gly Thr Thr Glu Gly Ser Ala Val Cys Val Phe Thr Met
                405                 410                 415

Lys Asp Val Gln Arg Val Phe Ser Gly Leu Tyr Lys Glu Val Asn Arg
                420                 425                 430

Glu Thr Gln Gln Trp Tyr Thr Val Thr His Pro Val Pro Thr Pro Arg
                435                 440                 445

Pro Gly Ala Cys Ile Thr Asn Ser Ala Arg Glu Arg Lys Ile Asn Ser
450                 455                 460

Ser Leu Gln Leu Pro Asp Arg Val Leu Asn Phe Leu Lys Asp His Phe
465                 470                 475                 480

Leu Met Asp Gly Gln Val Arg Ser Arg Met Leu Leu Gln Pro Gln
                485                 490                 495

Ala Arg Tyr Gln Arg Val Ala Val His Arg Val Pro Gly Leu His His
                500                 505                 510

Thr Tyr Asp Val Leu Phe Leu Gly Thr Gly Asp Gly Arg Leu His Lys
                515                 520                 525

Ala Val Ser Val Gly Pro Arg Val His Ile Ile Glu Glu Leu Gln Ile
530                 535                 540

Phe Ser Ser Gly Gln Pro Val Gln Asn Leu Leu Leu Asp Thr His Arg
```

```
                545                 550                 555                 560
           Gly Leu Leu Tyr Ala Ala Ser His Ser Gly Val Val Gln Val Pro Met
                           565                 570                 575
           Ala Asn Cys Ser Leu Tyr Arg Ser Cys Gly Asp Cys Leu Leu Ala Arg
                           580                 585                 590
           Asp Pro Tyr Cys Ala Trp Ser Gly Ser Ser Cys Lys His Val Ser Leu
                           595                 600                 605
           Tyr Gln Pro Gln Leu Ala Thr Arg Pro Trp Ile Gln Asp Ile Glu Gly
                           610                 615                 620
           Ala Ser Ala Lys Asp Leu Cys Ser Ala Ser Val Val Ser Pro Ser
           625                 630                 635                 640
           Phe Val Pro Thr Gly Glu Lys Pro Cys Glu Gln Val Gln Phe Gln Pro
                           645                 650                 655
           Asn Thr Val Asn Thr Leu Ala Cys Pro Leu Leu Ser Asn Leu Ala Thr
                           660                 665                 670
           Arg Leu Trp Leu Arg Asn Gly Ala Pro Val Asn Ala Ser Ala Ser Cys
                           675                 680                 685
           His Val Leu Pro Thr Gly Asp Leu Leu Val Gly Thr Gln Gln Leu
                           690                 695                 700
           Gly Glu Phe Gln Cys Trp Ser Leu Glu Glu Gly Phe Gln Gln Leu Val
           705                 710                 715                 720
           Ala Ser Tyr Cys Pro Glu Val Val Glu Asp Gly Val Ala Asp Gln Thr
                           725                 730                 735
           Asp Glu Gly Gly Ser Val Pro Val Ile Ile Ser Thr Ser Arg Val Ser
                           740                 745                 750
           Ala Pro Ala Gly Gly Lys Ala Ser Trp Gly Ala Asp Arg Ser Tyr Trp
                           755                 760                 765
           Lys Glu Phe Leu Val Met Cys Thr Leu Phe Val Leu Ala Val Leu Leu
                           770                 775                 780
           Pro Val Leu Phe Leu Leu Tyr Arg His Arg Asn Ser Met Lys Val Phe
           785                 790                 795                 800
           Leu Lys Gln Gly Glu Cys Ala Ser Val His Pro Lys Thr Cys Pro Val
                           805                 810                 815
           Val Leu Pro Pro Glu Thr Arg Pro Arg Phe His Arg His Arg Arg Arg
                           820                 825                 830
           Arg Gly Asp Ser Thr Ala
                   835

<210> SEQ ID NO 9
<211> LENGTH: 3453
<212> TYPE: DNA
<213> ORGANISM: homo sapiens

<400> SEQUENCE: 9
atgcccagcc agggcagggt ggagagctgc agctgcaggt ccggaggcgg gggcccccgg      60
ggcgactcgg gggcggaccg cggggcggag ctgccgcccg tgagtccggc cgagccacct     120
gagcccgagc gcgcggacac cgtcgctcct gctctccgaa tgctgcgcac cgcgatgggc     180
ctgaggagct ggctcgccgc cccatggggc gcgctgccgc tcggccaccg ctgctgctg     240 ctcctgctgc tgctgctcct gctgcagccg ccgcctccga cctgggcgct cagccccgg     300 atcagcctgc ctctgggctc tgaagagcgg ccattcctca gattcgaagc tgaacacatc     360
tccaactaca cagcccttct gctgagcagg gatggcagga ccctgtacgt gggtgctcga     420
gaggccctct ttgcactcag tagcaacctc agcttcctgc aggcggggga gtaccaggag     480
```

-continued

```
ctgctttggg gtgcagacgc agagaagaaa cagcagtgca gcttcaaggg caaggaccca     540
cagcgcgact gtcaaaacta catcaagatc ctcctgccgc tcagcggcag tcacctgttc     600
acctgtggca cagcagcctt cagccccatg tgtacctaca tcaacatgga gaacttcacc     660
ctggcaaggg acgagaaggg gaatgtcctc ctggaagatg caagggccg ttgtcccttc     720 gacccgaatt tcaagtccac tgccctggtg gttgatggcg agctctacac tggaacagtc     780
agcagcttcc aagggaatga cccggccatc tcgcggagcc aaagccttcg ccccaccaag     840
accgagagct ccctcaactg gctgcaagac ccagcttttg tggcctcagc ctacattcct     900
gagagcctgg gcagcttgca aggcgatgat gacaagatct acttttttctt cagcgagact    960 ggccaggaat ttgagttctt tgagaacacc attgtgtccc gcattgcccg catctgcaag    1020
ggcgatgagg gtggagagcg ggtgctacag cagcgctgga cctccttcct caaggcccag    1080
ctgctgtgct cacggcccga cgatggcttc cccttcaacg tgctgcagga tgtcttcacg    1140
ctgagcccca gccccagga ctggcgtgac acccttttct atggggtctt cacttcccag     1200
tggcacaggg gaactacaga aggctctgcc gtctgtgtct tcacaatgaa ggatgtgcag    1260
agagtcttca gcggcctcta caaggaggtg aaccgtgaga cacagcagtg gtacaccgtg    1320
acccacccgg tgcccacacc ccggcctgga gcgtgcatca ccaacagtgc ccgggaaagg    1380
aagatcaact catccctgca gctcccagac gcgtgctga acttcctcaa ggaccacttc     1440
ctgatggacg ggcaggtccg aagccgcatg ctgctgctgc agcccaggc tcgctaccag    1500 cgcgtggctg tacaccgcgt ccctggcctg caccacacct cgatgtcct cttcctgggc    1560 actggtgacg gccggctcca aaggcagtg agcgtgggcc ccggggtgca catcattgag    1620
gagctgcaga tcttctcatc gggacagccc gtgcagaatc tgctcctgga cacccacagg    1680
gggctgctgt atgcggcctc acactcgggc gtagtccagg tgcccatggc caactgcagc    1740
ctgtacagga gctgtgggga ctgcctcctc gcccgggacc cctactgtgc ttggagcggc    1800
tccagctgca gcacgtcag cctctaccag cctcagctgg ccaccaggcc gtggatccag    1860
gacatcgagg gagccagcgc caaggacctt tgcagcgcgt cttcggttgt gtccccgtct    1920
tttgtaccaa caggggagaa gccatgtgag caagtccagt tccagcccaa cacagtgaac    1980
actttggcct gccgctcct ctccaacctg gcgaccgac tctggctacg caacggggcc     2040
cccgtcaatg cctcggcctc ctgccacgtg ctacccactg gggacctgct gctggtgggc    2100
acccaacagc tggggagtt ccagtgctgg tcactagagg agggcttcca gcagctggta    2160
gccagctact gcccagaggt ggtggaggac ggggtggcag accaaacaga tacggtgccc    2220
acaccccggc ctggagcgtg catcaccaac agtgcccggg aaaggaagat caactcatcc    2280
ctgcagctcc cagaccgcgt gctgaacttc ctcaaggacc acttcctgat ggacgggcag    2340
gtccgaagcc gcatgctgct gctgcagccc aggctcgct accagcgcgt ggctgtacac    2400
cgcgtccctg gcctgcacca cacctacgat gtcctcttcc tgggcactgg tgacggccgg    2460
ctccacaagg cagtgagcgt gggccccggg tgcacatca ttgaggagct gcagatcttc    2520
tcatcgggac agcccgtgca gaatctgctc ctggacaccc acaggggct gctgtatgcg    2580 gcctcacact cggcgtagt ccaggtgccc atgccaact gcagcctgta caggagctgt    2640
ggggactgcc tcctcgcccg ggacccctac tgtgcttgga gcggctccag ctgcaagcac    2700
gtcagcctct accagcctca gctggccacc aggccgtgga tccaggacat cgagggagcc    2760
agcgccaagg acctttgcag cgcgtcttcg gttgtgtccc cgtctttgt accaacaggg    2820
```

-continued

```
gagaagccat gtgagcaagt ccagttccag cccaacacag tgaacacttt ggcctgcccg    2880
ctcctctcca acctggcgac ccgactctgg ctacgcaacg ggcccccgt caatgcctcg     2940 gcctcctgcc acgtgctacc cactggggac ctgctgctgg tgggcaccca acagctgggg    3000
gagttccagt gctggtcact agaggagggc ttccagcagc tggtagccag ctactgccca    3060
gaggtggtgg aggacggggt ggcaaaccaa acagatgagg gtggcagtgt acccgtcatt    3120
atcagcacat cgcgtgtgag tgcaccagct ggtggcaagg ccagctgggg tgcagacagg    3180
tcctactgga aggagttcct ggtgatgtgc acgctctttg tgctggccgt gctgctccca    3240
gttttattct tgctctaccg gcaccggaac agcatgaaag tcttcctgaa gcagggggaa    3300
tgtgccagcg tgcaccccaa gacctgccct gtggtgctgc ccctgagac ccgccctcgg     3360 tttcaccgtc accgccgacg tcgaggtgcc cgaaggaccg cgcacctggt gcatgacccg    3420
caagcccggt gcctgaagcg gatccagaca tga                                 3453
```

<210> SEQ ID NO 10
<211> LENGTH: 1150
<212> TYPE: PRT
<213> ORGANISM: homo sapiens

<400> SEQUENCE: 10

```
Met Pro Ser Gln Gly Arg Val Glu Ser Cys Ser Cys Arg Ser Gly Gly
 1               5                   10                  15

Gly Gly Pro Arg Gly Asp Ser Gly Ala Asp Arg Gly Ala Glu Leu Pro
            20                  25                  30

Pro Val Ser Pro Ala Glu Pro Glu Pro Glu Pro Arg Asp Thr Val
         35                  40                  45

Ala Pro Ala Leu Arg Met Leu Arg Thr Ala Met Gly Leu Arg Ser Trp
     50                  55                  60

Leu Ala Ala Pro Trp Gly Ala Leu Pro Pro Arg Pro Leu Leu Leu
 65                  70                  75                  80

Leu Leu Leu Leu Leu Leu Leu Gln Pro Pro Pro Thr Trp Ala
                 85                  90                  95

Leu Ser Pro Arg Ile Ser Leu Pro Leu Gly Ser Glu Glu Arg Pro Phe
            100                 105                 110

Leu Arg Phe Glu Ala Glu His Ile Ser Asn Tyr Thr Ala Leu Leu Leu
        115                 120                 125

Ser Arg Asp Gly Arg Thr Leu Tyr Val Gly Ala Arg Glu Ala Leu Phe
    130                 135                 140

Ala Leu Ser Ser Asn Leu Ser Phe Leu Pro Gly Gly Glu Tyr Gln Glu
145                 150                 155                 160

Leu Leu Trp Gly Ala Asp Ala Glu Lys Lys Gln Gln Cys Ser Phe Lys
                165                 170                 175

Gly Lys Asp Pro Gln Arg Asp Cys Gln Asn Tyr Ile Lys Ile Leu Leu
            180                 185                 190

Pro Leu Ser Gly Ser His Leu Phe Thr Cys Gly Thr Ala Ala Phe Ser
        195                 200                 205

Pro Met Cys Thr Tyr Ile Asn Met Glu Asn Phe Thr Leu Ala Arg Asp
    210                 215                 220

Glu Lys Gly Asn Val Leu Leu Glu Asp Gly Lys Gly Arg Cys Pro Phe
225                 230                 235                 240

Asp Pro Asn Phe Lys Ser Thr Ala Leu Val Val Asp Gly Glu Leu Tyr
                245                 250                 255

Thr Gly Thr Val Ser Ser Phe Gln Gly Asn Asp Pro Ala Ile Ser Arg
```

```
                260                 265                 270
Ser Gln Ser Leu Arg Pro Thr Lys Thr Glu Ser Ser Leu Asn Trp Leu
            275                 280                 285
Gln Asp Pro Ala Phe Val Ala Ser Ala Tyr Ile Pro Glu Ser Leu Gly
        290                 295                 300
Ser Leu Gln Gly Asp Asp Lys Ile Tyr Phe Phe Ser Glu Thr
305                 310                 315                 320
Gly Gln Glu Phe Glu Phe Glu Asn Thr Ile Val Ser Arg Ile Ala
                325                 330                 335
Arg Ile Cys Lys Gly Asp Glu Gly Glu Arg Val Leu Gln Gln Arg
            340                 345                 350
Trp Thr Ser Phe Leu Lys Ala Gln Leu Leu Cys Ser Arg Pro Asp Asp
                355                 360                 365
Gly Phe Pro Phe Asn Val Leu Gln Asp Val Phe Thr Leu Ser Pro Ser
        370                 375                 380
Pro Gln Asp Trp Arg Asp Thr Leu Phe Tyr Gly Val Phe Thr Ser Gln
385                 390                 395                 400
Trp His Arg Gly Thr Thr Glu Gly Ser Ala Val Cys Val Phe Thr Met
                405                 410                 415
Lys Asp Val Gln Arg Val Phe Ser Gly Leu Tyr Lys Glu Val Asn Arg
            420                 425                 430
Glu Thr Gln Gln Trp Tyr Thr Val Thr His Pro Val Pro Thr Pro Arg
        435                 440                 445
Pro Gly Ala Cys Ile Thr Asn Ser Ala Arg Glu Arg Lys Ile Asn Ser
            450                 455                 460
Ser Leu Gln Leu Pro Asp Arg Val Leu Asn Phe Leu Lys Asp His Phe
465                 470                 475                 480
Leu Met Asp Gly Gln Val Arg Ser Arg Met Leu Leu Gln Pro Gln
                485                 490                 495
Ala Arg Tyr Gln Arg Val Ala Val His Arg Val Pro Gly Leu His His
            500                 505                 510
Thr Tyr Asp Val Leu Phe Leu Gly Thr Gly Asp Gly Arg Leu His Lys
        515                 520                 525
Ala Val Ser Val Gly Pro Arg Val His Ile Ile Glu Glu Leu Gln Ile
        530                 535                 540
Phe Ser Ser Gly Gln Pro Val Gln Asn Leu Leu Leu Asp Thr His Arg
545                 550                 555                 560
Gly Leu Leu Tyr Ala Ala Ser His Ser Gly Val Val Gln Val Pro Met
                565                 570                 575
Ala Asn Cys Ser Leu Tyr Arg Ser Cys Gly Asp Cys Leu Leu Ala Arg
            580                 585                 590
Asp Pro Tyr Cys Ala Trp Ser Gly Ser Cys Lys His Val Ser Leu
        595                 600                 605
Tyr Gln Pro Gln Leu Ala Thr Arg Pro Trp Ile Gln Asp Ile Glu Gly
        610                 615                 620
Ala Ser Ala Lys Asp Leu Cys Ser Ala Ser Val Val Ser Pro Ser
625                 630                 635                 640
Phe Val Pro Thr Gly Glu Lys Pro Cys Glu Gln Val Gln Phe Gln Pro
                645                 650                 655
Asn Thr Val Asn Thr Leu Ala Cys Pro Leu Leu Ser Asn Leu Ala Thr
            660                 665                 670
Arg Leu Trp Leu Arg Asn Gly Ala Pro Val Asn Ala Ser Ala Ser Cys
            675                 680                 685
```

```
His Val Leu Pro Thr Gly Asp Leu Leu Leu Val Gly Thr Gln Gln Leu
    690             695             700
Gly Glu Phe Gln Cys Trp Ser Leu Glu Glu Gly Phe Gln Gln Leu Val
705             710             715             720
Ala Ser Tyr Cys Pro Glu Val Val Glu Asp Gly Val Ala Asp Gln Thr
            725             730             735
Asp Thr Val Pro Thr Pro Arg Pro Gly Ala Cys Ile Thr Asn Ser Ala
        740             745             750
Arg Glu Arg Lys Ile Asn Ser Ser Leu Gln Leu Pro Asp Arg Val Leu
    755             760             765
Asn Phe Leu Lys Asp His Phe Leu Met Asp Gly Gln Val Arg Ser Arg
770             775             780
Met Leu Leu Leu Gln Pro Gln Ala Arg Tyr Gln Arg Val Ala Val His
785             790             795             800
Arg Val Pro Gly Leu His His Thr Tyr Asp Val Leu Phe Leu Gly Thr
            805             810             815
Gly Asp Gly Arg Leu His Lys Ala Val Ser Val Gly Pro Arg Val His
        820             825             830
Ile Ile Glu Glu Leu Gln Ile Phe Ser Ser Gly Gln Pro Val Gln Asn
    835             840             845
Leu Leu Leu Asp Thr His Arg Gly Leu Leu Tyr Ala Ala Ser His Ser
850             855             860
Gly Val Val Gln Val Pro Met Ala Asn Cys Ser Leu Tyr Arg Ser Cys
865             870             875             880
Gly Asp Cys Leu Leu Ala Arg Asp Pro Tyr Cys Ala Trp Ser Gly Ser
            885             890             895
Ser Cys Lys His Val Ser Leu Tyr Gln Pro Gln Leu Ala Thr Arg Pro
        900             905             910
Trp Ile Gln Asp Ile Glu Gly Ala Ser Ala Lys Asp Leu Cys Ser Ala
    915             920             925
Ser Ser Val Val Ser Pro Ser Phe Val Pro Thr Gly Glu Lys Pro Cys
930             935             940
Glu Gln Val Gln Phe Gln Pro Asn Thr Val Asn Thr Leu Ala Cys Pro
945             950             955             960
Leu Leu Ser Asn Leu Ala Thr Arg Leu Trp Leu Arg Asn Gly Ala Pro
            965             970             975
Val Asn Ala Ser Ala Ser Cys His Val Leu Pro Thr Gly Asp Leu Leu
        980             985             990
Leu Val Gly Thr Gln Gln Leu Gly Glu Phe Gln Cys Trp Ser Leu Glu
    995             1000            1005
Glu Gly Phe Gln Gln Leu Val Ala Ser Tyr Cys Pro Glu Val Val Glu
    1010            1015            1020
Asp Gly Val Ala Asn Gln Thr Asp Glu Gly Gly Ser Val Pro Val Ile
1025            1030            1035            1040
Ile Ser Thr Ser Arg Val Ser Ala Pro Ala Gly Gly Lys Ala Ser Trp
            1045            1050            1055
Gly Ala Asp Arg Ser Tyr Trp Lys Glu Phe Leu Val Met Cys Thr Leu
        1060            1065            1070
Phe Val Leu Ala Val Leu Leu Pro Val Leu Phe Leu Leu Tyr Arg His
    1075            1080            1085
Arg Asn Ser Met Lys Val Phe Leu Lys Gln Gly Glu Cys Ala Ser Val
    1090            1095            1100
```

His Pro Lys Thr Cys Pro Val Leu Pro Pro Glu Thr Arg Pro Arg
1105                1110                1115                1120

Phe His Arg His Arg Arg Arg Gly Ala Arg Thr Ala His Leu
            1125                1130                1135

Val His Asp Pro Gln Ala Arg Cys Leu Lys Arg Ile Gln Thr
        1140                1145                1150

<210> SEQ ID NO 11
<211> LENGTH: 2592
<212> TYPE: DNA
<213> ORGANISM: homo sapiens

<400> SEQUENCE: 11

| | | | | | |
|---|---|---|---|---|---|
| atgcccagcc | agggcagggt | ggagagctgc | agctgcaggt | ccggaggcgg | gggcccccgg | 60 |
| ggcgactcgg | gggcggaccg | cggggcggag | ctgccgcccg | tgagtccggc | cgagccacct | 120 |
| gagcccgagc | cgcgggacac | cgtcgctcct | gctctccgaa | tgctgcgcac | cgcgatgggc | 180 |
| ctgaggagct | ggctcgccgc | cccatggggc | gcgctgccgc | ctcggccacc | gctgctgctg | 240 |
| ctcctgctgc | tgctgctcct | gctgcagccg | ccgcctccga | cctgggcgct | cagccccgg | 300 |
| atcagcctgc | ctctgggctc | tgaagagcgg | ccattcctca | gattcgaagc | tgaacacatc | 360 |
| tccaactaca | cagcccttct | gctgagcagg | gatggcagga | ccctgtacgt | gggtgctcga | 420 |
| gaggccctct | ttgcactcag | tagcaacctc | agcttcctgc | aggcggggga | gtaccaggag | 480 |
| ctgctttggg | gtgcagacgc | agagaagaaa | cagcagtgca | gcttcaaggg | caaggaccca | 540 |
| cagcgcgact | gtcaaaacta | catcaagatc | ctcctgccgc | tcagcggcag | tcacctgttc | 600 |
| acctgtggca | cagcagcctt | cagccccatg | tgtacctaca | tcaacatgga | gaacttcacc | 660 |
| ctggcaaggg | acgagaaggg | gaatgtcctc | ctggaagatg | gcaagggccg | ttgtccctc | 720 |
| gacccgaatt | tcaagtccac | tgccctggtg | gttgatggcg | agctctacac | tggaacagtc | 780 |
| agcagcttcc | aagggaatga | cccggccatc | tcgcggagcc | aaagccttcg | ccccaccaag | 840 |
| accgagagct | ccctcaactg | gctgcaagac | ccagcttttg | tggcctcagc | ctacattcct | 900 |
| gagagcctgg | gcagcttgca | aggcgatgat | gacaagatct | acttttctt | cagcgagact | 960 |
| ggccaggaat | ttgagttctt | tgagaacacc | attgtgtccc | gcattgcccg | catctgcaag | 1020 |
| ggcgatgagg | tggagagcg | ggtgctacag | cagcgctgga | cctccttcct | caaggcccag | 1080 |
| ctgctgtgct | cacggcccga | cgatggcttc | cccttcaacg | tgctgcagga | tgtcttcacg | 1140 |
| ctgagcccca | gccccagga | ctggcgtgac | accctttct | atggggtctt | cacttcccag | 1200 |
| tggcacaggg | gaactacaga | aggctctgcc | gtctgtgtct | tcacaatgaa | ggatgtgcag | 1260 |
| agagtcttca | gcggcctcta | caaggaggtg | aaccgtgaga | cacagcagtg | gtacaccgtg | 1320 |
| acccacccgg | tgcccacacc | ccggcctgga | gcgtgcatca | ccaacagtgc | ccgggaaagg | 1380 |
| aagatcaact | catccctgca | gctcccagac | cgcgtgctga | acttcctcaa | ggaccacttc | 1440 |
| ctgatggacg | ggcaggtccg | aagccgcatg | ctgctgctgc | agcccaggc | tcgctaccag | 1500 |
| cgcgtggctg | tacaccgcgt | ccctggcctg | caccacacct | acgatgtcct | cttcctgggc | 1560 |
| actggtgacg | gccggctcca | caaggcagtg | agcgtgggcc | ccgggtgca | catcattgag | 1620 |
| gagctgcaga | tcttctcatc | gggacagccc | gtgcagaatc | tgctcctgga | cacccacagg | 1680 |
| gggctgctgt | atcggccctc | acactcgggc | gtagtccagg | tgcccatggc | caactgcagc | 1740 |
| ctgtacagga | gctgtgggga | ctgcctcctc | gcccgggacc | ctactgtgc | ttggagcggc | 1800 |
| tccagctgca | agcacgtcag | cctctaccag | cctcagctgc | ccaccaggcc | gtggatccag | 1860 |

```
gacatcgagg gagccagcgc caaggacctt tgcagcgcgt cttcggttgt gtcccgtct   1920 tttgtaccaa caggggagaa gccatgtgag caagtccagt tccagcccaa cacagtgaac   1980
actttggcct gcccgctcct ctccaacctg gcgacccgac tctggctacg caacggggcc   2040
cccgtcaatg cctcggcctc ctgccacgtg ctacccactg gggacctgct gctggtgggc   2100
acccaacagc tgggggagtt ccagtgctgg tcactagagg agggcttcca gcagctggta   2160
gccagctact gcccagaggt ggtggaggac ggggtggcag accaaacaga tgaggtggc    2220 agtgtacccg tcattatcag cacatcgcgt gtgagtgcac cagctggtgg caaggccagc   2280
tggggtgcag acaggtccta ctggaaggag ttcctggtga tgtgcacgct ctttgtgctg   2340
gccgtgctgc tcccagtttt attcttgctc taccggcacc ggaacagcat gaaagtcttc   2400
ctgaagcagg gggaatgtgc cagcgtgcac cccaagacct gccctgtggt gctgccccct   2460
gagacccgcc cactcaacgg cctagggccc ctagcaccc cgctcgatca ccgagggtac    2520
cagtcccccc gaaggaccgc gcacctggtg catgacccgc aagcccggtg cctgaagcgg   2580
atccagacat ga                                                      2592
```

<210> SEQ ID NO 12
<211> LENGTH: 863
<212> TYPE: PRT
<213> ORGANISM: homo sapiens

<400> SEQUENCE: 12

```
Met Pro Ser Gln Gly Arg Val Glu Ser Cys Ser Cys Arg Ser Gly Gly
 1               5                  10                  15

Gly Gly Pro Arg Gly Asp Ser Gly Ala Asp Arg Gly Ala Glu Leu Pro
            20                  25                  30

Pro Val Ser Pro Ala Glu Pro Glu Pro Glu Pro Arg Asp Thr Val
        35                  40                  45

Ala Pro Ala Leu Arg Met Leu Arg Thr Ala Met Gly Leu Arg Ser Trp
    50                  55                  60

Leu Ala Ala Pro Trp Gly Ala Leu Pro Pro Arg Pro Leu Leu Leu
65                  70                  75                  80

Leu Leu Leu Leu Leu Leu Leu Gln Pro Pro Pro Thr Trp Ala
                85                  90                  95

Leu Ser Pro Arg Ile Ser Leu Pro Leu Gly Ser Glu Glu Arg Pro Phe
            100                 105                 110

Leu Arg Phe Glu Ala Glu His Ile Ser Asn Tyr Thr Ala Leu Leu Leu
        115                 120                 125

Ser Arg Asp Gly Arg Thr Leu Tyr Val Gly Ala Arg Glu Ala Leu Phe
    130                 135                 140

Ala Leu Ser Ser Asn Leu Ser Phe Leu Pro Gly Gly Glu Tyr Gln Glu
145                 150                 155                 160

Leu Leu Trp Gly Ala Asp Ala Glu Lys Lys Gln Gln Cys Ser Phe Lys
                165                 170                 175

Gly Lys Asp Pro Gln Arg Asp Cys Gln Asn Tyr Ile Lys Ile Leu Leu
            180                 185                 190

Pro Leu Ser Gly Ser His Leu Phe Thr Cys Gly Thr Ala Ala Phe Ser
        195                 200                 205

Pro Met Cys Thr Tyr Ile Asn Met Glu Asn Phe Thr Leu Ala Arg Asp
    210                 215                 220

Glu Lys Gly Asn Val Leu Leu Glu Asp Gly Lys Gly Arg Cys Pro Phe
225                 230                 235                 240
```

-continued

Asp Pro Asn Phe Lys Ser Thr Ala Leu Val Asp Gly Glu Leu Tyr
            245                 250                 255

Thr Gly Thr Val Ser Ser Phe Gln Gly Asn Asp Pro Ala Ile Ser Arg
                260                 265                 270

Ser Gln Ser Leu Arg Pro Thr Lys Thr Glu Ser Ser Leu Asn Trp Leu
            275                 280                 285

Gln Asp Pro Ala Phe Val Ala Ser Ala Tyr Ile Pro Glu Ser Leu Gly
    290                 295                 300

Ser Leu Gln Gly Asp Asp Lys Ile Tyr Phe Phe Ser Glu Thr
305                 310                 315                 320

Gly Gln Glu Phe Glu Phe Glu Asn Thr Ile Val Ser Arg Ile Ala
                325                 330                 335

Arg Ile Cys Lys Gly Asp Glu Gly Glu Arg Val Leu Gln Gln Arg
            340                 345                 350

Trp Thr Ser Phe Leu Lys Ala Gln Leu Leu Cys Ser Arg Pro Asp Asp
                355                 360                 365

Gly Phe Pro Phe Asn Val Leu Gln Asp Val Phe Thr Leu Ser Pro Ser
    370                 375                 380

Pro Gln Asp Trp Arg Asp Thr Leu Phe Tyr Gly Val Phe Thr Ser Gln
385                 390                 395                 400

Trp His Arg Gly Thr Thr Glu Gly Ser Ala Val Cys Val Phe Thr Met
                405                 410                 415

Lys Asp Val Gln Arg Val Phe Ser Gly Leu Tyr Lys Glu Val Asn Arg
            420                 425                 430

Glu Thr Gln Gln Trp Tyr Thr Val Thr His Pro Val Pro Thr Pro Arg
    435                 440                 445

Pro Gly Ala Cys Ile Thr Asn Ser Ala Arg Glu Arg Lys Ile Asn Ser
450                 455                 460

Ser Leu Gln Leu Pro Asp Arg Val Leu Asn Phe Leu Lys Asp His Phe
465                 470                 475                 480

Leu Met Asp Gly Gln Val Arg Ser Arg Met Leu Leu Gln Pro Gln
                485                 490                 495

Ala Arg Tyr Gln Arg Val Ala Val His Arg Val Pro Gly Leu His His
            500                 505                 510

Thr Tyr Asp Val Leu Phe Leu Gly Thr Gly Asp Gly Arg Leu His Lys
    515                 520                 525

Ala Val Ser Val Gly Pro Arg Val His Ile Ile Glu Glu Leu Gln Ile
530                 535                 540

Phe Ser Ser Gly Gln Pro Val Gln Asn Leu Leu Leu Asp Thr His Arg
545                 550                 555                 560

Gly Leu Leu Tyr Ala Ala Ser His Ser Gly Val Val Gln Val Pro Met
                565                 570                 575

Ala Asn Cys Ser Leu Tyr Arg Ser Cys Gly Asp Cys Leu Leu Ala Arg
            580                 585                 590

Asp Pro Tyr Cys Ala Trp Ser Gly Ser Cys Lys His Val Ser Leu
    595                 600                 605

Tyr Gln Pro Gln Leu Ala Thr Arg Pro Trp Ile Gln Asp Ile Glu Gly
    610                 615                 620

Ala Ser Ala Lys Asp Leu Cys Ser Ala Ser Val Ser Pro Ser
625                 630                 635                 640

Phe Val Pro Thr Gly Glu Lys Pro Cys Glu Gln Val Gln Phe Gln Pro
                645                 650                 655

Asn Thr Val Asn Thr Leu Ala Cys Pro Leu Leu Ser Asn Leu Ala Thr

-continued

```
                  660             665             670
Arg Leu Trp Leu Arg Asn Gly Ala Pro Val Asn Ala Ser Ala Ser Cys
                675             680             685

His Val Leu Pro Thr Gly Asp Leu Leu Leu Val Gly Thr Gln Gln Leu
            690             695             700

Gly Glu Phe Gln Cys Trp Ser Leu Glu Glu Gly Phe Gln Gln Leu Val
705             710             715             720

Ala Ser Tyr Cys Pro Glu Val Val Glu Asp Gly Val Ala Asp Gln Thr
                725             730             735

Asp Glu Gly Gly Ser Val Pro Val Ile Ile Ser Thr Ser Arg Val Ser
            740             745             750

Ala Pro Ala Gly Gly Lys Ala Ser Trp Gly Ala Asp Arg Ser Tyr Trp
            755             760             765

Lys Glu Phe Leu Val Met Cys Thr Leu Phe Val Leu Ala Val Leu Leu
770             775             780

Pro Val Leu Phe Leu Leu Tyr Arg His Arg Asn Ser Met Lys Val Phe
785             790             795             800

Leu Lys Gln Gly Glu Cys Ala Ser Val His Pro Lys Thr Cys Pro Val
                805             810             815

Val Leu Pro Pro Glu Thr Arg Pro Leu Asn Gly Leu Gly Pro Pro Ser
            820             825             830

Thr Pro Leu Asp His Arg Gly Tyr Gln Ser Pro Arg Arg Thr Ala His
            835             840             845

Leu Val His Asp Pro Gln Ala Arg Cys Leu Lys Arg Ile Gln Thr
            850             855             860
```

<210> SEQ ID NO 13
<211> LENGTH: 3477
<212> TYPE: DNA
<213> ORGANISM: homo sapiens

<400> SEQUENCE: 13

```
atgcccagcc agggcagggt ggagagctgc agctgcaggt ccggaggcgg gggcccccgg    60
ggcgactcgg gggcggaccg cggggcggag ctgccgcccg tgagtccggc cgagccacct   120
gagcccgagc cgcgggacac cgtcgctcct gctctccgaa tgctgcgcac cgcgatgggc   180
ctgaggagct ggctcgccgc cccatggggc gcgctgccgc ctcggccacc gctgctgctg   240
ctcctgctgc tgctgctcct gctgcagccg ccgcctccga cctgggcgct cagccccggg   300
atcagcctgc tctgggctc tgaagagcgg ccattcctca gattcgaagc tgaacacatc   360
tccaactaca cagcccttct gctgagcagg gatggcagga ccctgtacgt gggtgctcga   420
gaggccctct ttgcactcag tagcaacctc agcttcctgc aggcggggga gtaccaggag   480
ctgctttggg gtgcagacgc agagaagaaa cagcagtgca gcttcaaggg caaggaccca   540
cagcgcgact gtcaaaacta catcaagatc ctcctgccgc tcagcggcag tcacctgttc   600
acctgtggca gcagccttt cagccccatg tgtacctaca tcaacatgga aacttcacc   660
ctggcaaggg acgagaaggg gaatgtcctc tggaagatg caagggccg ttgtcccttc   720
gacccgaatt tcaagtccac tgccctggtg ttgatggcg agctctacac tggaacagtc   780
agcagcttcc aagggaatga cccggccatc tcgcggagcc aaagccttcg ccccaccaag   840
accgagagct ccctcaactg gctgcaagac ccagcttttg tggcctcagc ctacattcct   900
gagagcctgg gcagcttgca aggcgatgat gacaagatct actttttctt cagcgagact   960
ggccaggaat ttgagttctt tgagaacacc attgtgtccc gcattgcccg catctgcaag  1020
```

-continued

```
ggcgatgagg gtggagagcg ggtgctacag cagcgctgga cctccttcct caaggcccag    1080
ctgctgtgct cacggcccga cgatggcttc cccttcaacg tgctgcagga tgtcttcacg    1140
ctgagcccca gccccagga ctggcgtgac accctttct atgggtctt cacttcccag       1200 tggcacaggg gaactacaga aggctctgcc gtctgtgtct tcacaatgaa ggatgtgcag    1260
agagtcttca gcggcctcta caaggaggtg aaccgtgaga cacagcagtg gtacaccgtg    1320
acccacccgg tgcccacacc ccggcctgga gcgtgcatca ccaacagtgc ccgggaaagg    1380
aagatcaact catccctgca gctcccagac cgcgtgctga acttcctcaa ggaccacttc    1440
ctgatggacg ggcaggtccg aagccgcatg ctgctgctgc agccccaggc tcgctaccag    1500
cgcgtggctg tacaccgcgt ccctggcctg caccacacct acgatgtcct cttcctgggc    1560
actggtgacg gccggctcca caaggcagtg agcgtgggcc cccgggtgca catcattgag    1620
gagctgcaga tcttctcatc gggacagccc gtgcagaatc tgctcctgga cacccacagg    1680
gggctgctgt atgcggcctc acactcgggc gtagtccagg tgcccatggc caactgcagc    1740
ctgtacagga gctgtgggga ctgcctcctc gcccgggacc cctactgtgc ttggagcggc    1800
tccagctgca agcacgtcag cctctaccag cctcagctgg ccaccaggcc gtggatccag    1860
gacatcgagg gagccagcgc caaggaccctt tgcagcgcgt cttcggttgt gtccccgtct    1920
tttgtaccaa cagggggagaa gccatgtgag caagtccagt tccagcccaa cacagtgaac    1980
actttggcct gcccgctcct ctccaacctg gcgacccgac tctggctacg caacggggcc    2040
cccgtcaatg cctcggcctc ctgccacgtg ctacccactg gggacctgct gctggtgggc    2100
acccaacagc tgggggagtt ccagtgctgg tcactagagg agggcttcca gcagctggta    2160
gccagctact gcccagaggt ggtggaggac ggggtggcag accaaacaga tacggtgccc    2220 acacccggc ctggagcgtg catcaccaac agtgcccggg aaaggaagat caactcatcc     2280
ctgcagctcc cagaccgcgt gctgaacttc ctcaaggacc acttcctgat ggacgggcag    2340
gtccgaagcc gcatgctgct gctgcagccc caggctcgct accagcgcgt ggctgtacac    2400
cgcgtccctg gcctgcacca cacctacgat gtcctcttcc tgggcactgg tgacggccgg    2460
ctccacaagg cagtgagcgt gggcccccgg gtgcacatca ttgaggagct gcagatcttc    2520
tcatcgggac agcccgtgca gaatctgctc ctggacaccc acaggggggct gctgtatgcg    2580 gcctcacact cgggcgtagt ccaggtgccc atggccaact gcagcctgta caggagctgt    2640
ggggactgcc tcctcgcccg ggaccccta c tgtgcttgga gcggctccag ctgcaagcac    2700
gtcagcctct accagcctca gctggccacc aggccgtgga tccaggacat cgagggagcc    2760
agcgccaagg acctttgcag cgcgtcttcg gttgtgtccc cgtcttttgt accaacaggg    2820
gagaagccat gtgagcaagt ccagttccag cccaacacag tgaacacttt ggcctgcccg    2880
ctcctctcca acctggcgac ccgactctgg ctacgcaacg ggcccccgt caatgcctcg    2940 gcctcctgcc acgtgctacc cactggggac ctgctgctgg tgggcaccca acagctgggg    3000
gagttccagt gctggtcact agaggagggc ttccagcagc tggtagccag ctactgccca    3060
gaggtggtgg aggacggggt ggcaaaccaa acagatgagg gtggcagtgt accgtcatt    3120 atcagcacat cgcgtgtgag tgcaccagct ggtggcaagg ccagctgggg tgcagacagg    3180
tcctactgga aggagttcct ggtgatgtgc acgctctttg tgctggccgt gctgctccca    3240 gtttttattct tgctctaccg gcaccggaac agcatgaaag tcttcctgaa gcaggggaa    3300 tgtgccagcg tgcaccccaa gacctgccct gtggtgctgc cccctgagac ccgcccactc    3360
```

```
aacggcctag ggcccctag cacccgctc gatcaccgag ggtaccagtc ccccgaagg    3420 accgcgcacc tggtgcatga cccgcaagcc cggtgcctga agcggatcca gacatga     3477
```

<210> SEQ ID NO 14
<211> LENGTH: 1158
<212> TYPE: PRT
<213> ORGANISM: homo sapiens

<400> SEQUENCE: 14

```
Met Pro Ser Gln Gly Arg Val Glu Ser Cys Ser Cys Arg Ser Gly Gly
 1               5                  10                  15

Gly Gly Pro Arg Gly Asp Ser Gly Ala Asp Arg Gly Ala Glu Leu Pro
            20                  25                  30

Pro Val Ser Pro Ala Glu Pro Glu Pro Glu Pro Arg Asp Thr Val
        35                  40                  45

Ala Pro Ala Leu Arg Met Leu Arg Thr Ala Met Gly Leu Arg Ser Trp
 50                  55                  60

Leu Ala Ala Pro Trp Gly Ala Leu Pro Pro Arg Pro Pro Leu Leu Leu
 65                  70                  75                  80

Leu Leu Leu Leu Leu Leu Leu Gln Pro Pro Pro Thr Trp Ala
                85                  90                  95

Leu Ser Pro Arg Ile Ser Leu Pro Leu Gly Ser Glu Glu Arg Pro Phe
                100                 105                 110

Leu Arg Phe Glu Ala Glu His Ile Ser Asn Tyr Thr Ala Leu Leu Leu
            115                 120                 125

Ser Arg Asp Gly Arg Thr Leu Tyr Val Gly Ala Arg Glu Ala Leu Phe
130                 135                 140

Ala Leu Ser Ser Asn Leu Ser Phe Leu Pro Gly Gly Glu Tyr Gln Glu
145                 150                 155                 160

Leu Leu Trp Gly Ala Asp Ala Glu Lys Lys Gln Gln Cys Ser Phe Lys
                165                 170                 175

Gly Lys Asp Pro Gln Arg Asp Cys Gln Asn Tyr Ile Lys Ile Leu Leu
            180                 185                 190

Pro Leu Ser Gly Ser His Leu Phe Thr Cys Gly Thr Ala Ala Phe Ser
        195                 200                 205

Pro Met Cys Thr Tyr Ile Asn Met Glu Asn Phe Thr Leu Ala Arg Asp
 210                 215                 220

Glu Lys Gly Asn Val Leu Leu Glu Asp Gly Lys Gly Arg Cys Pro Phe
225                 230                 235                 240

Asp Pro Asn Phe Lys Ser Thr Ala Leu Val Val Asp Gly Glu Leu Tyr
                245                 250                 255

Thr Gly Thr Val Ser Ser Phe Gln Gly Asn Asp Pro Ala Ile Ser Arg
            260                 265                 270

Ser Gln Ser Leu Arg Pro Thr Lys Thr Glu Ser Ser Leu Asn Trp Leu
        275                 280                 285

Gln Asp Pro Ala Phe Val Ala Ser Ala Tyr Ile Pro Glu Ser Leu Gly
 290                 295                 300

Ser Leu Gln Gly Asp Asp Lys Ile Tyr Phe Phe Ser Glu Thr
305                 310                 315                 320

Gly Gln Glu Phe Glu Phe Phe Glu Asn Thr Ile Val Ser Arg Ile Ala
                325                 330                 335

Arg Ile Cys Lys Gly Asp Glu Gly Gly Glu Arg Val Leu Gln Gln Arg
            340                 345                 350

Trp Thr Ser Phe Leu Lys Ala Gln Leu Leu Cys Ser Arg Pro Asp Asp
```

```
                355                 360                 365
Gly Phe Pro Phe Asn Val Leu Gln Asp Val Phe Thr Leu Ser Pro Ser
    370                 375                 380
Pro Gln Asp Trp Arg Asp Thr Leu Phe Tyr Gly Val Phe Thr Ser Gln
385                 390                 395                 400
Trp His Arg Gly Thr Thr Glu Gly Ser Ala Val Cys Val Phe Thr Met
                405                 410                 415
Lys Asp Val Gln Arg Val Phe Ser Gly Leu Tyr Lys Glu Val Asn Arg
            420                 425                 430
Glu Thr Gln Gln Trp Tyr Thr Val Thr His Pro Val Pro Thr Pro Arg
        435                 440                 445
Pro Gly Ala Cys Ile Thr Asn Ser Ala Arg Glu Arg Lys Ile Asn Ser
    450                 455                 460
Ser Leu Gln Leu Pro Asp Arg Val Leu Asn Phe Leu Lys Asp His Phe
465                 470                 475                 480
Leu Met Asp Gly Gln Val Arg Ser Arg Met Leu Leu Leu Gln Pro Gln
                485                 490                 495
Ala Arg Tyr Gln Arg Val Ala Val His Arg Val Pro Gly Leu His His
            500                 505                 510
Thr Tyr Asp Val Leu Phe Leu Gly Thr Gly Asp Gly Arg Leu His Lys
        515                 520                 525
Ala Val Ser Val Gly Pro Arg Val His Ile Ile Glu Glu Leu Gln Ile
    530                 535                 540
Phe Ser Ser Gly Gln Pro Val Gln Asn Leu Leu Leu Asp Thr His Arg
545                 550                 555                 560
Gly Leu Leu Tyr Ala Ala Ser His Ser Gly Val Val Gln Val Pro Met
                565                 570                 575
Ala Asn Cys Ser Leu Tyr Arg Ser Cys Gly Asp Cys Leu Leu Ala Arg
            580                 585                 590
Asp Pro Tyr Cys Ala Trp Ser Gly Ser Cys Lys His Val Ser Leu
        595                 600                 605
Tyr Gln Pro Gln Leu Ala Thr Arg Pro Trp Ile Gln Asp Ile Glu Gly
    610                 615                 620
Ala Ser Ala Lys Asp Leu Cys Ser Ala Ser Val Val Ser Pro Ser
625                 630                 635                 640
Phe Val Pro Thr Gly Glu Lys Pro Cys Glu Gln Val Gln Phe Gln Pro
                645                 650                 655
Asn Thr Val Asn Thr Leu Ala Cys Pro Leu Leu Ser Asn Leu Ala Thr
            660                 665                 670
Arg Leu Trp Leu Arg Asn Gly Ala Pro Val Asn Ala Ser Ala Ser Cys
        675                 680                 685
His Val Leu Pro Thr Gly Asp Leu Leu Val Gly Thr Gln Gln Leu
    690                 695                 700
Gly Glu Phe Gln Cys Trp Ser Leu Glu Glu Gly Phe Gln Gln Leu Val
705                 710                 715                 720
Ala Ser Tyr Cys Pro Glu Val Val Glu Asp Gly Val Ala Asp Gln Thr
                725                 730                 735
Asp Thr Val Pro Thr Pro Arg Pro Gly Ala Cys Ile Thr Asn Ser Ala
            740                 745                 750
Arg Glu Arg Lys Ile Asn Ser Ser Leu Gln Leu Pro Asp Arg Val Leu
        755                 760                 765
Asn Phe Leu Lys Asp His Phe Leu Met Asp Gly Gln Val Arg Ser Arg
    770                 775                 780
```

```
Met Leu Leu Gln Pro Gln Ala Arg Tyr Gln Arg Val Ala Val His
785                 790                 795                 800

Arg Val Pro Gly Leu His His Thr Tyr Asp Val Leu Phe Leu Gly Thr
                805                 810                 815

Gly Asp Gly Arg Leu His Lys Ala Val Ser Val Gly Pro Arg Val His
                820                 825                 830

Ile Ile Glu Glu Leu Gln Ile Phe Ser Ser Gly Gln Pro Val Gln Asn
        835                 840                 845

Leu Leu Leu Asp Thr His Arg Gly Leu Leu Tyr Ala Ala Ser His Ser
    850                 855                 860

Gly Val Val Gln Val Pro Met Ala Asn Cys Ser Leu Tyr Arg Ser Cys
865                 870                 875                 880

Gly Asp Cys Leu Leu Ala Arg Asp Pro Tyr Cys Ala Trp Ser Gly Ser
                885                 890                 895

Ser Cys Lys His Val Ser Leu Tyr Gln Pro Gln Leu Ala Thr Arg Pro
            900                 905                 910

Trp Ile Gln Asp Ile Glu Gly Ala Ser Ala Lys Asp Leu Cys Ser Ala
        915                 920                 925

Ser Ser Val Val Ser Pro Ser Phe Val Pro Thr Gly Glu Lys Pro Cys
    930                 935                 940

Glu Gln Val Gln Phe Gln Pro Asn Thr Val Asn Thr Leu Ala Cys Pro
945                 950                 955                 960

Leu Leu Ser Asn Leu Ala Thr Arg Leu Trp Leu Arg Asn Gly Ala Pro
                965                 970                 975

Val Asn Ala Ser Ala Ser Cys His Val Leu Pro Thr Gly Asp Leu Leu
            980                 985                 990

Leu Val Gly Thr Gln Gln Leu Gly Glu Phe Gln Cys Trp Ser Leu Glu
        995                 1000                1005

Glu Gly Phe Gln Gln Leu Val Ala Ser Tyr Cys Pro Glu Val Val Glu
    1010                1015                1020

Asp Gly Val Ala Asn Gln Thr Asp Glu Gly Gly Ser Val Pro Val Ile
1025                1030                1035                1040

Ile Ser Thr Ser Arg Val Ser Ala Pro Ala Gly Gly Lys Ala Ser Trp
                1045                1050                1055

Gly Ala Asp Arg Ser Tyr Trp Lys Glu Phe Leu Val Met Cys Thr Leu
            1060                1065                1070

Phe Val Leu Ala Val Leu Leu Pro Val Leu Phe Leu Leu Tyr Arg His
        1075                1080                1085

Arg Asn Ser Met Lys Val Phe Leu Lys Gln Gly Glu Cys Ala Ser Val
    1090                1095                1100

His Pro Lys Thr Cys Pro Val Val Leu Pro Pro Glu Thr Arg Pro Leu
1105                1110                1115                1120

Asn Gly Leu Gly Pro Pro Ser Thr Pro Leu Asp His Arg Gly Tyr Gln
                1125                1130                1135

Ser Pro Arg Arg Thr Ala His Leu Val His Asp Pro Gln Ala Arg Cys
            1140                1145                1150

Leu Lys Arg Ile Gln Thr
        1155

<210> SEQ ID NO 15
<211> LENGTH: 2673
<212> TYPE: DNA
<213> ORGANISM: homo sapiens
```

<400> SEQUENCE: 15

```
atgcccagcc agggcagggt ggagagctgc agctgcaggt ccggaggcgg gggccccgg      60
ggcgactcgg gggcggaccg cggggcggag ctgccgcccg tgagtccggc cgagccacct    120
gagcccgagc cgcgggacac cgtcgctcct gctctccgaa tgctgcgcac cgcgatgggc    180
ctgaggagct ggctcgccgc ccatggggc gcgctgccgc ctcggccacc gctgctgctg     240
ctcctgctgc tgctgctcct gctgcagccg ccgcctccga cctgggcgct cagccccgg     300
atcagcctgc ctctgggctc tgaagagcgg ccattcctca gattcgaagc tgaacacatc    360
tccaactaca cagcccttct gctgagcagg gatggcagga ccctgtacgt gggtgctcga    420
gaggccctct ttgcactcag tagcaacctc agcttcctgc caggcgggga gtaccaggag    480
ctgctttggg gtgcagacgc agagaagaaa cagcagtgca gcttcaaggg caaggaccca    540
cagcgcgact gtcaaaacta catcaagatc ctcctgccgc tcagcggcag tcacctgttc    600
acctgtggca cagcagcctt cagccccatg tgtacctaca tcaacatgga gaacttcacc    660
ctggcaaggg acgagaaggg gaatgtcctc ctggaagatg gcaagggccg ttgtcccttc    720
gacccgaatt tcaagtccac tgccctggtg gttgatggcg agctctacac tggaacagtc    780
agcagcttcc aagggaatga cccggccatc tcgcggagcc aaagccttcg ccccaccaag    840
accgagagct ccctcaactg gctgcaagac ccagcttttg tggcctcagc ctacattcct    900
gagagcctgg gcagcttgca aggcgatgat gacaagatct acttttctt cagcgagact     960
ggccaggaat ttgagttctt tgagaacacc attgtgtccc gcattgcccg catctgcaag   1020
ggcgatgagg gtggagagcg ggtgctacag cagcgctgga cctccttcct caaggcccag   1080
ctgctgtgct cacggcccga cgatggcttc cccttcaacg tgctgcagga tgtcttcacg   1140
ctgagcccca gccccagga ctggcgtgac accctttct atggggtctt cacttcccag     1200
tggcacaggg gaactacaga aggctctgcc gtctgtgtct tcacaatgaa ggatgtgcag   1260
agagtcttca gcggcctcta caaggaggtg aaccgtgaga cacagcagtg gtacaccgtg   1320
acccaccgg tgcccacacc ccggcctgga gcgtgcatca ccaacagtgc ccgggaaagg    1380
aagatcaact catccctgca gctcccagac cgcgtgctga acttcctcaa ggaccacttc   1440
ctgatggacg ggcaggtccg aagccgcatg ctgctgctgc agcccaggc tcgctaccag    1500
cgcgtggctg tacaccgcgt ccctggcctg caccacacct acgatgtcct cttcctgggc   1560
actggtgacg gccggctcca aaggcagtg agcgtgggcc ccgggtgca catcattgag     1620
gagctgcaga tcttctcatc gggacagccc gtgcagaatc tgctcctgga cacccacagg   1680
gggctgctgt atgcggcctc acactcgggc gtagtccagg tgcccatggc caactgcagc   1740
ctgtacagga gctgtgggga ctgcctcctc gcccgggacc cctactgtgc ttggagcggc   1800
tccagctgca gcacgtcag cctctaccag cctcagctgg ccaccaggcc gtggatccag    1860
gacatcgagg agccagcgc caaggacctt tgcagcgcgt cttcggttgt gtccccgtct   1920
tttgtaccaa caggggagaa gccatgtgag caagtccagt tccagcccaa cacagtgaac   1980
actttggcct gccgctcct ctccaacctg gcgaccgac tctggctacg caacggggcc     2040
cccgtcaatg cctcggcctc ctgccacgtg ctacccactg ggacctgct gctggtgggc   2100
acccaacagc tggggagtt ccagtgctgg tcactagagg agggcttcca gcagctggta    2160
gccagctact gcccagaggt ggtggaggac ggggtggcag accaaacaga tgagggtggc   2220
agtgtacccg tcattatcag cacatcgcgt gtgagtgcac cagctggtgg caaggccagc    2280
tggggtgcag acaggtccta ctggaaggag ttcctggtga tgtgcacgct ctttgtgctg   2340
```

-continued

```
gccgtgctgc tcccagtttt attcttgctc taccggcacc ggaacagcat gaaagtcttc    2400
ctgaagcagg gggaatgtgc cagcgtgcac cccaagacct gccctgtggt gctgccccct    2460
gagacccgcc cactcaacgg cctagggccc cctagcaccc cgctcgatca ccgagggtac    2520
cagtccctgt cagacagccc cccggggggcc cgagtcttca ctgagtcaga aagaggcca    2580 ctcagcatcc aagacagctt cgtggaggta tccccagtgt gccccggcc ccgggtccgc    2640 cttggctcgg agatccgtga ctctgtggtg tga                                  2673
```

<210> SEQ ID NO 16
<211> LENGTH: 890
<212> TYPE: PRT
<213> ORGANISM: homo sapiens

<400> SEQUENCE: 16

```
Met Pro Ser Gln Gly Arg Val Glu Ser Cys Ser Cys Arg Ser Gly Gly
 1               5                  10                  15

Gly Gly Pro Arg Gly Asp Ser Gly Ala Asp Arg Gly Ala Glu Leu Pro
                20                  25                  30

Pro Val Ser Pro Ala Glu Pro Glu Pro Glu Pro Arg Asp Thr Val
            35                  40                  45

Ala Pro Ala Leu Arg Met Leu Arg Thr Ala Met Gly Leu Arg Ser Trp
 50                  55                  60

Leu Ala Ala Pro Trp Gly Ala Leu Pro Pro Arg Pro Pro Leu Leu Leu
 65                  70                  75                  80

Leu Leu Leu Leu Leu Leu Leu Gln Pro Pro Pro Thr Trp Ala
                85                  90                  95

Leu Ser Pro Arg Ile Ser Leu Pro Leu Gly Ser Glu Glu Arg Pro Phe
                100                 105                 110

Leu Arg Phe Glu Ala Glu His Ile Ser Asn Tyr Thr Ala Leu Leu Leu
            115                 120                 125

Ser Arg Asp Gly Arg Thr Leu Tyr Val Gly Ala Arg Glu Ala Leu Phe
 130                 135                 140

Ala Leu Ser Ser Asn Leu Ser Phe Leu Pro Gly Gly Glu Tyr Gln Glu
145                 150                 155                 160

Leu Leu Trp Gly Ala Asp Ala Glu Lys Lys Gln Gln Cys Ser Phe Lys
                165                 170                 175

Gly Lys Asp Pro Gln Arg Asp Cys Gln Asn Tyr Ile Lys Ile Leu Leu
            180                 185                 190

Pro Leu Ser Gly Ser His Leu Phe Thr Cys Gly Thr Ala Ala Phe Ser
 195                 200                 205

Pro Met Cys Thr Tyr Ile Asn Met Glu Asn Phe Thr Leu Ala Arg Asp
    210                 215                 220

Glu Lys Gly Asn Val Leu Leu Glu Asp Gly Lys Gly Arg Cys Pro Phe
225                 230                 235                 240

Asp Pro Asn Phe Lys Ser Thr Ala Leu Val Val Asp Gly Glu Leu Tyr
                245                 250                 255

Thr Gly Thr Val Ser Ser Phe Gln Gly Asn Asp Pro Ala Ile Ser Arg
            260                 265                 270

Ser Gln Ser Leu Arg Pro Thr Lys Thr Glu Ser Ser Leu Asn Trp Leu
        275                 280                 285

Gln Asp Pro Ala Phe Val Ala Ser Ala Tyr Ile Pro Glu Ser Leu Gly
    290                 295                 300

Ser Leu Gln Gly Asp Asp Asp Lys Ile Tyr Phe Phe Phe Ser Glu Thr
```

-continued

```
             305                 310                 315                 320
Gly Gln Glu Phe Glu Phe Phe Glu Asn Thr Ile Val Ser Arg Ile Ala
                 325                 330                 335

Arg Ile Cys Lys Gly Asp Glu Gly Gly Glu Arg Val Leu Gln Gln Arg
                 340                 345                 350

Trp Thr Ser Phe Leu Lys Ala Gln Leu Leu Cys Ser Arg Pro Asp Asp
                 355                 360                 365

Gly Phe Pro Phe Asn Val Leu Gln Asp Val Phe Thr Leu Ser Pro Ser
             370                 375                 380

Pro Gln Asp Trp Arg Asp Thr Leu Phe Tyr Gly Val Phe Thr Ser Gln
385                 390                 395                 400

Trp His Arg Gly Thr Thr Glu Gly Ser Ala Val Cys Val Phe Thr Met
                 405                 410                 415

Lys Asp Val Gln Arg Val Phe Ser Gly Leu Tyr Lys Glu Val Asn Arg
                 420                 425                 430

Glu Thr Gln Gln Trp Tyr Thr Val Thr His Pro Val Pro Thr Pro Arg
             435                 440                 445

Pro Gly Ala Cys Ile Thr Asn Ser Ala Arg Glu Arg Lys Ile Asn Ser
450                 455                 460

Ser Leu Gln Leu Pro Asp Arg Val Leu Asn Phe Leu Lys Asp His Phe
465                 470                 475                 480

Leu Met Asp Gly Gln Val Arg Ser Arg Met Leu Leu Gln Pro Gln
                 485                 490                 495

Ala Arg Tyr Gln Arg Val Ala Val His Arg Val Pro Gly Leu His His
                 500                 505                 510

Thr Tyr Asp Val Leu Phe Leu Gly Thr Gly Asp Gly Arg Leu His Lys
             515                 520                 525

Ala Val Ser Val Gly Pro Arg Val His Ile Ile Glu Glu Leu Gln Ile
             530                 535                 540

Phe Ser Ser Gly Gln Pro Val Gln Asn Leu Leu Asp Thr His Arg
545                 550                 555                 560

Gly Leu Leu Tyr Ala Ala Ser His Ser Gly Val Val Gln Val Pro Met
                 565                 570                 575

Ala Asn Cys Ser Leu Tyr Arg Ser Cys Gly Asp Cys Leu Leu Ala Arg
                 580                 585                 590

Asp Pro Tyr Cys Ala Trp Ser Gly Ser Cys Lys His Val Ser Leu
                 595                 600                 605

Tyr Gln Pro Gln Leu Ala Thr Arg Pro Trp Ile Gln Asp Ile Glu Gly
             610                 615                 620

Ala Ser Ala Lys Asp Leu Cys Ser Ala Ser Val Val Ser Pro Ser
625                 630                 635                 640

Phe Val Pro Thr Gly Glu Lys Pro Cys Glu Gln Val Gln Phe Gln Pro
                 645                 650                 655

Asn Thr Val Asn Thr Leu Ala Cys Pro Leu Leu Ser Asn Leu Ala Thr
                 660                 665                 670

Arg Leu Trp Leu Arg Asn Gly Ala Pro Val Asn Ala Ser Ala Ser Cys
             675                 680                 685

His Val Leu Pro Thr Gly Asp Leu Leu Val Gly Thr Gln Gln Leu
             690                 695                 700

Gly Glu Phe Gln Cys Trp Ser Leu Glu Glu Gly Phe Gln Gln Leu Val
705                 710                 715                 720

Ala Ser Tyr Cys Pro Glu Val Val Glu Asp Gly Val Ala Asp Gln Thr
                 725                 730                 735
```

```
Asp Glu Gly Gly Ser Val Pro Val Ile Ile Ser Thr Ser Arg Val Ser
            740                 745                 750

Ala Pro Ala Gly Gly Lys Ala Ser Trp Gly Ala Asp Arg Ser Tyr Trp
            755                 760                 765

Lys Glu Phe Leu Val Met Cys Thr Leu Phe Val Leu Ala Val Leu Leu
            770                 775                 780

Pro Val Leu Phe Leu Tyr Arg His Arg Asn Ser Met Lys Val Phe
785                 790                 795                 800

Leu Lys Gln Gly Glu Cys Ala Ser Val His Pro Lys Thr Cys Pro Val
                805                 810                 815

Val Leu Pro Pro Glu Thr Arg Pro Leu Asn Gly Leu Gly Pro Pro Ser
                820                 825                 830

Thr Pro Leu Asp His Arg Gly Tyr Gln Ser Leu Ser Asp Ser Pro Pro
                835                 840                 845

Gly Ala Arg Val Phe Thr Glu Ser Glu Lys Arg Pro Leu Ser Ile Gln
            850                 855                 860

Asp Ser Phe Val Glu Val Ser Pro Val Cys Pro Arg Pro Arg Val Arg
865                 870                 875                 880

Leu Gly Ser Glu Ile Arg Asp Ser Val Val
                885                 890

<210> SEQ ID NO 17
<211> LENGTH: 3558
<212> TYPE: DNA
<213> ORGANISM: homo sapiens

<400> SEQUENCE: 17
atgcccagcc agggcagggt ggagagctgc agctgcaggt ccggaggcgg gggcccccgg      60
ggcgactcgg gggcggaccg cggggcggag ctgccgcccg tgagtccggc cgagccacct     120
gagcccgagc cgcgggacac cgtcgctcct gctctccgaa tgctgcgcac cgcgatgggc     180
ctgaggagct ggctcgccgc cccatggggc gcgctgccgc tcggccaccg ctgctgctg     240 ctcctgctgc tgctgctcct gctgcagccg ccgcctccga cctgggcgct cagccccgg     300 atcagcctgc tctgggctc tgaagagcgg ccattcctca gattcgaagc tgaacacatc     360
tccaactaca cagcccttct gctgagcagg atggcagga ccctgtacgt gggtgctcga     420
gaggccctct ttgcactcag tagcaacctc agcttcctgc aggcggggga gtaccaggag     480
ctgctttggg gtgcagacgc agagaagaaa cagcagtgca gcttcaaggg caaggaccca     540
cagcgcgact gtcaaaacta catcaagatc ctcctgccgc tcagcggcag tcacctgttc     600
acctgtggca gcagccttt cagccccatg tgtacctaca tcaacatgga aacttcacc      660 ctggcaaggg acgagaaggg gaatgtcctc ctggaagatg caagggccg ttgtccctcc      720 gacccgaatt tcaagtccac tgccctggtg gttgatggcg agctctacac tggaacagtc     780
agcagcttcc aagggaatga cccggccatc tcgcggagcc aaaagccttc gccccaccaag    840 accgagagct ccctcaactg gctgcaagac ccagctttttg tggcctcagc ctacattcct    900
gagagcctgg gcagcttgca aggcgatgat gacaagatct actttttctt cagcgagact    960 ggccaggat ttgagttctt tgagaacacc attgtgtccc gcattgcccg catctgcaag     1020
ggcgatgagg tggagagcg ggtgctacag cagcgctgga cctccttcct caaggcccag     1080
ctgctgtgct acggcccga cgatggcttc ccccttcaacg tgctgcagga tgtcttcacg    1140 ctgagccca gcccccagga ctggcgtgac acccttttct atgggtcttc cacttcccag     1200
```

-continued

```
tggcacaggg gaactacaga aggctctgcc gtctgtgtct tcacaatgaa ggatgtgcag      1260
agagtcttca gcggcctcta caaggaggtg aaccgtgaga cacagcagtg gtacaccgtg      1320
acccacccgg tgcccacacc ccggcctgga gcgtgcatca ccaacagtgc ccgggaaagg      1380
aagatcaact catccctgca gctcccagac cgcgtgctga acttcctcaa ggaccacttc      1440
ctgatggacg ggcaggtccg aagccgcatg ctgctgctgc agcccaggc tcgctaccag       1500 cgcgtggctg tacaccgcgt ccctggcctg caccacacct acgatgtcct cttcctgggc      1560
actggtgacg gccggctcca caaggcagtg agcgtgggcc cccgggtgca catcattgag      1620
gagctgcaga tcttctcatc gggacagccc gtgcagaatc tgctcctgga cacccacagg      1680
gggctgctgt atgcggcctc acactcgggc gtagtccagg tgcccatggc caactgcagc      1740
ctgtacagga gctgtgggga ctgcctcctc gcccgggacc cctactgtgc ttggagcggc      1800
tccagctgca agcacgtcag cctctaccag cctcagctgg ccaccaggcc gtggatccag      1860
gacatcgagg gagccagcgc caaggacctt tgcagcgcgt cttcggttgt gtccccgtct      1920
tttgtaccaa caggggagaa gccatgtgag caagtccagt tccagcccaa cacagtgaac      1980
actttggcct gccgctcct ctccaacctg gcgacccgac tctggctacg caacggggcc       2040
cccgtcaatg cctcggcctc ctgccacgtg ctacccactg gggacctgct gctggtgggc      2100
acccaacagc tgggggagtt ccagtgctgg tcactagagg agggcttcca gcagctggta      2160
gccagctact gcccagaggt ggtggaggac ggggtggcag accaaacaga tacggtgccc      2220
acaccccggc ctggagcgtg catcaccaac agtgcccggg aaaggaagat caactcatcc      2280
ctgcagctcc cagaccgcgt gctgaacttc ctcaaggacc acttcctgat ggacgggcag      2340
gtccgaagcc gcatgctgct gctgcagccc aggctcgct accagcgcgt ggctgtacac       2400
cgcgtccctg gcctgcacca cacctacgat gtcctcttcc tgggcactgg tgacggccgg      2460
ctccacaagg cagtgagcgt gggcccccgg gtgcacatca ttgaggagct gcagatcttc      2520
tcatcgggac agcccgtgca gaatctgctc ctggacaccc acagggggct gctgtatgcg      2580
gcctcacact cgggcgtagt ccaggtgccc atgccaact gcagcctgta caggagctgt       2640
ggggactgcc tcctcgcccg ggaccctac tgtgcttgga gcggctccag ctgcaagcac       2700
gtcagcctct accagcctca gctggccacc aggccgtgga tccaggacat cgagggagcc      2760
agcgccaagg acctttgcag cgcgtcttcg gttgtgtccc cgtcttttgt accaacaggg      2820
gagaagccat gtgagcaagt ccagttccag cccaacacag tgaacacttt ggcctgcccg      2880
ctcctctcca acctggcgac ccgactctgg ctacgcaacg ggcccccgt caatgcctcg       2940 gcctcctgcc acgtgctacc cactggggac ctgctgctgg tgggcaccca acagctgggg      3000
gagttccagt gctggtcact agaggagggc ttccagcagc tggtagccag ctactgccca      3060
gaggtggtgg aggacgggt ggcaaaccaa acagatgagg gtggcagtgt acccgtcatt       3120
atcagcacat cgcgtgtgag tgcaccagct ggtggcaagg ccagctgggg tgcagacagg      3180
tcctactgga aggagttcct ggtgatgtgc acgctctttg tgctggccgt gctgctccca      3240
gttttattct tgctctaccg gcaccggaac agcatgaaag tcttcctgaa gcaggggaa      3300 tgtgccagcg tgcaccccaa gacctgccct gtggtgctgc ccctgagac ccgcccactc       3360 aacggcctag ggccccctag caccccgctc gatcaccgag gtaccagtc cctgtcagac       3420 agcccccggg gggcccgagt cttcactgag tcagagaaga ggccactcag catccaagac      3480
agcttcgtgg aggtatcccc agtgtgcccc cggccccggg tccgccttgg ctcggagatc      3540
cgtgactctg tggtgtga                                                    3558
```

<210> SEQ ID NO 18
<211> LENGTH: 1185
<212> TYPE: PRT
<213> ORGANISM: homo sapiens

<400> SEQUENCE: 18

```
Met Pro Ser Gln Gly Arg Val Glu Ser Cys Ser Cys Arg Ser Gly Gly
 1               5                  10                  15

Gly Gly Pro Arg Gly Asp Ser Gly Ala Asp Arg Gly Ala Glu Leu Pro
            20                  25                  30

Pro Val Ser Pro Ala Glu Pro Glu Pro Glu Pro Arg Asp Thr Val
        35                  40                  45

Ala Pro Ala Leu Arg Met Leu Arg Thr Ala Met Gly Leu Arg Ser Trp
 50                  55                  60

Leu Ala Ala Pro Trp Gly Ala Leu Pro Pro Arg Pro Pro Leu Leu Leu
 65                  70                  75                  80

Leu Leu Leu Leu Leu Leu Leu Gln Pro Pro Pro Thr Trp Ala
                85                  90                  95

Leu Ser Pro Arg Ile Ser Leu Pro Leu Gly Ser Glu Glu Arg Pro Phe
                100                 105                 110

Leu Arg Phe Glu Ala Glu His Ile Ser Asn Tyr Thr Ala Leu Leu Leu
        115                 120                 125

Ser Arg Asp Gly Arg Thr Leu Tyr Val Gly Ala Arg Glu Ala Leu Phe
130                 135                 140

Ala Leu Ser Ser Asn Leu Ser Phe Leu Pro Gly Gly Glu Tyr Gln Glu
145                 150                 155                 160

Leu Leu Trp Gly Ala Asp Ala Glu Lys Lys Gln Gln Cys Ser Phe Lys
                165                 170                 175

Gly Lys Asp Pro Gln Arg Asp Cys Gln Asn Tyr Ile Lys Ile Leu Leu
            180                 185                 190

Pro Leu Ser Gly Ser His Leu Phe Thr Cys Gly Thr Ala Ala Phe Ser
        195                 200                 205

Pro Met Cys Thr Tyr Ile Asn Met Glu Asn Phe Thr Leu Ala Arg Asp
210                 215                 220

Glu Lys Gly Asn Val Leu Leu Glu Asp Gly Lys Gly Arg Cys Pro Phe
225                 230                 235                 240

Asp Pro Asn Phe Lys Ser Thr Ala Leu Val Val Asp Gly Glu Leu Tyr
                245                 250                 255

Thr Gly Thr Val Ser Ser Phe Gln Gly Asn Asp Pro Ala Ile Ser Arg
            260                 265                 270

Ser Gln Ser Leu Arg Pro Thr Lys Thr Glu Ser Ser Leu Asn Trp Leu
        275                 280                 285

Gln Asp Pro Ala Phe Val Ala Ser Ala Tyr Ile Pro Glu Ser Leu Gly
290                 295                 300

Ser Leu Gln Gly Asp Asp Lys Ile Tyr Phe Phe Ser Glu Thr
305                 310                 315                 320

Gly Gln Glu Phe Glu Phe Phe Glu Asn Thr Ile Val Ser Arg Ile Ala
                325                 330                 335

Arg Ile Cys Lys Gly Asp Glu Gly Glu Arg Val Leu Gln Gln Arg
            340                 345                 350

Trp Thr Ser Phe Leu Lys Ala Gln Leu Leu Cys Ser Arg Pro Asp Asp
        355                 360                 365

Gly Phe Pro Phe Asn Val Leu Gln Asp Val Phe Thr Leu Ser Pro Ser
```

-continued

```
        370                 375                 380
Pro Gln Asp Trp Arg Asp Thr Leu Phe Tyr Gly Val Phe Thr Ser Gln
385                 390                 395                 400

Trp His Arg Gly Thr Thr Glu Gly Ser Ala Val Cys Val Phe Thr Met
            405                 410                 415

Lys Asp Val Gln Arg Val Phe Ser Gly Leu Tyr Lys Glu Val Asn Arg
            420                 425                 430

Glu Thr Gln Gln Trp Tyr Thr Val Thr His Pro Val Pro Thr Pro Arg
            435                 440                 445

Pro Gly Ala Cys Ile Thr Asn Ser Ala Arg Glu Arg Lys Ile Asn Ser
450                 455                 460

Ser Leu Gln Leu Pro Asp Arg Val Leu Asn Phe Leu Lys Asp His Phe
465                 470                 475                 480

Leu Met Asp Gly Gln Val Arg Ser Arg Met Leu Leu Gln Pro Gln
            485                 490                 495

Ala Arg Tyr Gln Arg Val Ala Val His Arg Val Pro Gly Leu His His
            500                 505                 510

Thr Tyr Asp Val Leu Phe Leu Gly Thr Gly Asp Gly Arg Leu His Lys
            515                 520                 525

Ala Val Ser Val Gly Pro Arg Val His Ile Ile Glu Glu Leu Gln Ile
            530                 535                 540

Phe Ser Ser Gly Gln Pro Val Gln Asn Leu Leu Leu Asp Thr His Arg
545                 550                 555                 560

Gly Leu Leu Tyr Ala Ala Ser His Ser Gly Val Val Gln Val Pro Met
                    565                 570                 575

Ala Asn Cys Ser Leu Tyr Arg Ser Cys Gly Asp Cys Leu Leu Ala Arg
            580                 585                 590

Asp Pro Tyr Cys Ala Trp Ser Gly Ser Ser Cys Lys His Val Ser Leu
            595                 600                 605

Tyr Gln Pro Gln Leu Ala Thr Arg Pro Trp Ile Gln Asp Ile Glu Gly
            610                 615                 620

Ala Ser Ala Lys Asp Leu Cys Ser Ala Ser Val Val Ser Pro Ser
625                 630                 635                 640

Phe Val Pro Thr Gly Glu Lys Pro Cys Glu Gln Val Gln Phe Gln Pro
            645                 650                 655

Asn Thr Val Asn Thr Leu Ala Cys Pro Leu Leu Ser Asn Leu Ala Thr
            660                 665                 670

Arg Leu Trp Leu Arg Asn Gly Ala Pro Val Asn Ala Ser Ala Ser Cys
            675                 680                 685

His Val Leu Pro Thr Gly Asp Leu Leu Leu Val Gly Thr Gln Gln Leu
690                 695                 700

Gly Glu Phe Gln Cys Trp Ser Leu Glu Glu Gly Phe Gln Gln Leu Val
705                 710                 715                 720

Ala Ser Tyr Cys Pro Glu Val Val Glu Asp Gly Val Ala Asp Gln Thr
            725                 730                 735

Asp Thr Val Pro Thr Pro Arg Pro Gly Ala Cys Ile Thr Asn Ser Ala
            740                 745                 750

Arg Glu Arg Lys Ile Asn Ser Ser Leu Gln Leu Pro Asp Arg Val Leu
            755                 760                 765

Asn Phe Leu Lys Asp His Phe Leu Met Asp Gly Gln Val Arg Ser Arg
            770                 775                 780

Met Leu Leu Leu Gln Pro Gln Ala Arg Tyr Gln Arg Val Ala Val His
785                 790                 795                 800
```

-continued

Arg Val Pro Gly Leu His His Thr Tyr Asp Val Leu Phe Leu Gly Thr
                805                 810                 815
Gly Asp Gly Arg Leu His Lys Ala Val Ser Val Gly Pro Arg Val His
            820                 825                 830
Ile Ile Glu Glu Leu Gln Ile Phe Ser Ser Gly Gln Pro Val Gln Asn
        835                 840                 845
Leu Leu Leu Asp Thr His Arg Gly Leu Leu Tyr Ala Ala Ser His Ser
    850                 855                 860
Gly Val Gln Val Pro Met Ala Asn Cys Ser Leu Tyr Arg Ser Cys
865                 870                 875                 880
Gly Asp Cys Leu Leu Ala Arg Asp Pro Tyr Cys Ala Trp Ser Gly Ser
            885                 890                 895
Ser Cys Lys His Val Ser Leu Tyr Gln Pro Gln Leu Ala Thr Arg Pro
                900                 905                 910
Trp Ile Gln Asp Ile Glu Gly Ala Ser Ala Lys Asp Leu Cys Ser Ala
            915                 920                 925
Ser Ser Val Val Ser Pro Ser Phe Val Pro Thr Gly Glu Lys Pro Cys
    930                 935                 940
Glu Gln Val Gln Phe Gln Pro Asn Thr Val Asn Thr Leu Ala Cys Pro
945                 950                 955                 960
Leu Leu Ser Asn Leu Ala Thr Arg Leu Trp Leu Arg Asn Gly Ala Pro
                965                 970                 975
Val Asn Ala Ser Ala Ser Cys His Val Leu Pro Thr Gly Asp Leu Leu
            980                 985                 990
Leu Val Gly Thr Gln Gln Leu Gly Glu Phe Gln Cys Trp Ser Leu Glu
        995                 1000                1005
Glu Gly Phe Gln Gln Leu Val Ala Ser Tyr Cys Pro Glu Val Val Glu
    1010                1015                1020
Asp Gly Val Ala Asn Gln Thr Asp Glu Gly Gly Ser Val Pro Val Ile
1025                1030                1035                1040
Ile Ser Thr Ser Arg Val Ser Ala Pro Ala Gly Gly Lys Ala Ser Trp
                1045                1050                1055
Gly Ala Asp Arg Ser Tyr Trp Lys Glu Phe Leu Val Met Cys Thr Leu
            1060                1065                1070
Phe Val Leu Ala Val Leu Leu Pro Val Leu Phe Leu Leu Tyr Arg His
        1075                1080                1085
Arg Asn Ser Met Lys Val Phe Leu Lys Gln Gly Glu Cys Ala Ser Val
    1090                1095                1100
His Pro Lys Thr Cys Pro Val Val Leu Pro Pro Glu Thr Arg Pro Leu
1105                1110                1115                1120
Asn Gly Leu Gly Pro Pro Ser Thr Pro Leu Asp His Arg Gly Tyr Gln
                1125                1130                1135
Ser Leu Ser Asp Ser Pro Pro Gly Ala Arg Val Phe Thr Glu Ser Glu
            1140                1145                1150
Lys Arg Pro Leu Ser Ile Gln Asp Ser Phe Val Glu Val Ser Pro Val
        1155                1160                1165
Cys Pro Arg Pro Arg Val Arg Leu Gly Ser Glu Ile Arg Asp Ser Val
    1170                1175                1180
Val
1185

<210> SEQ ID NO 19
<211> LENGTH: 2145

<212> TYPE: DNA
<213> ORGANISM: homo sapiens

<400> SEQUENCE: 19

| | | | | | |
|---|---|---|---|---|---:|
| atgctgcgca | ccgcgatggg | cctgaggagc | tggctcgccg | ccccatgggg | cgcgctgccg | 60 |
| cctcggccac | cgctgctgct | gctcctgctg | ctgctgctcc | tgctgcagcc | gccgcctccg | 120 |
| acctgggcgc | tcagccccg | gatcagcctg | cctctgggct | ctgaagagcg | gccattcctc | 180 |
| agattcgaag | ctgaacacat | ctccaactac | acagcccttc | tgctgagcag | ggatggcagg | 240 |
| accctgtacg | tgggtgctcg | agaggccctc | tttgcactca | gtagcaacct | cagcttcctg | 300 |
| ccaggcgggg | agtaccagga | gctgctttgg | ggtgcagacg | cagagaagaa | acagcagtgc | 360 |
| agcttcaagg | gcaaggaccc | cagcgcgac | tgtcaaaact | acatcaagat | cctcctgccg | 420 |
| ctcagcggca | gtcacctgtt | cacctgtggc | acagcagcct | cagccccat | gtgtacctac | 480 |
| atcaacatgg | agaacttcac | cctggcaagg | gacgagaagg | ggaatgtcct | cctggaagat | 540 |
| ggcaagggcc | gttgtcccct | cgacccgaat | ttcaagtcca | ctgccctggt | ggttgatggc | 600 |
| gagctctaca | ctggaacagt | cagcagcttc | aagggaatg | accggccat | ctcgcggagc | 660 |
| caaagccttc | gccccaccaa | gaccgagagc | tccctcaact | ggctgcaaga | cccagctttt | 720 |
| gtggcctcag | cctacattcc | tgagagcctg | gcagcttgc | aaggcgatga | tgacaagatc | 780 |
| tactttttct | tcagcgagac | tggccaggaa | tttgagttct | tgagaacac | cattgtgtcc | 840 |
| cgcattgccc | gcatctgcaa | gggcgatgag | ggtggagagc | gggtgctaca | gcagcgctgg | 900 |
| acctccttcc | tcaaggccca | gctgctgtgc | tcacggcccg | acgatggctt | ccccttcaac | 960 |
| gtgctgcagg | atgtcttcac | gctgagcccc | agccccagg | actggcgtga | caccctttc | 1020 |
| tatgggggtct | tcacttccca | gtggcacagg | ggaactacag | aaggctctgc | cgtctgtgtc | 1080 |
| ttcacaatga | aggatgtgca | gagagtcttc | agcggcctct | acaaggaggt | gaaccgtgag | 1140 |
| acacagcagt | ggtacaccgt | gacccacccg | gtgcccacac | cccggcctgg | agcgtgcatc | 1200 |
| accaacagtg | cccgggaaag | gaagatcaac | tcatccctgc | agctcccaga | ccgcgtgctg | 1260 |
| aacttcctca | aggaccactt | cctgatggac | ggcaggtcc | gaagccgcat | gctgctgctg | 1320 |
| cagccccagg | ctcgctacca | gcgcgtggct | gtacaccgcg | tccctggcct | gcaccacacc | 1380 |
| tacgatgtcc | tcttcctggg | cactggtgac | ggccggctcc | acaaggcagt | gagcgtgggc | 1440 |
| ccccgggtgc | acatcattga | ggagctgcag | atcttctcat | cgggacagcc | cgtgcagaat | 1500 |
| ctgctcctgg | acacccacag | ggggctgctg | tatgcggcct | cacactcggg | cgtagtccag | 1560 |
| gtgcccatgg | ccaactgcag | cctgtacagg | agctgtgggg | actgcctcct | cgcccgggac | 1620 |
| ccctactgtg | cttggagcgg | ctccagctgc | aagcacgtca | gcctctacca | gcctcagctg | 1680 |
| gccaccaggc | cgtggatcca | ggacatcgag | ggagccagcg | ccaaggacct | ttgcagcgcg | 1740 |
| tcttcggttg | tgtccccgtc | ttttgtacca | acagggggaga | agccatgtga | gcaagtccag | 1800 |
| ttccagccca | acacagtgaa | cactttggcc | tgcccgctcc | tctccaacct | ggcgacccga | 1860 |
| ctctggctac | gcaacggggc | cccgtcaat | gcctcggcct | cctgccacgt | gctacccact | 1920 |
| ggggacctgc | tgctggtggg | cacccaacag | ctgggggagt | tccagtgctg | gtcactagag | 1980 |
| gagggcttcc | agcagctggt | agccagctac | tgcccagagg | tggtggagga | cggggtggca | 2040 |
| gaccaaacag | atgagggtgg | cagtgtaccc | gtcattatca | gcacatcgcg | tgtgagtgca | 2100 |
| cccagcaccc | ggctggggcc | tgtccctgga | tgcaggctac | tctag | 2145 |

<210> SEQ ID NO 20

```
<211> LENGTH: 714
<212> TYPE: PRT
<213> ORGANISM: homo sapiens

<400> SEQUENCE: 20

Met Leu Arg Thr Ala Met Gly Leu Arg Ser Trp Leu Ala Ala Pro Trp
 1               5                  10                  15

Gly Ala Leu Pro Pro Arg Pro Pro Leu Leu Leu Leu Leu Leu Leu Leu
             20                  25                  30

Leu Leu Leu Gln Pro Pro Pro Thr Trp Ala Leu Ser Pro Arg Ile
             35                  40                  45

Ser Leu Pro Leu Gly Ser Glu Glu Arg Pro Phe Leu Arg Phe Glu Ala
 50                  55                  60

Glu His Ile Ser Asn Tyr Thr Ala Leu Leu Ser Arg Asp Gly Arg
65                  70                  75                  80

Thr Leu Tyr Val Gly Ala Arg Glu Ala Leu Phe Ala Leu Ser Ser Asn
                 85                  90                  95

Leu Ser Phe Leu Pro Gly Gly Glu Tyr Gln Glu Leu Leu Trp Gly Ala
                100                 105                 110

Asp Ala Glu Lys Lys Gln Gln Cys Ser Phe Lys Gly Lys Asp Pro Gln
            115                 120                 125

Arg Asp Cys Gln Asn Tyr Ile Lys Ile Leu Leu Pro Leu Ser Gly Ser
130                 135                 140

His Leu Phe Thr Cys Gly Thr Ala Ala Phe Ser Pro Met Cys Thr Tyr
145                 150                 155                 160

Ile Asn Met Glu Asn Phe Thr Leu Ala Arg Asp Glu Lys Gly Asn Val
                165                 170                 175

Leu Leu Glu Asp Gly Lys Gly Arg Cys Pro Phe Asp Pro Asn Phe Lys
            180                 185                 190

Ser Thr Ala Leu Val Val Asp Gly Glu Leu Tyr Thr Gly Thr Val Ser
        195                 200                 205

Ser Phe Gln Gly Asn Asp Pro Ala Ile Ser Arg Ser Gln Ser Leu Arg
    210                 215                 220

Pro Thr Lys Thr Glu Ser Ser Leu Asn Trp Leu Gln Asp Pro Ala Phe
225                 230                 235                 240

Val Ala Ser Ala Tyr Ile Pro Glu Ser Leu Gly Ser Leu Gln Gly Asp
                245                 250                 255

Asp Asp Lys Ile Tyr Phe Phe Ser Glu Thr Gly Gln Glu Phe Glu
            260                 265                 270

Phe Phe Glu Asn Thr Ile Val Ser Arg Ile Ala Arg Ile Cys Lys Gly
        275                 280                 285

Asp Glu Gly Gly Glu Arg Val Leu Gln Gln Arg Trp Thr Ser Phe Leu
    290                 295                 300

Lys Ala Gln Leu Leu Cys Ser Arg Pro Asp Asp Gly Phe Pro Phe Asn
305                 310                 315                 320

Val Leu Gln Asp Val Phe Thr Leu Ser Pro Ser Pro Gln Asp Trp Arg
                325                 330                 335

Asp Thr Leu Phe Tyr Gly Val Phe Thr Ser Gln Trp His Arg Gly Thr
            340                 345                 350

Thr Glu Gly Ser Ala Val Cys Val Phe Thr Met Lys Asp Val Gln Arg
        355                 360                 365

Val Phe Ser Gly Leu Tyr Lys Glu Val Asn Arg Glu Thr Gln Gln Trp
    370                 375                 380

Tyr Thr Val Thr His Pro Val Pro Thr Pro Arg Pro Gly Ala Cys Ile
```

```
                385                 390                 395                 400
        Thr Asn Ser Ala Arg Glu Arg Lys Ile Asn Ser Ser Leu Gln Leu Pro
                            405                 410                 415

Asp Arg Val Leu Asn Phe Leu Lys Asp His Phe Leu Met Asp Gly Gln
                        420                 425                 430

Val Arg Ser Arg Met Leu Leu Gln Pro Gln Ala Arg Tyr Gln Arg
                    435                 440                 445

Val Ala Val His Arg Val Pro Gly Leu His His Thr Tyr Asp Val Leu
                450                 455                 460

Phe Leu Gly Thr Gly Asp Gly Arg Leu His Lys Ala Val Ser Val Gly
        465                 470                 475                 480

Pro Arg Val His Ile Ile Glu Glu Leu Gln Ile Phe Ser Ser Gly Gln
                            485                 490                 495

Pro Val Gln Asn Leu Leu Leu Asp Thr His Arg Gly Leu Leu Tyr Ala
                        500                 505                 510

Ala Ser His Ser Gly Val Val Gln Val Pro Met Ala Asn Cys Ser Leu
                    515                 520                 525

Tyr Arg Ser Cys Gly Asp Cys Leu Leu Ala Arg Asp Pro Tyr Cys Ala
                530                 535                 540

Trp Ser Gly Ser Ser Cys Lys His Val Ser Leu Tyr Gln Pro Gln Leu
        545                 550                 555                 560

Ala Thr Arg Pro Trp Ile Gln Asp Ile Glu Gly Ala Ser Ala Lys Asp
                            565                 570                 575

Leu Cys Ser Ala Ser Ser Val Val Ser Pro Ser Phe Val Pro Thr Gly
                        580                 585                 590

Glu Lys Pro Cys Glu Gln Val Gln Phe Gln Pro Asn Thr Val Asn Thr
                    595                 600                 605

Leu Ala Cys Pro Leu Leu Ser Asn Leu Ala Thr Arg Leu Trp Leu Arg
                610                 615                 620

Asn Gly Ala Pro Val Asn Ala Ser Ala Ser Cys His Val Leu Pro Thr
        625                 630                 635                 640

Gly Asp Leu Leu Leu Val Gly Thr Gln Gln Leu Gly Glu Phe Gln Cys
                            645                 650                 655

Trp Ser Leu Glu Glu Gly Phe Gln Gln Leu Val Ala Ser Tyr Cys Pro
                        660                 665                 670

Glu Val Val Glu Asp Gly Val Ala Asp Gln Thr Asp Glu Gly Gly Ser
                    675                 680                 685

Val Pro Val Ile Ile Ser Thr Ser Arg Val Ser Ala Pro Ser Thr Arg
                690                 695                 700

Leu Gly Pro Val Pro Gly Cys Arg Leu Leu
        705                 710

<210> SEQ ID NO 21
<211> LENGTH: 2985
<212> TYPE: DNA
<213> ORGANISM: homo sapiens

<400> SEQUENCE: 21
atgctgcgca ccgcgatggg cctgaggagc tggctcgccg ccccatgggg cgcgctgccg      60
cctcggccac cgctgctgct gctcctgctg ctgctgctcc tgctgcagcc gccgcctccg     120
acctgggcgc tcagccccg gatcagcctg cctctgggct ctgaagagcg gccattcctc     180
agattcgaag ctgaacacat ctccaactac acagcccttc tgctgagcag ggatggcagg     240
accctgtacg tgggtgctcg agaggccctc tttgcactca gtagcaacct cagcttcctg     300
```

-continued

```
ccaggcgggg agtaccagga gctgctttgg ggtgcagacg cagagaagaa acagcagtgc    360
agcttcaagg gcaaggaccc acagcgcgac tgtcaaaact acatcaagat cctcctgccg    420
ctcagcggca gtcacctgtt cacctgtggc acagcagcct tcagccccat gtgtacctac    480
atcaacatgg agaacttcac cctggcaagg gacgagaagg ggaatgtcct cctggaagat    540
ggcaagggcc gttgtccctt cgacccgaat ttcaagtcca ctgccctggt ggttgatggc    600
gagctctaca ctggaacagt cagcagcttc aagggaatg acccggccat ctcgcggagc    660
caaagccttc gccccaccaa gaccgagagc tccctcaact ggctgcaaga cccagctttt    720
gtggcctcag cctacattcc tgagagcctg gcagcttgc aaggcgatga tgacaagatc    780 tacttttct tcagcgagac tggccaggaa tttgagttct tgagaacac cattgtgtcc    840 cgcattgccc gcatctgcaa gggcgatgag ggtggagagc gggtgctaca gcagcgctgg    900
acctccttcc tcaaggccca gctgctgtgc tcacggcccg acgatggctt ccccttcaac    960
gtgctgcagg atgtcttcac gctgagcccc agccccagg actggcgtga cacccttttc    1020 tatgggtct tcacttccca gtggcacagg ggaactacag aaggctctgc cgtctgtgtc    1080
ttcacaatga aggatgtgca gagagtcttc agcggcctct acaaggaggt gaaccgtgag    1140
acacagcagt ggtacaccgt gacccacccg gtgcccacac ccggcctgg agcgtgcatc    1200 accaacagtg cccgggaaag gaagatcaac tcatccctgc agctcccaga ccgcgtgctg    1260
aacttcctca aggaccactt cctgatggac gggcaggtcc gaagccgcat gctgctgctg    1320
cagccccagg ctcgctacca gcgcgtggct gtacaccgcg tccctggcct gcaccacacc    1380
tacgatgtcc tcttcctggg cactggtgac ggccggctcc acaaggcagt gagcgtgggc    1440 cccgggtgc acatcattga ggagctgcag atcttctcat cgggacagcc cgtgcagaat    1500
ctgctcctgg acacccacag ggggctgctg tatgcggcct cacactcggg cgtagtccag    1560
gtgcccatgg ccaactgcag cctgtacagg agctgtgggg actgcctcct cgcccgggac    1620
ccctactgtg cttggagcgg ctccagctgc aagcacgtca gcctctacca gcctcagctg    1680
gccaccaggc cgtggatcca ggacatcgag ggagccagcg ccaaggacct ttgcagcgcg    1740
tcttcggttg tgtccccgtc ttttgtacca acaggggaga agccatgtga gcaagtccag    1800
ttccagccca acacagtgaa cactttggcc tgccgctcc tctccaacct ggcgacccga    1860
ctctggctac gcaacggggc ccccgtcaat gcctcggcct cctgccacgt gctacccact    1920
ggggacctgc tgctggtggg cacccaacag ctggggagt ccagtgctg gtcactagag    1980 gagggcttcc agcagctggt agccagctac tgcccagagg tggtggagga cggggtggca    2040
gaccaaacag atacggtgcc cacacccgg cctggagcgt gcatcaccaa cagtgcccgg    2100
gaaaggaaga tcaactcatc cctgcagctc ccagaccgcg tgctgaactt cctcaaggac    2160
cacttcctga tggacgggca ggtccgaagc cgcatgctgc tgctgcagcc ccaggctcgc    2220
taccagcgcg tggctgtaca ccgcgtccct ggcctgcacc acacctacga tgtcctcttc    2280
ctgggcactg gtgacggccg gctccacaag gcagtgagcg tgggcccccg ggtgcacatc    2340
attgaggagc tgcagatctt ctcatcggga cagcccgtgc agaatctgct cctggacacc    2400
cacagggggc tgctgtatgc ggcctcacac tcgggcgtag tccaggtgcc catgccaac    2460 tgcagcctgt acaggagctg tggggactgc ctcctcgccc gggaccccta ctgtgcttgg    2520
agcggctcca gctgcaagca cgtcagcctc taccagcctc agctggccac caggccgtgg    2580
atccaggaca tcgagggagc cagcgccaag gacctttgca gcgcgtcttc ggttgtgtcc    2640
```

-continued

```
ccgtcttttg taccaacagg ggagaagcca tgtgagcaag tccagttcca gcccaacaca    2700
gtgaacactt tggcctgccc gctcctctcc aacctggcga cccgactctg gctacgcaac    2760
ggggcccccg tcaatgcctc ggcctcctgc cacgtgctac ccactgggga cctgctgctg    2820
gtgggcactg gagtagcacc ttccacgacc aggagaggca ctggggaggg gtcacaggga    2880
tgccacccgg gcagacctga ggaagagatg gaggtggacg tgtcagcacc cggctggggc    2940
ctgtccctgg atgcaggcta ctctagggca cctgtcccgc cttga                   2985
```

<210> SEQ ID NO 22
<211> LENGTH: 994
<212> TYPE: PRT
<213> ORGANISM: homo sapiens

<400> SEQUENCE: 22

```
Met Leu Arg Thr Ala Met Gly Leu Arg Ser Trp Leu Ala Ala Pro Trp
  1               5                  10                  15

Gly Ala Leu Pro Pro Arg Pro Pro Leu Leu Leu Leu Leu Leu Leu Leu
                 20                  25                  30

Leu Leu Leu Gln Pro Pro Pro Thr Trp Ala Leu Ser Pro Arg Ile
             35                  40                  45

Ser Leu Pro Leu Gly Ser Glu Glu Arg Pro Phe Leu Arg Phe Glu Ala
 50                  55                  60

Glu His Ile Ser Asn Tyr Thr Ala Leu Leu Leu Ser Arg Asp Gly Arg
 65                  70                  75                  80

Thr Leu Tyr Val Gly Ala Arg Glu Ala Leu Phe Ala Leu Ser Ser Asn
                 85                  90                  95

Leu Ser Phe Leu Pro Gly Gly Glu Tyr Gln Glu Leu Leu Trp Gly Ala
            100                 105                 110

Asp Ala Glu Lys Lys Gln Gln Cys Ser Phe Lys Gly Lys Asp Pro Gln
        115                 120                 125

Arg Asp Cys Gln Asn Tyr Ile Lys Ile Leu Leu Pro Leu Ser Gly Ser
130                 135                 140

His Leu Phe Thr Cys Gly Thr Ala Ala Phe Ser Pro Met Cys Thr Tyr
145                 150                 155                 160

Ile Asn Met Glu Asn Phe Thr Leu Ala Arg Asp Glu Lys Gly Asn Val
                165                 170                 175

Leu Leu Glu Asp Gly Lys Gly Arg Cys Pro Phe Asp Pro Asn Phe Lys
            180                 185                 190

Ser Thr Ala Leu Val Val Asp Gly Glu Leu Tyr Thr Gly Thr Val Ser
        195                 200                 205

Ser Phe Gln Gly Asn Asp Pro Ala Ile Ser Arg Ser Gln Ser Leu Arg
    210                 215                 220

Pro Thr Lys Thr Glu Ser Ser Leu Asn Trp Leu Gln Asp Pro Ala Phe
225                 230                 235                 240

Val Ala Ser Ala Tyr Ile Pro Glu Ser Leu Gly Ser Leu Gln Gly Asp
                245                 250                 255

Asp Asp Lys Ile Tyr Phe Phe Ser Glu Thr Gly Gln Glu Phe Glu
            260                 265                 270

Phe Phe Glu Asn Thr Ile Val Ser Arg Ile Ala Arg Ile Cys Lys Gly
        275                 280                 285

Asp Glu Gly Gly Glu Arg Val Leu Gln Gln Arg Trp Thr Ser Phe Leu
    290                 295                 300

Lys Ala Gln Leu Leu Cys Ser Arg Pro Asp Asp Gly Phe Pro Phe Asn
305                 310                 315                 320
```

-continued

```
Val Leu Gln Asp Val Phe Thr Leu Ser Pro Ser Pro Gln Asp Trp Arg
                325                 330                 335

Asp Thr Leu Phe Tyr Gly Val Phe Thr Ser Gln Trp His Arg Gly Thr
            340                 345                 350

Thr Glu Gly Ser Ala Val Cys Val Phe Thr Met Lys Asp Val Gln Arg
        355                 360                 365

Val Phe Ser Gly Leu Tyr Lys Glu Val Asn Arg Glu Thr Gln Gln Trp
    370                 375                 380

Tyr Thr Val Thr His Pro Val Pro Thr Pro Arg Pro Gly Ala Cys Ile
385                 390                 395                 400

Thr Asn Ser Ala Arg Glu Arg Lys Ile Asn Ser Ser Leu Gln Leu Pro
                405                 410                 415

Asp Arg Val Leu Asn Phe Leu Lys Asp His Phe Leu Met Asp Gly Gln
            420                 425                 430

Val Arg Ser Arg Met Leu Leu Leu Gln Pro Gln Ala Arg Tyr Gln Arg
        435                 440                 445

Val Ala Val His Arg Val Pro Gly Leu His His Thr Tyr Asp Val Leu
    450                 455                 460

Phe Leu Gly Thr Gly Asp Gly Arg Leu His Lys Ala Val Ser Val Gly
465                 470                 475                 480

Pro Arg Val His Ile Ile Glu Glu Leu Gln Ile Phe Ser Ser Gly Gln
                485                 490                 495

Pro Val Gln Asn Leu Leu Leu Asp Thr His Arg Gly Leu Leu Tyr Ala
            500                 505                 510

Ala Ser His Ser Gly Val Val Gln Val Pro Met Ala Asn Cys Ser Leu
        515                 520                 525

Tyr Arg Ser Cys Gly Asp Cys Leu Leu Ala Arg Asp Pro Tyr Cys Ala
    530                 535                 540

Trp Ser Gly Ser Ser Cys Lys His Val Ser Leu Tyr Gln Pro Gln Leu
545                 550                 555                 560

Ala Thr Arg Pro Trp Ile Gln Asp Ile Glu Gly Ala Ser Ala Lys Asp
                565                 570                 575

Leu Cys Ser Ala Ser Ser Val Val Ser Pro Ser Phe Val Pro Thr Gly
            580                 585                 590

Glu Lys Pro Cys Glu Gln Val Gln Phe Gln Pro Asn Thr Val Asn Thr
        595                 600                 605

Leu Ala Cys Pro Leu Leu Ser Asn Leu Ala Thr Arg Leu Trp Leu Arg
    610                 615                 620

Asn Gly Ala Pro Val Asn Ala Ser Ala Ser Cys His Val Leu Pro Thr
625                 630                 635                 640

Gly Asp Leu Leu Leu Val Gly Thr Gln Gln Leu Gly Glu Phe Gln Cys
                645                 650                 655

Trp Ser Leu Glu Glu Gly Phe Gln Gln Leu Val Ala Ser Tyr Cys Pro
            660                 665                 670

Glu Val Val Glu Asp Gly Val Ala Asp Gln Thr Asp Thr Val Pro Thr
        675                 680                 685

Pro Arg Pro Gly Ala Cys Ile Thr Asn Ser Ala Arg Glu Arg Lys Ile
    690                 695                 700

Asn Ser Ser Leu Gln Leu Pro Asp Arg Val Leu Asn Phe Leu Lys Asp
705                 710                 715                 720

His Phe Leu Met Asp Gly Gln Val Arg Ser Arg Met Leu Leu Leu Gln
                725                 730                 735
```

```
Pro Gln Ala Arg Tyr Gln Arg Val Ala Val His Arg Val Pro Gly Leu
                740                 745                 750
His His Thr Tyr Asp Val Leu Phe Leu Gly Thr Gly Asp Gly Arg Leu
            755                 760                 765
His Lys Ala Val Ser Val Gly Pro Arg Val His Ile Ile Glu Glu Leu
        770                 775                 780
Gln Ile Phe Ser Ser Gly Gln Pro Val Gln Asn Leu Leu Leu Asp Thr
785                 790                 795                 800
His Arg Gly Leu Leu Tyr Ala Ala Ser His Ser Gly Val Val Gln Val
                805                 810                 815
Pro Met Ala Asn Cys Ser Leu Tyr Arg Ser Cys Gly Asp Cys Leu Leu
            820                 825                 830
Ala Arg Asp Pro Tyr Cys Ala Trp Ser Gly Ser Cys Lys His Val
        835                 840                 845
Ser Leu Tyr Gln Pro Gln Leu Ala Thr Arg Pro Trp Ile Gln Asp Ile
850                 855                 860
Glu Gly Ala Ser Ala Lys Asp Leu Cys Ser Ala Ser Ser Val Val Ser
865                 870                 875                 880
Pro Ser Phe Val Pro Thr Gly Glu Lys Pro Cys Glu Gln Val Gln Phe
                885                 890                 895
Gln Pro Asn Thr Val Asn Thr Leu Ala Cys Pro Leu Leu Ser Asn Leu
            900                 905                 910
Ala Thr Arg Leu Trp Leu Arg Asn Gly Ala Pro Val Asn Ala Ser Ala
        915                 920                 925
Ser Cys His Val Leu Pro Thr Gly Asp Leu Leu Val Gly Thr Gly
    930                 935                 940
Val Ala Pro Ser Thr Thr Arg Arg Gly Thr Gly Glu Gly Ser Gln Gly
945                 950                 955                 960
Cys His Pro Gly Arg Pro Glu Glu Glu Met Glu Val Asp Val Ser Ala
                965                 970                 975
Pro Gly Trp Gly Leu Ser Leu Asp Ala Gly Tyr Ser Arg Ala Pro Val
            980                 985                 990
Pro Pro

<210> SEQ ID NO 23
<211> LENGTH: 3030
<212> TYPE: DNA
<213> ORGANISM: homo sapiens

<400> SEQUENCE: 23
atgctgcgca ccgcgatggg cctgaggagc tggctcgccg ccccatgggg cgcgctgccg    60
cctcggccac cgctgctgct gctcctgctg ctgctgctcc tgctgcagcc gccgcctccg   120
acctgggcgc tcagccccg gatcagcctg cctctgggct ctgaagagcg gccattcctc   180
agattcgaag ctgaacacat ctccaactac acagcccttc tgctgagcag ggatggcagg   240
accctgtacg tgggtgctcg agaggccctc tttgcactca gtagcaacct cagcttcctg   300
ccaggcgggg agtaccagga gctgctttgg ggtgcagacg cagagaagaa acagcagtgc   360
agcttcaagg gcaaggaccc acagcgcgac tgtcaaaact acatcaagat cctcctgccg   420
ctcagcggca gtcacctgtt cacctgtggc acagcagcct tcagcccat gtgtacctac   480 atcaacatgg agaacttcac cctggcaagg gacgagaagg ggaatgtcct cctggaagat   540
ggcaagggcc gttgtccctt cgacccgaat ttcaagtcca ctgccctggt ggttgatggc   600
gagctctaca ctggaacagt cagcagcttc caagggaatg accggccat ctcgcggagc   660
```

```
caaagccttc gccccaccaa gaccgagagc tccctcaact ggctgcaaga cccagctttt    720
gtggcctcag cctacattcc tgagagcctg ggcagcttgc aaggcgatga tgacaagatc    780
tactttttct tcagcgagac tggccaggaa tttgagttct ttgagaacac cattgtgtcc    840
cgcattgccc gcatctgcaa gggcgatgag ggtggagagc gggtgctaca gcagcgctgg    900
acctccttcc tcaaggccca gctgctgtgc tcacggcccg acgatggctt ccccttcaac    960
gtgctgcagg atgtcttcac gctgagcccc agccccagg  actggcgtga caccctttc    1020 tatgggtct  tcacttccca gtggcacagg ggaactacag aaggctctgc cgtctgtgtc    1080
ttcacaatga aggatgtgca gagagtcttc agcggcctct acaaggaggt gaaccgtgag    1140
acacagcagt ggtacaccgt gacccacccg gtgcccacac ccggcctgg  agcgtgcatc    1200 accaacagtg cccgggaaag gaagatcaac tcatccctgc agctcccaga ccgcgtgctg    1260
aacttcctca aggaccactt cctgatggac gggcaggtcc gaagccgcat gctgctgctg    1320
cagccccagg ctcgctacca gcgcgtggct gtacaccgcg tccctggcct gcaccacacc    1380
tacgatgtcc tcttcctggg cactggtgac ggccggctcc acaaggcagt gagcgtgggc    1440
ccccgggtgc acatcattga ggagctgcag atcttctcat cgggacagcc cgtgcagaat    1500
ctgctcctgg acacccacag ggggctgctg tatgcggcct cacactcggg cgtagtccag    1560
gtgcccatgg ccaactgcag cctgtacagg agctgtgggg actgcctcct cgcccgggac    1620
ccctactgtg cttggagcgg ctccagctgc aagcacgtca gcctctacca gcctcagctg    1680
gccaccaggc cgtggatcca ggacatcgag ggagccagcg ccaaggacct ttgcagcgcg    1740
tcttcggttg tgtccccgtc ttttgtacca acagggagaa agccatgtga gcaagtccag    1800
ttccagccca acacagtgaa cactttggcc tgcccgctcc tctccaacct ggcgacccga    1860
ctctggctac gcaacggggc ccccgtcaat gcctcggcct cctgccacgt gctacccact    1920
ggggacctgc tgctggtggg cacccaacag ctggggagt  tccagtgctg gtcactagag    1980
gagggcttcc agcagctggt agccagctac tgcccagagg tggtggagga cggggtggca    2040
gaccaaacag atacggtgcc cacaccccgg cctggagcgt gcatcaccaa cagtgcccgg    2100
gaaaggaaga tcaactcatc cctgcagctc ccagaccgcg tgctgaactt cctcaaggac    2160
cacttcctga tggacgggca ggtccgaagc cgcatgctgc tgctgcagcc caggctcgc     2220 taccagcgcg tggctgtaca ccgcgtccct ggcctgcacc acacctacga tgtcctcttc    2280
ctgggcactg gtgacggccg gctccacaag gcagtgagcg tgggcccccg ggtgcacatc    2340
attgaggagc tgcagatctt ctcatcggga cagcccgtgc agaatctgct cctggacacc    2400 cacgggggg  tgctgtatgc ggcctcacac tcgggcgtag tccaggtgcc catggccaac    2460
tgcagcctgt acaggagctg tggggactgc tcctcgccc  gggacccta  ctgtgcttgg    2520 agcggctcca gctgcaagca cgtcagcctc taccagcctc agctggccac caggccgtgg    2580
atccaggaca tcgagggagc cagcgccaag gacctttgca gcgcgtcttc ggttgtgtcc    2640
ccgtcttttg taccaacagg ggagaagcca tgtgagcaag tccagttcca gcccaacaca    2700
gtgaacactt tggcctgccc gctcctctcc aacctggcga cccgactctg gctacgcaac    2760
ggggcccccg tcaatgcctc ggcctcctgc acgtgctac  ccactgggga cctgctgctg    2820
gtgggcaccc aacagctggg ggagttccag tgctggtcac tagaggaggg cttccagcag    2880
ctggtagcca gctactgccc agaggtggtg gaggacgggg tggcaaacca aacagatgag    2940
ggtggcagtg taccgtcat  tatcagcaca tcgcgtgtga gtgcacccag cacccggctg    3000
```

```
gggcctgtcc ctggatgcag gctactctag                                      3030
```

<210> SEQ ID NO 24
<211> LENGTH: 1009
<212> TYPE: PRT
<213> ORGANISM: homo sapiens

<400> SEQUENCE: 24

| | | | | | | | | | | | | | | |
|---|---|---|---|---|---|---|---|---|---|---|---|---|---|---|
| Met | Leu | Arg | Thr | Ala | Met | Gly | Leu | Arg | Ser | Trp | Leu | Ala | Ala | Pro | Trp |
| 1 | | | | 5 | | | | | 10 | | | | | 15 | |
| Gly | Ala | Leu | Pro | Pro | Arg | Pro | Pro | Leu | Leu | Leu | Leu | Leu | Leu | Leu | Leu |
| | | | 20 | | | | | 25 | | | | | 30 | | |
| Leu | Leu | Leu | Gln | Pro | Pro | Pro | Thr | Trp | Ala | Leu | Ser | Pro | Arg | Ile |
| | | | 35 | | | | 40 | | | | | 45 | | |
| Ser | Leu | Pro | Leu | Gly | Ser | Glu | Arg | Pro | Phe | Leu | Arg | Phe | Glu | Ala |
| | 50 | | | | | 55 | | | | | 60 | | | |
| Glu | His | Ile | Ser | Asn | Tyr | Thr | Ala | Leu | Leu | Ser | Arg | Asp | Gly | Arg |
| 65 | | | | | 70 | | | | | 75 | | | | | 80 |
| Thr | Leu | Tyr | Val | Gly | Ala | Arg | Glu | Ala | Leu | Phe | Ala | Leu | Ser | Ser | Asn |
| | | | | 85 | | | | | 90 | | | | | 95 | |
| Leu | Ser | Phe | Leu | Pro | Gly | Gly | Glu | Tyr | Gln | Glu | Leu | Leu | Trp | Gly | Ala |
| | | | 100 | | | | | 105 | | | | | 110 | | |
| Asp | Ala | Glu | Lys | Lys | Gln | Gln | Cys | Ser | Phe | Lys | Gly | Lys | Asp | Pro | Gln |
| | | | 115 | | | | | 120 | | | | | 125 | | |
| Arg | Asp | Cys | Gln | Asn | Tyr | Ile | Lys | Ile | Leu | Leu | Pro | Leu | Ser | Gly | Ser |
| | 130 | | | | | 135 | | | | | 140 | | | |
| His | Leu | Phe | Thr | Cys | Gly | Thr | Ala | Ala | Phe | Ser | Pro | Met | Cys | Thr | Tyr |
| 145 | | | | | 150 | | | | | 155 | | | | | 160 |
| Ile | Asn | Met | Glu | Asn | Phe | Thr | Leu | Ala | Arg | Asp | Glu | Lys | Gly | Asn | Val |
| | | | | 165 | | | | | 170 | | | | | 175 | |
| Leu | Leu | Glu | Asp | Gly | Lys | Gly | Arg | Cys | Pro | Phe | Asp | Pro | Asn | Phe | Lys |
| | | | 180 | | | | | 185 | | | | | 190 | | |
| Ser | Thr | Ala | Leu | Val | Val | Asp | Gly | Glu | Leu | Tyr | Thr | Gly | Thr | Val | Ser |
| | | | 195 | | | | | 200 | | | | | 205 | | |
| Ser | Phe | Gln | Gly | Asn | Asp | Pro | Ala | Ile | Ser | Arg | Ser | Gln | Ser | Leu | Arg |
| | 210 | | | | | 215 | | | | | 220 | | | |
| Pro | Thr | Lys | Thr | Glu | Ser | Ser | Leu | Asn | Trp | Leu | Gln | Asp | Pro | Ala | Phe |
| 225 | | | | | 230 | | | | | 235 | | | | | 240 |
| Val | Ala | Ser | Ala | Tyr | Ile | Pro | Glu | Ser | Leu | Gly | Ser | Leu | Gln | Gly | Asp |
| | | | | 245 | | | | | 250 | | | | | 255 | |
| Asp | Asp | Lys | Ile | Tyr | Phe | Phe | Ser | Glu | Thr | Gly | Gln | Glu | Phe | Glu |
| | | | 260 | | | | | 265 | | | | | 270 | | |
| Phe | Phe | Glu | Asn | Thr | Ile | Val | Ser | Arg | Ile | Ala | Arg | Ile | Cys | Lys | Gly |
| | | 275 | | | | | 280 | | | | | 285 | | |
| Asp | Glu | Gly | Gly | Glu | Arg | Val | Leu | Gln | Gln | Arg | Trp | Thr | Ser | Phe | Leu |
| | | 290 | | | | | 295 | | | | | 300 | | |
| Lys | Ala | Gln | Leu | Leu | Cys | Ser | Arg | Pro | Asp | Asp | Gly | Phe | Pro | Phe | Asn |
| 305 | | | | | 310 | | | | | 315 | | | | | 320 |
| Val | Leu | Gln | Asp | Val | Phe | Thr | Leu | Ser | Pro | Ser | Pro | Gln | Asp | Trp | Arg |
| | | | | 325 | | | | | 330 | | | | | 335 | |
| Asp | Thr | Leu | Phe | Tyr | Gly | Val | Phe | Thr | Ser | Gln | Trp | His | Arg | Gly | Thr |
| | | | 340 | | | | | 345 | | | | | 350 | | |
| Thr | Glu | Gly | Ser | Ala | Val | Cys | Val | Phe | Thr | Met | Lys | Asp | Val | Gln | Arg |
| | | 355 | | | | | 360 | | | | | 365 | | |

-continued

```
Val Phe Ser Gly Leu Tyr Lys Glu Val Asn Arg Glu Thr Gln Gln Trp
    370                 375                 380
Tyr Thr Val Thr His Pro Val Pro Thr Pro Arg Pro Gly Ala Cys Ile
385                 390                 395                 400
Thr Asn Ser Ala Arg Glu Arg Lys Ile Asn Ser Ser Leu Gln Leu Pro
                405                 410                 415
Asp Arg Val Leu Asn Phe Leu Lys Asp His Phe Leu Met Asp Gly Gln
                420                 425                 430
Val Arg Ser Arg Met Leu Leu Gln Pro Gln Ala Arg Tyr Gln Arg
            435                 440                 445
Val Ala Val His Arg Val Pro Gly Leu His His Thr Tyr Asp Val Leu
    450                 455                 460
Phe Leu Gly Thr Gly Asp Gly Arg Leu His Lys Ala Val Ser Val Gly
465                 470                 475                 480
Pro Arg Val His Ile Ile Glu Glu Leu Gln Ile Phe Ser Ser Gly Gln
                485                 490                 495
Pro Val Gln Asn Leu Leu Leu Asp Thr His Arg Gly Leu Leu Tyr Ala
                500                 505                 510
Ala Ser His Ser Gly Val Val Gln Val Pro Met Ala Asn Cys Ser Leu
            515                 520                 525
Tyr Arg Ser Cys Gly Asp Cys Leu Leu Ala Arg Asp Pro Tyr Cys Ala
    530                 535                 540
Trp Ser Gly Ser Ser Cys Lys His Val Ser Leu Tyr Gln Pro Gln Leu
545                 550                 555                 560
Ala Thr Arg Pro Trp Ile Gln Asp Ile Glu Gly Ala Ser Ala Lys Asp
                565                 570                 575
Leu Cys Ser Ala Ser Ser Val Val Ser Pro Ser Phe Val Pro Thr Gly
                580                 585                 590
Glu Lys Pro Cys Glu Gln Val Gln Phe Gln Pro Asn Thr Val Asn Thr
            595                 600                 605
Leu Ala Cys Pro Leu Leu Ser Asn Leu Ala Thr Arg Leu Trp Leu Arg
    610                 615                 620
Asn Gly Ala Pro Val Asn Ala Ser Ala Ser Cys His Val Leu Pro Thr
625                 630                 635                 640
Gly Asp Leu Leu Leu Val Gly Thr Gln Gln Leu Gly Glu Phe Gln Cys
                645                 650                 655
Trp Ser Leu Glu Glu Gly Phe Gln Gln Leu Val Ala Ser Tyr Cys Pro
                660                 665                 670
Glu Val Val Glu Asp Gly Val Ala Asp Gln Thr Asp Thr Val Pro Thr
            675                 680                 685
Pro Arg Pro Gly Ala Cys Ile Thr Asn Ser Ala Arg Glu Arg Lys Ile
    690                 695                 700
Asn Ser Ser Leu Gln Leu Pro Asp Arg Val Leu Asn Phe Leu Lys Asp
705                 710                 715                 720
His Phe Leu Met Asp Gly Gln Val Arg Ser Arg Met Leu Leu Leu Gln
                725                 730                 735
Pro Gln Ala Arg Tyr Gln Arg Val Ala Val His Arg Val Pro Gly Leu
            740                 745                 750
His His Thr Tyr Asp Val Leu Phe Leu Gly Thr Gly Asp Gly Arg Leu
    755                 760                 765
His Lys Ala Val Ser Val Gly Pro Arg Val His Ile Ile Glu Glu Leu
    770                 775                 780
Gln Ile Phe Ser Ser Gly Gln Pro Val Gln Asn Leu Leu Leu Asp Thr
```

```
                785                 790                 795                 800
His Arg Gly Leu Leu Tyr Ala Ala Ser His Ser Gly Val Val Gln Val
                    805                 810                 815
Pro Met Ala Asn Cys Ser Leu Tyr Arg Ser Cys Gly Asp Cys Leu Leu
                820                 825                 830
Ala Arg Asp Pro Tyr Cys Ala Trp Ser Gly Ser Ser Cys Lys His Val
            835                 840                 845
Ser Leu Tyr Gln Pro Gln Leu Ala Thr Arg Pro Trp Ile Gln Asp Ile
        850                 855                 860
Glu Gly Ala Ser Ala Lys Asp Leu Cys Ser Ala Ser Ser Val Val Ser
865                 870                 875                 880
Pro Ser Phe Val Pro Thr Gly Glu Lys Pro Cys Glu Gln Val Gln Phe
                885                 890                 895
Gln Pro Asn Thr Val Asn Thr Leu Ala Cys Pro Leu Leu Ser Asn Leu
                900                 905                 910
Ala Thr Arg Leu Trp Leu Arg Asn Gly Ala Pro Val Asn Ala Ser Ala
            915                 920                 925
Ser Cys His Val Leu Pro Thr Gly Asp Leu Leu Leu Val Gly Thr Gln
        930                 935                 940
Gln Leu Gly Glu Phe Gln Cys Trp Ser Leu Glu Glu Gly Phe Gln Gln
945                 950                 955                 960
Leu Val Ala Ser Tyr Cys Pro Glu Val Val Glu Asp Gly Val Ala Asn
                965                 970                 975
Gln Thr Asp Glu Gly Gly Ser Val Pro Val Ile Ile Ser Thr Ser Arg
            980                 985                 990
Val Ser Ala Pro Ser Thr Arg Leu Gly Pro Val Pro Gly Cys Arg Leu
        995                 1000                1005
Leu
```

<210> SEQ ID NO 25
<211> LENGTH: 2358
<212> TYPE: DNA
<213> ORGANISM: homo sapiens

<400> SEQUENCE: 25

```
atgctgcgca ccgcgatggg cctgaggagc tggctcgccg ccccatgggg cgcgctgccg      60
cctcggccac cgctgctgct gctcctgctg ctgctgctcc tgctgcagcc gccgcctccg     120
acctgggcgc tcagcccccg gatcagcctg cctctgggct ctgaagagcg ccattcctc     180
agattcgaag ctgaacacat ctccaactac acagcccttc tgctgagcag ggatggcagg     240
accctgtacg tgggtgctcg agaggccctc tttgcactca gtagcaacct cagcttcctg     300
ccaggcgggg agtaccagga gctgctttgg ggtgcagacg cagagaagaa acagcagtgc     360
agcttcaagg gcaaggaccc acagcgcgac tgtcaaaact acatcaagat cctcctgccg     420
ctcagcggca gtcacctgtt cacctgtggc acagcagcct tcagccccat gtgtacctac     480
atcaacatgg agacttcac cctggcaagg gacgagaagg ggaatgtcct cctggaagat     540
ggcaagggcc gttgtccctt cgacccgaat tcaagtcca ctgccctggt ggttgatggc     600
gagctctaca ctggaacagt cagcagcttc aagggaatg accggccat ctcgcggagc     660
caaagccttc gccccaccaa gaccgagagc tccctcaact ggctgcaaga cccagctttt     720
gtggcctcag cctacattcc tgagagcctg gcagcttgc aaggcgatga tgacaagatc     780
tactttttct tcagcgagac tggccaggaa tttgagttct tgagaacac cattgtgtcc     840
```

```
cgcattgccc gcatctgcaa gggcgatgag ggtggagagc gggtgctaca gcagcgctgg    900
acctccttcc tcaaggccca gctgctgtgc tcacggcccg acgatggctt ccccttcaac    960
gtgctgcagg atgtcttcac gctgagcccc agccccagg actggcgtga caccctttc    1020
tatgggtct tcacttccca gtggcacagg ggaactacag aaggctctgc cgtctgtgtc    1080
ttcacaatga aggatgtgca gagagtcttc agcggcctct acaaggaggt gaaccgtgag    1140
acacagcagt ggtacaccgt gacccacccg gtgcccacac cccggcctgg agcgtgcatc    1200
accaacagtg cccgggaaag gaagatcaac tcatccctgc agctcccaga ccgcgtgctg    1260
aacttcctca aggaccactt cctgatggac gggcaggtcc gaagccgcat gctgctgctg    1320
cagccccagg ctcgctacca gcgcgtggct gtacaccgcg tccctggcct gcaccacacc    1380
tacgatgtcc tcttcctggg cactggtgac ggccggctcc acaaggcagt gagcgtgggc    1440
ccccgggtgc acatcattga ggagctgcag atcttctcat cgggacagcc cgtgcagaat    1500
ctgctcctgg acacccacag ggggctgctg tatgcggcct cacactcggg cgtagtccag    1560
gtgcccatgg ccaactgcag cctgtacagg agctgtgggg actgcctcct cgcccgggac    1620
ccctactgtg cttggagcgg ctccagctgc aagcacgtca gcctctacca gcctcagctg    1680
gccaccaggc cgtggatcca ggacatcgag ggagccagcg ccaaggacct ttgcagcgcg    1740
tcttcggttg tgtccccgtc ttttgtacca caggggaga agccatgtga gcaagtccag    1800
ttccagccca acacagtgaa cactttggcc tgcccgctcc tctccaacct ggcgacccga    1860
ctctggctac gcaacggggc ccccgtcaat gcctcggcct cctgccacgt gctacccact    1920
ggggacctgc tgctggtggg cacccaacag ctgggggagt tccagtgctg gtcactagag    1980
gagggcttcc agcagctggt agccagctac tgcccagagg tggtggagga cggggtggca    2040
gaccaaacag atgagggtgg cagtgtaccc gtcattatca gcacatcgcg tgtgagtgca    2100
ccagctggtg gcaaggccag ctggggtgca gacaggtcct actggaagga gttcctggtg    2160
atgtgcacgc tctttgtgct ggccgtgctg ctcccagttt tattcttgct ctaccggcac    2220
cggaacagca tgaaagtctt cctgaagcag ggggaatgtg ccagcgtgca ccccaagacc    2280
tgccctgtgg tgctgccccc tgagacccgc cctcggtttc accgtcaccg ccgacgtcga    2340
ggtgactcaa cggcctag                                                  2358
```

<210> SEQ ID NO 26
<211> LENGTH: 785
<212> TYPE: PRT
<213> ORGANISM: homo sapiens

<400> SEQUENCE: 26

```
Met Leu Arg Thr Ala Met Gly Leu Arg Ser Trp Leu Ala Ala Pro Trp
 1               5                  10                  15

Gly Ala Leu Pro Pro Arg Pro Pro Leu Leu Leu Leu Leu Leu Leu Leu
            20                  25                  30

Leu Leu Leu Gln Pro Pro Pro Thr Trp Ala Leu Ser Pro Arg Ile
        35                  40                  45

Ser Leu Pro Leu Gly Ser Glu Glu Arg Pro Phe Leu Arg Phe Glu Ala
    50                  55                  60

Glu His Ile Ser Asn Tyr Thr Ala Leu Leu Ser Arg Asp Gly Arg
65                  70                  75                  80

Thr Leu Tyr Val Gly Ala Arg Glu Ala Leu Phe Ala Leu Ser Ser Asn
                85                  90                  95

Leu Ser Phe Leu Pro Gly Gly Glu Tyr Gln Glu Leu Leu Trp Gly Ala
```

-continued

```
            100                 105                 110
Asp Ala Glu Lys Lys Gln Gln Cys Ser Phe Lys Gly Lys Asp Pro Gln
        115                 120                 125

Arg Asp Cys Gln Asn Tyr Ile Lys Ile Leu Leu Pro Leu Ser Gly Ser
130                 135                 140

His Leu Phe Thr Cys Gly Thr Ala Ala Phe Ser Pro Met Cys Thr Tyr
145                 150                 155                 160

Ile Asn Met Glu Asn Phe Thr Leu Ala Arg Asp Lys Gly Asn Val
                165                 170                 175

Leu Leu Glu Asp Gly Lys Gly Arg Cys Pro Phe Asp Pro Asn Phe Lys
            180                 185                 190

Ser Thr Ala Leu Val Val Asp Gly Glu Leu Tyr Thr Gly Thr Val Ser
        195                 200                 205

Ser Phe Gln Gly Asn Asp Pro Ala Ile Ser Arg Ser Gln Ser Leu Arg
        210                 215                 220

Pro Thr Lys Thr Glu Ser Ser Leu Asn Trp Leu Gln Asp Pro Ala Phe
225                 230                 235                 240

Val Ala Ser Ala Tyr Ile Pro Glu Ser Leu Gly Ser Leu Gln Gly Asp
                245                 250                 255

Asp Asp Lys Ile Tyr Phe Phe Ser Glu Thr Gly Gln Glu Phe Glu
            260                 265                 270

Phe Phe Glu Asn Thr Ile Val Ser Arg Ile Ala Arg Ile Cys Lys Gly
        275                 280                 285

Asp Glu Gly Gly Glu Arg Val Leu Gln Gln Arg Trp Thr Ser Phe Leu
        290                 295                 300

Lys Ala Gln Leu Leu Cys Ser Arg Pro Asp Asp Gly Phe Pro Phe Asn
305                 310                 315                 320

Val Leu Gln Asp Val Phe Thr Leu Ser Pro Ser Pro Gln Asp Trp Arg
                325                 330                 335

Asp Thr Leu Phe Tyr Gly Val Phe Thr Ser Gln Trp His Arg Gly Thr
            340                 345                 350

Thr Glu Gly Ser Ala Val Cys Val Phe Thr Met Lys Asp Val Gln Arg
        355                 360                 365

Val Phe Ser Gly Leu Tyr Lys Glu Val Asn Arg Glu Thr Gln Gln Trp
370                 375                 380

Tyr Thr Val Thr His Pro Val Pro Thr Pro Arg Pro Gly Ala Cys Ile
385                 390                 395                 400

Thr Asn Ser Ala Arg Glu Arg Lys Ile Asn Ser Ser Leu Gln Leu Pro
                405                 410                 415

Asp Arg Val Leu Asn Phe Leu Lys Asp His Phe Leu Met Asp Gly Gln
            420                 425                 430

Val Arg Ser Arg Met Leu Leu Gln Pro Gln Ala Arg Tyr Gln Arg
        435                 440                 445

Val Ala Val His Arg Val Pro Gly Leu His His Thr Tyr Asp Val Leu
        450                 455                 460

Phe Leu Gly Thr Gly Asp Gly Arg Leu His Lys Ala Val Ser Val Gly
465                 470                 475                 480

Pro Arg Val His Ile Ile Glu Glu Leu Gln Ile Phe Ser Ser Gly Gln
                485                 490                 495

Pro Val Gln Asn Leu Leu Leu Asp Thr His Arg Gly Leu Leu Tyr Ala
            500                 505                 510

Ala Ser His Ser Gly Val Val Gln Val Pro Met Ala Asn Cys Ser Leu
        515                 520                 525
```

| Tyr | Arg | Ser | Cys | Gly | Asp | Cys | Leu | Leu | Ala | Arg | Asp | Pro | Tyr | Cys | Ala |
|-----|-----|-----|-----|-----|-----|-----|-----|-----|-----|-----|-----|-----|-----|-----|-----|
|     | 530 |     |     |     |     | 535 |     |     |     |     | 540 |     |     |     |     |

Trp Ser Gly Ser Ser Cys Lys His Val Ser Leu Tyr Gln Pro Gln Leu
545                 550                 555                 560

Ala Thr Arg Pro Trp Ile Gln Asp Ile Glu Gly Ala Ser Ala Lys Asp
                565                 570                 575

Leu Cys Ser Ala Ser Ser Val Val Ser Pro Ser Phe Val Pro Thr Gly
            580                 585                 590

Glu Lys Pro Cys Glu Gln Val Gln Phe Gln Pro Asn Thr Val Asn Thr
        595                 600                 605

Leu Ala Cys Pro Leu Leu Ser Asn Leu Ala Thr Arg Leu Trp Leu Arg
    610                 615                 620

Asn Gly Ala Pro Val Asn Ala Ser Ala Ser Cys His Val Leu Pro Thr
625                 630                 635                 640

Gly Asp Leu Leu Leu Val Gly Thr Gln Gln Leu Gly Glu Phe Gln Cys
                645                 650                 655

Trp Ser Leu Glu Glu Gly Phe Gln Gln Leu Val Ala Ser Tyr Cys Pro
            660                 665                 670

Glu Val Val Glu Asp Gly Val Ala Asp Gln Thr Asp Glu Gly Gly Ser
        675                 680                 685

Val Pro Val Ile Ile Ser Thr Ser Arg Val Ser Ala Pro Ala Gly Gly
    690                 695                 700

Lys Ala Ser Trp Gly Ala Asp Arg Ser Tyr Trp Lys Glu Phe Leu Val
705                 710                 715                 720

Met Cys Thr Leu Phe Val Leu Ala Val Leu Leu Pro Val Leu Phe Leu
                725                 730                 735

Leu Tyr Arg His Arg Asn Ser Met Lys Val Phe Leu Lys Gln Gly Glu
            740                 745                 750

Cys Ala Ser Val His Pro Lys Thr Cys Pro Val Val Leu Pro Pro Glu
        755                 760                 765

Thr Arg Pro Arg Phe His Arg His Arg Arg Arg Gly Asp Ser Thr
    770                 775                 780

Ala
785

<210> SEQ ID NO 27
<211> LENGTH: 3294
<212> TYPE: DNA
<213> ORGANISM: homo sapiens

<400> SEQUENCE: 27

```
atgctgcgca ccgcgatggg cctgaggagc tggctcgccg ccccatgggg cgcgctgccg      60
cctcggccac cgctgctgct gctcctgctg ctgctgctcc tgctgcagcc gccgcctccg     120
acctgggcgc tcagccccg gatcagcctg cctctgggct ctgaagagcg gccattcctc     180
agattcgaag ctgaacacat ctccaactac acagcccttc tgctgagcag ggatggcagg     240
accctgtacg tgggtgctcg agaggccctc tttgcactca gtagcaacct cagcttcctg     300
ccaggcgggg agtaccagga gctgctttgg ggtgcagacg cagagaagaa acagcagtgc     360
agcttcaagg gcaaggaccc acagcgcgac tgtcaaaact acatcaagat cctcctgccg     420
ctcagcggca gtcacctgtt cacctgtggc acagcagcct tcagccccat gtgtacctac     480
atcaacatgg agaacttcac cctgcaaggg acgagaagg ggaatgtcct cctggaagat     540
ggcaagggcc gttgtccctt cgacccgaat ttcaagtcca ctgccctggt ggttgatggc     600
```

-continued

| | | | | |
|---|---|---|---|---|
| gagctctaca | ctggaacagt | cagcagcttc | caagggaatg | acccggccat ctcgcggagc | 660 |
| caaagccttc | gccccaccaa | gaccgagagc | tccctcaact | ggctgcaaga cccagctttt | 720 |
| gtggcctcag | cctacattcc | tgagagcctg | ggcagcttgc | aaggcgatga tgacaagatc | 780 |
| tactttttct | tcagcgagac | tggccaggaa | tttgagttct | ttgagaacac cattgtgtcc | 840 |
| cgcattgccc | gcatctgcaa | gggcgatgag | ggtggagagc | gggtgctaca gcagcgctgg | 900 |
| acctccttcc | tcaaggccca | gctgctgtgc | tcacggcccg | acgatggctt ccccttcaac | 960 |
| gtgctgcagg | atgtcttcac | gctgagcccc | agccccagg | actggcgtga cacccttttc | 1020 |
| tatggggtct | tcacttccca | gtggcacagg | ggaactacag | aaggctctgc cgtctgtgtc | 1080 |
| ttcacaatga | aggatgtgca | gagagtcttc | agcggcctct | acaaggaggt gaaccgtgag | 1140 |
| acacagcagt | ggtacaccgt | gacccacccg | gtgcccacac | ccggcctgg agcgtgcatc | 1200 |
| accaacagtg | cccgggaaag | gaagatcaac | tcatccctgc | agctcccaga ccgcgtgctg | 1260 |
| aacttcctca | aggaccactt | cctgatggac | gggcaggtcc | gaagccgcat gctgctgctg | 1320 |
| cagccccagg | ctcgctacca | gcgcgtggct | gtacaccgcg | tccctggcct gcaccacacc | 1380 |
| tacgatgtcc | tcttcctggg | cactggtgac | ggccggctcc | acaaggcagt gagcgtgggc | 1440 |
| ccccgggtgc | acatcattga | ggagctgcag | atcttctcat | cgggacagcc cgtgcagaat | 1500 |
| ctgctcctgg | acacccacag | ggggctgctg | tatgcggcct | cacactcggg cgtagtccag | 1560 |
| gtgcccatgg | ccaactgcag | cctgtacagg | agctgtgggg | actgcctcct cgcccgggac | 1620 |
| ccctactgtg | cttggagcgg | ctccagctgc | aagcacgtca | gcctctacca gcctcagctg | 1680 |
| gccaccaggc | cgtggatcca | ggacatcgag | ggagccagcg | ccaaggacct ttgcagcgcg | 1740 |
| tcttcggttg | tgtccccgtc | ttttgtacca | acagggagaa | agccatgtga gcaagtccag | 1800 |
| ttccagccca | acacagtgaa | cactttggcc | tgcccgctcc | tctccaacct ggcgacccga | 1860 |
| ctctggctac | gcaacgggc | ccccgtcaat | gcctcggcct | cctgccacgt gctacccact | 1920 |
| ggggacctgc | tgctggtggg | cacccaacag | ctgggggagt | tccagtgctg gtcactagag | 1980 |
| gagggcttcc | agcagctggt | agccagctac | tgcccagagg | tggtggagga cggggtggca | 2040 |
| gaccaaacag | atacggtgcc | cacacccgg | cctggagcgt | gcatcaccaa cagtgcccgg | 2100 |
| gaaaggaaga | tcaactcatc | cctgcagctc | ccagaccgcg | tgctgaactt cctcaaggac | 2160 |
| cacttcctga | tggacgggca | ggtccgaagc | cgcatgctgc | tgctgcagcc ccaggctcgc | 2220 |
| taccagcgcg | tggctgtaca | ccgcgtccct | ggcctgcacc | acacctacga tgtcctcttc | 2280 |
| ctgggcactg | gtgacggccg | gctccacaag | gcagtgagcg | tgggcccccg ggtgcacatc | 2340 |
| attgaggagc | tgcagatctt | ctcatcggga | cagcccgtgc | agaatctgct cctggacacc | 2400 |
| cacagggggc | tgctgtatgc | ggcctcacac | tcgggcgtag | tccaggtgcc catggccaac | 2460 |
| tgcagcctgt | acaggagctg | tggggactgc | ctcctcgccc | gggaccccta ctgtgcttgg | 2520 |
| agcggctcca | gctgcaagca | cgtcagcctc | taccagcctc | agctggccac caggccgtgg | 2580 |
| atccaggaca | tcgagggagc | cagcgccaag | gacctttgca | gcgcgtcttc ggttgtgtcc | 2640 |
| ccgtcttttg | taccaacagg | ggagaagcca | tgtgagcaag | tccagttcca gcccaacaca | 2700 |
| gtgaacactt | tggcctgccc | gctcctctcc | aacctggcga | cccgactctg gctacgcaac | 2760 |
| ggggcccccg | tcaatgcctc | ggcctcctgc | cacgtgctac | ccactgggga cctgctgctg | 2820 |
| gtgggcaccc | aacagctggg | ggagttccag | tgctggtcac | tagaggaggg cttccagcag | 2880 |
| ctggtagcca | gctactgccc | agaggtggtg | gaggacgggg | tggcaaacca aacagatgag | 2940 |

-continued

```
ggtggcagtg tacccgtcat tatcagcaca tcgcgtgtga gtgcaccagc tggtggcaag   3000
gccagctggg gtgcagacag gtcctactgg aaggagttcc tggtgatgtg cacgctcttt   3060
gtgctggccg tgctgctccc agttttattc ttgctctacc ggcaccggaa cagcatgaaa   3120
gtcttcctga agcaggggga atgtgccagc gtgcaccccca agacctgccc tgtggtgctg   3180 cccctgaga cccgccctcg gtttcaccgt caccgccgac gtcgaggtgc ccgaaggacc   3240 gcgcacctg tgcatgaccc gcaagcccgg tgcctgaagc ggatccagac atga          3294
```

<210> SEQ ID NO 28
<211> LENGTH: 1097
<212> TYPE: PRT
<213> ORGANISM: homo sapiens

<400> SEQUENCE: 28

```
Met Leu Arg Thr Ala Met Gly Leu Arg Ser Trp Leu Ala Ala Pro Trp
  1               5                  10                  15

Gly Ala Leu Pro Pro Arg Pro Pro Leu Leu Leu Leu Leu Leu Leu Leu
                 20                  25                  30

Leu Leu Leu Gln Pro Pro Pro Thr Trp Ala Leu Ser Pro Arg Ile
             35                  40                  45

Ser Leu Pro Leu Gly Ser Glu Glu Arg Pro Phe Leu Arg Phe Glu Ala
 50                  55                  60

Glu His Ile Ser Asn Tyr Thr Ala Leu Leu Leu Ser Arg Asp Gly Arg
 65                  70                  75                  80

Thr Leu Tyr Val Gly Ala Arg Glu Ala Leu Phe Ala Leu Ser Ser Asn
                 85                  90                  95

Leu Ser Phe Leu Pro Gly Gly Glu Tyr Gln Glu Leu Leu Trp Gly Ala
            100                 105                 110

Asp Ala Glu Lys Lys Gln Gln Cys Ser Phe Lys Gly Lys Asp Pro Gln
        115                 120                 125

Arg Asp Cys Gln Asn Tyr Ile Lys Ile Leu Leu Pro Leu Ser Gly Ser
130                 135                 140

His Leu Phe Thr Cys Gly Thr Ala Ala Phe Ser Pro Met Cys Thr Tyr
145                 150                 155                 160

Ile Asn Met Glu Asn Phe Thr Leu Ala Arg Asp Glu Lys Gly Asn Val
                165                 170                 175

Leu Leu Glu Asp Gly Lys Gly Arg Cys Pro Phe Asp Pro Asn Phe Lys
            180                 185                 190

Ser Thr Ala Leu Val Val Asp Gly Glu Leu Tyr Thr Gly Thr Val Ser
        195                 200                 205

Ser Phe Gln Gly Asn Asp Pro Ala Ile Ser Arg Ser Gln Ser Leu Arg
    210                 215                 220

Pro Thr Lys Thr Glu Ser Ser Leu Asn Trp Leu Gln Asp Pro Ala Phe
225                 230                 235                 240

Val Ala Ser Ala Tyr Ile Pro Glu Ser Leu Gly Ser Leu Gln Gly Asp
                245                 250                 255

Asp Asp Lys Ile Tyr Phe Phe Ser Glu Thr Gly Gln Glu Phe
            260                 265                 270

Phe Phe Glu Asn Thr Ile Val Ser Arg Ile Ala Arg Ile Cys Lys Gly
        275                 280                 285

Asp Glu Gly Gly Glu Arg Val Leu Gln Gln Arg Trp Thr Ser Phe Leu
    290                 295                 300

Lys Ala Gln Leu Leu Cys Ser Arg Pro Asp Asp Gly Phe Pro Phe Asn
305                 310                 315                 320
```

```
Val Leu Gln Asp Val Phe Thr Leu Ser Pro Ser Pro Gln Asp Trp Arg
            325                 330                 335

Asp Thr Leu Phe Tyr Gly Val Phe Thr Ser Gln Trp His Arg Gly Thr
            340                 345                 350

Thr Glu Gly Ser Ala Val Cys Val Phe Thr Met Lys Asp Val Gln Arg
            355                 360                 365

Val Phe Ser Gly Leu Tyr Lys Glu Val Asn Arg Glu Thr Gln Gln Trp
            370                 375                 380

Tyr Thr Val Thr His Pro Val Pro Thr Pro Arg Pro Gly Ala Cys Ile
385                 390                 395                 400

Thr Asn Ser Ala Arg Glu Arg Lys Ile Asn Ser Ser Leu Gln Leu Pro
            405                 410                 415

Asp Arg Val Leu Asn Phe Leu Lys Asp His Phe Leu Met Asp Gly Gln
            420                 425                 430

Val Arg Ser Arg Met Leu Leu Leu Gln Pro Gln Ala Arg Tyr Gln Arg
            435                 440                 445

Val Ala Val His Arg Val Pro Gly Leu His His Thr Tyr Asp Val Leu
450                 455                 460

Phe Leu Gly Thr Gly Asp Gly Arg Leu His Lys Ala Val Ser Val Gly
465                 470                 475                 480

Pro Arg Val His Ile Ile Glu Glu Leu Gln Ile Phe Ser Ser Gly Gln
            485                 490                 495

Pro Val Gln Asn Leu Leu Leu Asp Thr His Arg Gly Leu Leu Tyr Ala
            500                 505                 510

Ala Ser His Ser Gly Val Val Gln Val Pro Met Ala Asn Cys Ser Leu
            515                 520                 525

Tyr Arg Ser Cys Gly Asp Cys Leu Leu Ala Arg Asp Pro Tyr Cys Ala
            530                 535                 540

Trp Ser Gly Ser Ser Cys Lys His Val Ser Leu Tyr Gln Pro Gln Leu
545                 550                 555                 560

Ala Thr Arg Pro Trp Ile Gln Asp Ile Glu Gly Ala Ser Ala Lys Asp
            565                 570                 575

Leu Cys Ser Ala Ser Ser Val Val Ser Pro Ser Phe Val Pro Thr Gly
            580                 585                 590

Glu Lys Pro Cys Glu Gln Val Gln Phe Gln Pro Asn Thr Val Asn Thr
            595                 600                 605

Leu Ala Cys Pro Leu Leu Ser Asn Leu Ala Thr Arg Leu Trp Leu Arg
            610                 615                 620

Asn Gly Ala Pro Val Asn Ala Ser Ala Ser Cys His Val Leu Pro Thr
625                 630                 635                 640

Gly Asp Leu Leu Leu Val Gly Thr Gln Gln Leu Gly Glu Phe Gln Cys
            645                 650                 655

Trp Ser Leu Glu Glu Gly Phe Gln Gln Leu Val Ala Ser Tyr Cys Pro
            660                 665                 670

Glu Val Val Glu Asp Gly Val Ala Asp Gln Thr Asp Thr Val Pro Thr
            675                 680                 685

Pro Arg Pro Gly Ala Cys Ile Thr Asn Ser Ala Arg Glu Arg Lys Ile
            690                 695                 700

Asn Ser Ser Leu Gln Leu Pro Asp Arg Val Leu Asn Phe Leu Lys Asp
705                 710                 715                 720

His Phe Leu Met Asp Gly Gln Val Arg Ser Arg Met Leu Leu Leu Gln
                        725                 730                 735
```

```
Pro Gln Ala Arg Tyr Gln Arg Val Ala Val His Arg Val Pro Gly Leu
            740                 745                 750
His His Thr Tyr Asp Val Leu Phe Leu Gly Thr Gly Asp Gly Arg Leu
        755                 760                 765
His Lys Ala Val Ser Val Gly Pro Arg Val His Ile Ile Glu Glu Leu
    770                 775                 780
Gln Ile Phe Ser Ser Gly Gln Pro Val Gln Asn Leu Leu Leu Asp Thr
785                 790                 795                 800
His Arg Gly Leu Leu Tyr Ala Ala Ser His Ser Gly Val Val Gln Val
                805                 810                 815
Pro Met Ala Asn Cys Ser Leu Tyr Arg Ser Cys Gly Asp Cys Leu Leu
            820                 825                 830
Ala Arg Asp Pro Tyr Cys Ala Trp Ser Gly Ser Ser Cys Lys His Val
        835                 840                 845
Ser Leu Tyr Gln Pro Gln Leu Ala Thr Arg Pro Trp Ile Gln Asp Ile
    850                 855                 860
Glu Gly Ala Ser Ala Lys Asp Leu Cys Ser Ala Ser Ser Val Val Ser
865                 870                 875                 880
Pro Ser Phe Val Pro Thr Gly Glu Lys Pro Cys Glu Gln Val Gln Phe
                885                 890                 895
Gln Pro Asn Thr Val Asn Thr Leu Ala Cys Pro Leu Leu Ser Asn Leu
            900                 905                 910
Ala Thr Arg Leu Trp Leu Arg Asn Gly Ala Pro Val Asn Ala Ser Ala
        915                 920                 925
Ser Cys His Val Leu Pro Thr Gly Asp Leu Leu Val Gly Thr Gln
    930                 935                 940
Gln Leu Gly Glu Phe Gln Cys Trp Ser Leu Glu Glu Gly Phe Gln Gln
945                 950                 955                 960
Leu Val Ala Ser Tyr Cys Pro Glu Val Val Glu Asp Gly Val Ala Asn
                965                 970                 975
Gln Thr Asp Glu Gly Gly Ser Val Pro Val Ile Ile Ser Thr Ser Arg
            980                 985                 990
Val Ser Ala Pro Ala Gly Gly Lys Ala Ser Trp Gly Ala Asp Arg Ser
        995                 1000                1005
Tyr Trp Lys Glu Phe Leu Val Met Cys Thr Leu Phe Val Leu Ala Val
    1010                1015                1020
Leu Leu Pro Val Leu Phe Leu Leu Tyr Arg His Arg Asn Ser Met Lys
1025                1030                1035                1040
Val Phe Leu Lys Gln Gly Glu Cys Ala Ser Val His Pro Lys Thr Cys
                1045                1050                1055
Pro Val Val Leu Pro Pro Glu Thr Arg Pro Arg Phe His Arg His Arg
            1060                1065                1070
Arg Arg Arg Gly Ala Arg Arg Thr Ala His Leu Val His Asp Pro Gln
        1075                1080                1085
Ala Arg Cys Leu Lys Arg Ile Gln Thr
    1090                1095
```

<210> SEQ ID NO 29
<211> LENGTH: 2433
<212> TYPE: DNA
<213> ORGANISM: homo sapiens

<400> SEQUENCE: 29
atgctgcgca ccgcgatggg cctgaggagc tggctcgccg ccccatgggg cgcgctgccg    60

-continued

| | |
|---|---|
| cctcggccac cgctgctgct gctcctgctg ctgctgctcc tgctgcagcc gccgcctccg | 120 |
| acctgggcgc tcagccccg gatcagcctg cctctgggct ctgaagagcg gccattcctc | 180 |
| agattcgaag ctgaacacat ctccaactac acagcccttc tgctgagcag ggatggcagg | 240 |
| accctgtacg tgggtgctcg agaggccctc tttgcactca gtagcaacct cagcttcctg | 300 |
| ccaggcgggg agtaccagga gctgctttgg ggtgcagacg cagagaagaa acagcagtgc | 360 |
| agcttcaagg gcaaggaccc acagcgcgac tgtcaaaact acatcaagat cctcctgccg | 420 |
| ctcagcggca gtcacctgtt cacctgtggc acagcagcct tcagcccat gtgtacctac | 480 |
| atcaacatgg agaacttcac cctggcaagg gacgagaagg ggaatgtcct cctggaagat | 540 |
| ggcaagggcc gttgtccctt cgacccgaat ttcaagtcca ctgccctggt ggttgatggc | 600 |
| gagctctaca ctggaacagt cagcagcttc aagggaatg acccggccat ctcgcggagc | 660 |
| caaagccttc gccccaccaa gaccgagagc tccctcaact ggctgcaaga cccagctttt | 720 |
| gtggcctcag cctacattcc tgagagcctg gcagcttgc aaggcgatga tgacaagatc | 780 |
| tactttttct tcagcgagac tggccaggaa tttgagttct tgagaacac cattgtgtcc | 840 |
| cgcattgccc gcatctgcaa gggcgatgag ggtggagagc gggtgctaca gcagcgctgg | 900 |
| acctccttcc tcaaggccca gctgctgtgc tcacggcccg acgatggctt ccccttcaac | 960 |
| gtgctgcagg atgtcttcac gctgagcccc agccccagg actggcgtga cacccttttc | 1020 |
| tatgggtct tcacttccca gtggcacagg ggaactacag aaggctctgc cgtctgtgtc | 1080 |
| ttcacaatga aggatgtgca gagagtcttc agcggcctct acaaggaggt gaaccgtgag | 1140 |
| acacagcagt ggtacaccgt gacccacccg gtgcccacac cccggcctgg agcgtgcatc | 1200 |
| accaacagtg cccgggaaag gaagatcaac tcatccctgc agctcccaga ccgcgtgctg | 1260 |
| aacttcctca aggaccactt cctgatggac gggcaggtcc gaagccgcat gctgctgctg | 1320 |
| cagccccagg ctcgctacca gcgcgtggct gtacaccgcg tccctggcct gcaccacacc | 1380 |
| tacgatgtcc tcttcctggg cactggtgac ggccggctcc acaaggcagt gagcgtgggc | 1440 |
| ccccgggtgc acatcattga ggagctgcag atcttctcat cgggacagcc cgtgcagaat | 1500 |
| ctgctcctgg acacccacag ggggctgctg tatgcggcct cacactcggg cgtagtccag | 1560 |
| gtgcccatgg ccaactgcag cctgtacagg agctgtgggg actgcctcct cgcccgggac | 1620 |
| ccctactgtg cttggagcgg ctccagctgc aagcacgtca gcctctacca gcctcagctg | 1680 |
| gccaccaggc cgtggatcca ggacatcgag ggagccagcg ccaaggacct ttgcagcgcg | 1740 |
| tcttcggttg tgtccccgtc ttttgtacca acagggggaga agccatgtga gcaagtccag | 1800 |
| ttccagccca acacagtgaa cactttggcc tgcccgctcc tctccaacct ggcgacccga | 1860 |
| ctctggctac gcaacggggc ccccgtcaat gcctcggcct cctgccacgt gctacccact | 1920 |
| ggggacctgc tgctggtggg cacccaacag ctgggggagt tccagtgctg gtcactagag | 1980 |
| gagggcttcc agcagctggt agccagctac tgcccagagg tggtgaggga cggggtggca | 2040 |
| gaccaaacag atgagggtgg cagtgtaccc gtcattatca gcacatcgcg tgtgagtgca | 2100 |
| ccagctggtg gcaaggccag ctggggtgca gacaggtcct actggaagga gttcctggtg | 2160 |
| atgtgcacgc tctttgtgct ggccgtgctg ctcccagttt tattcttgct ctaccggcac | 2220 |
| cggaacagca tgaaagtctt cctgaagcag ggggaatgtg ccagcgtgca ccccaagacc | 2280 |
| tgccctgtgg tgctgccccc tgagacccgc ccactcaacg gcctagggcc cctagcacc | 2340 |
| ccgctcgatc accgagggta ccagtccccc cgaaggaccg cgcacctggt gcatgacccg | 2400 |
| caagcccggt gcctgaagcg gatccagaca tga | 2433 |

```
<210> SEQ ID NO 30
<211> LENGTH: 810
<212> TYPE: PRT
<213> ORGANISM: homo sapiens

<400> SEQUENCE: 30

Met Leu Arg Thr Ala Met Gly Leu Arg Ser Trp Leu Ala Ala Pro Trp
 1               5                  10                  15

Gly Ala Leu Pro Pro Arg Pro Pro Leu Leu Leu Leu Leu Leu Leu Leu
             20                  25                  30

Leu Leu Leu Gln Pro Pro Pro Thr Trp Ala Leu Ser Pro Arg Ile
         35                  40                  45

Ser Leu Pro Leu Gly Ser Glu Glu Arg Pro Phe Leu Arg Phe Glu Ala
     50                  55                  60

Glu His Ile Ser Asn Tyr Thr Ala Leu Leu Ser Arg Asp Gly Arg
 65                  70                  75                  80

Thr Leu Tyr Val Gly Ala Arg Glu Ala Leu Phe Ala Leu Ser Ser Asn
                 85                  90                  95

Leu Ser Phe Leu Pro Gly Gly Glu Tyr Gln Glu Leu Leu Trp Gly Ala
                100                 105                 110

Asp Ala Glu Lys Lys Gln Gln Cys Ser Phe Lys Gly Lys Asp Pro Gln
            115                 120                 125

Arg Asp Cys Gln Asn Tyr Ile Lys Ile Leu Leu Pro Leu Ser Gly Ser
        130                 135                 140

His Leu Phe Thr Cys Gly Thr Ala Ala Phe Ser Pro Met Cys Thr Tyr
145                 150                 155                 160

Ile Asn Met Glu Asn Phe Thr Leu Ala Arg Asp Glu Lys Gly Asn Val
                165                 170                 175

Leu Leu Glu Asp Gly Lys Gly Arg Cys Pro Phe Asp Pro Asn Phe Lys
            180                 185                 190

Ser Thr Ala Leu Val Val Asp Gly Glu Leu Tyr Thr Gly Thr Val Ser
        195                 200                 205

Ser Phe Gln Gly Asn Asp Pro Ala Ile Ser Arg Ser Gln Ser Leu Arg
    210                 215                 220

Pro Thr Lys Thr Glu Ser Ser Leu Asn Trp Leu Gln Asp Pro Ala Phe
225                 230                 235                 240

Val Ala Ser Ala Tyr Ile Pro Glu Ser Leu Gly Ser Leu Gln Gly Asp
                245                 250                 255

Asp Asp Lys Ile Tyr Phe Phe Ser Glu Thr Gly Gln Glu Phe Glu
            260                 265                 270

Phe Phe Glu Asn Thr Ile Val Ser Arg Ile Ala Arg Ile Cys Lys Gly
        275                 280                 285

Asp Glu Gly Gly Glu Arg Val Leu Gln Gln Arg Trp Thr Ser Phe Leu
    290                 295                 300

Lys Ala Gln Leu Leu Cys Ser Arg Pro Asp Asp Gly Phe Pro Phe Asn
305                 310                 315                 320

Val Leu Gln Asp Val Phe Thr Leu Ser Pro Ser Pro Gln Asp Trp Arg
                325                 330                 335

Asp Thr Leu Phe Tyr Gly Val Phe Thr Ser Gln Trp His Arg Gly Thr
            340                 345                 350

Thr Glu Gly Ser Ala Val Cys Val Phe Thr Met Lys Asp Val Gln Arg
        355                 360                 365

Val Phe Ser Gly Leu Tyr Lys Glu Val Asn Arg Glu Thr Gln Gln Trp
```

-continued

```
            370                 375                 380
Tyr Thr Val Thr His Pro Val Pro Thr Pro Arg Pro Gly Ala Cys Ile
385                 390                 395                 400

Thr Asn Ser Ala Arg Glu Arg Lys Ile Asn Ser Ser Leu Gln Leu Pro
                405                 410                 415

Asp Arg Val Leu Asn Phe Leu Lys Asp His Phe Leu Met Asp Gly Gln
            420                 425                 430

Val Arg Ser Arg Met Leu Leu Gln Pro Gln Ala Arg Tyr Gln Arg
            435                 440                 445

Val Ala Val His Arg Val Pro Gly Leu His His Thr Tyr Asp Val Leu
450                 455                 460

Phe Leu Gly Thr Gly Asp Gly Arg Leu His Lys Ala Val Ser Val Gly
465                 470                 475                 480

Pro Arg Val His Ile Ile Glu Glu Leu Gln Ile Phe Ser Ser Gly Gln
                485                 490                 495

Pro Val Gln Asn Leu Leu Leu Asp Thr His Arg Gly Leu Leu Tyr Ala
            500                 505                 510

Ala Ser His Ser Gly Val Val Gln Val Pro Met Ala Asn Cys Ser Leu
            515                 520                 525

Tyr Arg Ser Cys Gly Asp Cys Leu Leu Ala Arg Asp Pro Tyr Cys Ala
            530                 535                 540

Trp Ser Gly Ser Ser Cys Lys His Val Ser Leu Tyr Gln Pro Gln Leu
545                 550                 555                 560

Ala Thr Arg Pro Trp Ile Gln Asp Ile Glu Gly Ala Ser Ala Lys Asp
                565                 570                 575

Leu Cys Ser Ala Ser Ser Val Val Ser Pro Ser Phe Val Pro Thr Gly
            580                 585                 590

Glu Lys Pro Cys Glu Gln Val Gln Phe Gln Pro Asn Thr Val Asn Thr
                595                 600                 605

Leu Ala Cys Pro Leu Leu Ser Asn Leu Ala Thr Arg Leu Trp Leu Arg
            610                 615                 620

Asn Gly Ala Pro Val Asn Ala Ser Ala Ser Cys His Val Leu Pro Thr
625                 630                 635                 640

Gly Asp Leu Leu Leu Val Gly Thr Gln Gln Leu Gly Glu Phe Gln Cys
                645                 650                 655

Trp Ser Leu Glu Glu Gly Phe Gln Gln Leu Val Ala Ser Tyr Cys Pro
                660                 665                 670

Glu Val Val Glu Asp Gly Val Ala Asp Gln Thr Asp Glu Gly Gly Ser
            675                 680                 685

Val Pro Val Ile Ile Ser Thr Ser Arg Val Ser Ala Pro Ala Gly Gly
690                 695                 700

Lys Ala Ser Trp Gly Ala Asp Arg Ser Tyr Trp Lys Glu Phe Leu Val
705                 710                 715                 720

Met Cys Thr Leu Phe Val Leu Ala Val Leu Leu Pro Val Leu Phe Leu
                725                 730                 735

Leu Tyr Arg His Arg Asn Ser Met Lys Val Phe Leu Lys Gln Gly Glu
            740                 745                 750

Cys Ala Ser Val His Pro Lys Thr Cys Pro Val Val Leu Pro Pro Glu
            755                 760                 765

Thr Arg Pro Leu Asn Gly Leu Gly Pro Pro Ser Thr Pro Leu Asp His
770                 775                 780

Arg Gly Tyr Gln Ser Pro Arg Arg Thr Ala His Leu Val His Asp Pro
785                 790                 795                 800
```

Gln Ala Arg Cys Leu Lys Arg Ile Gln Thr
          805                    810

<210> SEQ ID NO 31
<211> LENGTH: 3318
<212> TYPE: DNA
<213> ORGANISM: homo sapiens

<400> SEQUENCE: 31

| | | | | | |
|---|---|---|---|---|---|
| atgctgcgca | ccgcgatggg | cctgaggagc | tggctcgccg | ccccatgggg cgcgctgccg | 60 |
| cctcggccac | cgctgctgct | gctcctgctg | ctgctgctcc | tgctgcagcc gccgcctccg | 120 |
| acctgggcgc | tcagccccg | gatcagcctg | cctctgggct | ctgaagagcg gccattcctc | 180 |
| agattcgaag | ctgaacacat | ctccaactac | acagcccttc | tgctgagcag ggatggcagg | 240 |
| accctgtacg | tgggtgctcg | agaggccctc | tttgcactca | gtagcaacct cagcttcctg | 300 |
| ccaggcgggg | agtaccagga | gctgctttgg | ggtgcagacg | cagagaagaa acagcagtgc | 360 |
| agcttcaagg | gcaaggaccc | acagcgcgac | tgtcaaaact | acatcaagat cctcctgccg | 420 |
| ctcagcggca | gtcacctgtt | cacctgtggc | acagcagcct | tcagcccat gtgtacctac | 480 |
| atcaacatgg | agaacttcac | cctggcaagg | gacgagaagg | ggaatgtcct cctggaagat | 540 |
| ggcaagggcc | gttgtccctt | cgacccgaat | ttcaagtcca | ctgccctggt ggttgatggc | 600 |
| gagctctaca | ctgaacagt | cagcagcttc | caagggaatg | accggccat ctcgcggagc | 660 |
| caaagccttc | gccccaccaa | gaccgagagc | tccctcaact | ggctgcaaga cccagctttt | 720 |
| gtggcctcag | cctacattcc | tgagagcctg | gcagcttgc | aaggcgatga tgacaagatc | 780 |
| tactttttct | tcagcgagac | tggccaggaa | tttgagttct | tgagaacac cattgtgtcc | 840 |
| cgcattgccc | gcatctgcaa | gggcgatgag | ggtggagagc | gggtgctaca gcagcgctgg | 900 |
| acctccttcc | tcaaggccca | gctgctgtgc | tcacggcccg | acgatggctt ccccttcaac | 960 |
| gtgctgcagg | atgtcttcac | gctgagcccc | agccccagg | actggcgtga caccctttc | 1020 |
| tatgggtgtct | tcacttccca | gtggcacagg | ggaactacag | aaggctctgc cgtctgtgtc | 1080 |
| ttcacaatga | aggatgtgca | gagagtcttc | agcggcctct | acaaggaggt gaaccgtgag | 1140 |
| acacagcagt | ggtacaccgt | gacccacccg | gtgcccacac | ccggcctgg agcgtgcatc | 1200 |
| accaacagtg | cccgggaaag | gaagatcaac | tcatccctgc | agctcccaga ccgcgtgctg | 1260 |
| aacttcctca | aggaccactt | cctgatggac | gggcaggtcc | gaagccgcat gctgctgctg | 1320 |
| cagccccagg | ctcgctacca | gcgcgtggct | gtacaccgcg | tccctggcct gcaccacacc | 1380 |
| tacgatgtcc | tcttcctggg | cactggtgac | ggccggctcc | acaaggcagt gagcgtgggc | 1440 |
| cccccgggtgc | acatcattga | ggagctgcag | atcttctcat | cgggacagcc cgtgcagaat | 1500 |
| ctgctcctgg | acacccacag | gggctgctg | tatgcggcct | cacactcggg cgtagtccag | 1560 |
| gtgcccatgg | ccaactgcag | cctgtacagg | agctgtgggg | actgcctcct cgcccggac | 1620 |
| ccctactgtg | cttggagcgg | ctccagctgc | aagcacgtca | gcctctacca gcctcagctg | 1680 |
| gccaccaggc | cgtggatcca | ggacatcgag | ggagccagcg | ccaaggacct ttgcagcgcg | 1740 |
| tcttcggttg | tgtccccgtc | ttttgtacca | acagggagaa | agccatgtga gcaagtccag | 1800 |
| ttccagccca | acacagtgaa | cactttggcc | tgccgctcc | tctccaacct ggcgacccga | 1860 |
| ctctggctac | gcaacggggc | cccgtcaat | gcctcggcct | cctgccacgt gctacccact | 1920 |
| ggggacctgc | tgctggtggg | cacccaacag | ctggggagt | tccagtgctg gtcactagag | 1980 |
| gagggcttcc | agcagctggt | agccagctac | tgcccagagg | tggtggagga cggggtggca | 2040 |

-continued

```
gaccaaacag atacggtgcc cacaccccgg cctggagcgt gcatcaccaa cagtgcccgg    2100
gaaaggaaga tcaactcatc cctgcagctc ccagaccgcg tgctgaactt cctcaaggac    2160
cacttcctga tggacgggca ggtccgaagc cgcatgctgc tgctgcagcc caggctcgc     2220 taccagcgcg tggctgtaca ccgcgtccct ggcctgcacc acacctacga tgtcctcttc    2280
ctgggcactg gtgacggccg gctccacaag gcagtgagcg tgggccccg ggtgcacatc     2340 attgaggagc tgcagatctt ctcatcggga cagcccgtgc agaatctgct cctggacacc    2400 cacaggggc tgctgtatgc ggcctcacac tcgggcgtag tccaggtgcc catggccaac     2460
tgcagcctgt acaggagctg tggggactgc ctcctcgccc gggacccta ctgtgcttgg     2520 agcggctcca gctgcaagca cgtcagcctc taccagcctc agctggccac caggccgtgg    2580
atccaggaca tcgagggagc cagcgccaag gacctttgca gcgcgtcttc ggttgtgtcc    2640
ccgtcttttg taccaacagg ggagaagcca tgtgagcaag tccagttcca gcccaacaca    2700
gtgaacactt tggcctgccc gctcctctcc aacctggcga cccgactctg gctacgcaac    2760 ggggccccg tcaatgcctc ggcctcctgc cacgtgctac ccactgggga cctgctgctg    2820
gtgggcaccc aacagctggg ggagttccag tgctggtcac tagaggaggg cttccagcag    2880
ctggtagcca gctactgccc agaggtggtg gaggacgggg tggcaaacca aacagatgag    2940
ggtggcagtg tacccgtcat tatcagcaca tcgcgtgtga gtgcaccagc tggtggcaag    3000
gccagctggg gtgcagacag gtcctactgg aaggagttcc tggtgatgtg cacgctcttt    3060
gtgctggccg tgctgctccc agtttttattc ttgctctacc ggcaccggaa cagcatgaaa    3120
gtcttcctga gcaggggga atgtgccagc gtgcacccca agacctgccc tgtggtgctg    3180 cccccctgaga cccgcccact caacggccta ggggccccta gcaccccgct cgatcaccga    3240
gggtaccagt ccccccgaag gaccgcgcac ctggtgcatg acccgcaagc ccggtgcctg    3300
aagcggatcc agacatga                                                  3318
```

<210> SEQ ID NO 32
<211> LENGTH: 1105
<212> TYPE: PRT
<213> ORGANISM: homo sapiens

<400> SEQUENCE: 32

```
Met Leu Arg Thr Ala Met Gly Leu Arg Ser Trp Leu Ala Ala Pro Trp
 1               5                  10                  15

Gly Ala Leu Pro Pro Arg Pro Pro Leu Leu Leu Leu Leu Leu Leu Leu
                20                  25                  30

Leu Leu Leu Gln Pro Pro Pro Thr Trp Ala Leu Ser Pro Arg Ile
            35                  40                  45

Ser Leu Pro Leu Gly Ser Glu Glu Arg Pro Phe Leu Arg Phe Glu Ala
 50                  55                  60

Glu His Ile Ser Asn Tyr Thr Ala Leu Leu Ser Arg Asp Gly Arg
 65                  70                  75                  80

Thr Leu Tyr Val Gly Ala Arg Glu Ala Leu Phe Ala Leu Ser Ser Asn
                85                  90                  95

Leu Ser Phe Leu Pro Gly Gly Glu Tyr Gln Glu Leu Leu Trp Gly Ala
            100                 105                 110

Asp Ala Glu Lys Lys Gln Gln Cys Ser Phe Lys Gly Lys Asp Pro Gln
        115                 120                 125

Arg Asp Cys Gln Asn Tyr Ile Lys Ile Leu Leu Pro Leu Ser Gly Ser
    130                 135                 140
```

```
His Leu Phe Thr Cys Gly Thr Ala Ala Phe Ser Pro Met Cys Thr Tyr
145                 150                 155                 160

Ile Asn Met Glu Asn Phe Thr Leu Ala Arg Asp Glu Lys Gly Asn Val
            165                 170                 175

Leu Leu Glu Asp Gly Lys Gly Arg Cys Pro Phe Asp Pro Asn Phe Lys
            180                 185                 190

Ser Thr Ala Leu Val Val Asp Gly Glu Leu Tyr Thr Gly Thr Val Ser
            195                 200                 205

Ser Phe Gln Gly Asn Asp Pro Ala Ile Ser Arg Ser Gln Ser Leu Arg
            210                 215                 220

Pro Thr Lys Thr Glu Ser Ser Leu Asn Trp Leu Gln Asp Pro Ala Phe
225                 230                 235                 240

Val Ala Ser Ala Tyr Ile Pro Glu Ser Leu Gly Ser Leu Gln Gly Asp
            245                 250                 255

Asp Asp Lys Ile Tyr Phe Phe Ser Glu Thr Gly Gln Glu Phe Glu
            260                 265                 270

Phe Phe Glu Asn Thr Ile Val Ser Arg Ile Ala Arg Ile Cys Lys Gly
            275                 280                 285

Asp Glu Gly Gly Glu Arg Val Leu Gln Gln Arg Trp Thr Ser Phe Leu
290                 295                 300

Lys Ala Gln Leu Leu Cys Ser Arg Pro Asp Asp Gly Phe Pro Phe Asn
305                 310                 315                 320

Val Leu Gln Asp Val Phe Thr Leu Ser Pro Ser Pro Gln Asp Trp Arg
            325                 330                 335

Asp Thr Leu Phe Tyr Gly Val Phe Thr Ser Gln Trp His Arg Gly Thr
            340                 345                 350

Thr Glu Gly Ser Ala Val Cys Val Phe Thr Met Lys Asp Val Gln Arg
            355                 360                 365

Val Phe Ser Gly Leu Tyr Lys Glu Val Asn Arg Glu Thr Gln Gln Trp
            370                 375                 380

Tyr Thr Val Thr His Pro Val Pro Thr Pro Arg Pro Gly Ala Cys Ile
385                 390                 395                 400

Thr Asn Ser Ala Arg Glu Arg Lys Ile Asn Ser Ser Leu Gln Leu Pro
            405                 410                 415

Asp Arg Val Leu Asn Phe Leu Lys Asp His Phe Leu Met Asp Gly Gln
            420                 425                 430

Val Arg Ser Arg Met Leu Leu Leu Gln Pro Gln Ala Arg Tyr Gln Arg
            435                 440                 445

Val Ala Val His Arg Val Pro Gly Leu His His Thr Tyr Asp Val Leu
450                 455                 460

Phe Leu Gly Thr Gly Asp Gly Arg Leu His Lys Ala Val Ser Val Gly
465                 470                 475                 480

Pro Arg Val His Ile Ile Glu Glu Leu Gln Ile Phe Ser Ser Gly Gln
            485                 490                 495

Pro Val Gln Asn Leu Leu Leu Asp Thr His Arg Gly Leu Leu Tyr Ala
            500                 505                 510

Ala Ser His Ser Gly Val Val Gln Val Pro Met Ala Asn Cys Ser Leu
            515                 520                 525

Tyr Arg Ser Cys Gly Asp Cys Leu Leu Ala Arg Asp Pro Tyr Cys Ala
            530                 535                 540

Trp Ser Gly Ser Ser Cys Lys His Val Ser Leu Tyr Gln Pro Gln Leu
545                 550                 555                 560
```

-continued

```
Ala Thr Arg Pro Trp Ile Gln Asp Ile Glu Gly Ala Ser Ala Lys Asp
            565                 570                 575

Leu Cys Ser Ala Ser Ser Val Val Ser Pro Ser Phe Val Pro Thr Gly
            580                 585                 590

Glu Lys Pro Cys Glu Gln Val Gln Phe Gln Pro Asn Thr Val Asn Thr
            595                 600                 605

Leu Ala Cys Pro Leu Leu Ser Asn Leu Ala Thr Arg Leu Trp Leu Arg
            610                 615                 620

Asn Gly Ala Pro Val Asn Ala Ser Ala Ser Cys His Val Leu Pro Thr
625                 630                 635                 640

Gly Asp Leu Leu Val Gly Thr Gln Gln Leu Gly Glu Phe Gln Cys
                645                 650                 655

Trp Ser Leu Glu Glu Gly Phe Gln Gln Leu Val Ala Ser Tyr Cys Pro
            660                 665                 670

Glu Val Val Glu Asp Gly Val Ala Asp Gln Thr Asp Thr Val Pro Thr
                675                 680                 685

Pro Arg Pro Gly Ala Cys Ile Thr Asn Ser Ala Arg Glu Arg Lys Ile
            690                 695                 700

Asn Ser Ser Leu Gln Leu Pro Asp Arg Val Leu Asn Phe Leu Lys Asp
705                 710                 715                 720

His Phe Leu Met Asp Gly Gln Val Arg Ser Arg Met Leu Leu Gln
                725                 730                 735

Pro Gln Ala Arg Tyr Gln Arg Val Ala Val His Arg Val Pro Gly Leu
            740                 745                 750

His His Thr Tyr Asp Val Leu Phe Leu Gly Thr Gly Asp Gly Arg Leu
                755                 760                 765

His Lys Ala Val Ser Val Gly Pro Arg Val His Ile Ile Glu Glu Leu
770                 775                 780

Gln Ile Phe Ser Ser Gly Gln Pro Val Gln Asn Leu Leu Asp Thr
785                 790                 795                 800

His Arg Gly Leu Leu Tyr Ala Ala Ser His Ser Gly Val Val Gln Val
                805                 810                 815

Pro Met Ala Asn Cys Ser Leu Tyr Arg Ser Cys Gly Asp Cys Leu Leu
            820                 825                 830

Ala Arg Asp Pro Tyr Cys Ala Trp Ser Gly Ser Ser Cys Lys His Val
            835                 840                 845

Ser Leu Tyr Gln Pro Gln Leu Ala Thr Arg Pro Trp Ile Gln Asp Ile
850                 855                 860

Glu Gly Ala Ser Ala Lys Asp Leu Cys Ser Ala Ser Ser Val Val Ser
865                 870                 875                 880

Pro Ser Phe Val Pro Thr Gly Glu Lys Pro Cys Glu Gln Val Gln Phe
                885                 890                 895

Gln Pro Asn Thr Val Asn Thr Leu Ala Cys Pro Leu Leu Ser Asn Leu
            900                 905                 910

Ala Thr Arg Leu Trp Leu Arg Asn Gly Ala Pro Val Asn Ala Ser Ala
            915                 920                 925

Ser Cys His Val Leu Pro Thr Gly Asp Leu Leu Val Gly Thr Gln
930                 935                 940

Gln Leu Gly Glu Phe Gln Cys Trp Ser Leu Glu Glu Gly Phe Gln Gln
945                 950                 955                 960

Leu Val Ala Ser Tyr Cys Pro Glu Val Val Glu Asp Gly Val Ala Asn
                965                 970                 975

Gln Thr Asp Glu Gly Gly Ser Val Pro Val Ile Ile Ser Thr Ser Arg
```

```
                980             985             990
Val Ser Ala Pro Ala Gly Gly Lys Ala Ser Trp Gly Ala Asp Arg Ser
            995                 1000                1005

Tyr Trp Lys Glu Phe Leu Val Met Cys Thr Leu Phe Val Leu Ala Val
        1010                1015                1020

Leu Leu Pro Val Leu Phe Leu Leu Tyr Arg His Arg Asn Ser Met Lys
1025                1030                1035                1040

Val Phe Leu Lys Gln Gly Glu Cys Ala Ser Val His Pro Lys Thr Cys
                1045                1050                1055

Pro Val Val Leu Pro Pro Glu Thr Arg Pro Leu Asn Gly Leu Gly Pro
            1060                1065                1070

Pro Ser Thr Pro Leu Asp His Arg Gly Tyr Gln Ser Pro Arg Arg Thr
        1075                1080                1085

Ala His Leu Val His Asp Pro Gln Ala Arg Cys Leu Lys Arg Ile Gln
    1090                1095                1100
Thr
1105

<210> SEQ ID NO 33
<211> LENGTH: 3399
<212> TYPE: DNA
<213> ORGANISM: homo sapiens

<400> SEQUENCE: 33
atgctgcgca ccgcgatggg cctgaggagc tggctcgccg ccccatgggg cgcgctgccg    60
cctcggccac cgctgctgct gctcctgctg ctgctgctcc tgctgcagcc gccgcctccg   120
acctgggcgc tcagcccccg gatcagcctg cctctgggct ctgaagagcg gccattcctc   180
agattcgaag ctgaacacat ctccaactac acagcccttc tgctgagcag ggatggcagg   240
accctgtacg tgggtgctcg agaggccctc tttgcactca gtagcaacct cagcttcctg   300
ccaggcgggg agtaccagga gctgctttgg ggtgcagacg cagagaagaa acagcagtgc   360
agcttcaagg gcaaggaccc acagcgcgac tgtcaaaact acatcaagat cctcctgccg   420
ctcagcggca gtcacctgtt cacctgtggc acagcagcct cagccccat gtgtacctac     480 atcaacatgg agaacttcac cctggcaagg gacgagaagg ggaatgtcct cctggaagat   540
ggcaagggcc gttgtccctt cgacccgaat tcaagtcca ctgccctggt ggttgatggc    600
gagctctaca ctggaacagt cagcagcttc aagggaatg accggccat ctcgcggagc      660 caaagccttc gccccaccaa gaccgagagc tccctcaact ggctgcaaga cccagctttt   720
gtggcctcag cctacattcc tgagagcctg gcagcttgc aaggcgatga tgacaagatc    780 tacttttct tcagcgagac tggccaggaa tttgagttct tgagaacac cattgtgtcc     840 cgcattgccc gcatctgcaa gggcgatgag ggtggagagc gggtgctaca gcagcgctgg   900
acctccttcc tcaaggccca gctgctgtgc acggcccg acgatggctt cccccttcaac    960 gtgctgcagg atgtcttcac gctgagcccc agccccagg actggcgtga cacccttttc   1020
tatgggtctt tcacttccca gtggcacagg ggaactacag aaggctctgc cgtctgtgtc   1080
ttcacaatga aggatgtgca gagagtcttc agcggcctct acaaggaggt gaaccgtgag   1140
acacagcagt ggtacaccgt gacccaccg gtgcccacac ccggcctgg agcgtgcatc    1200 accaacagtg cccgggaaag gaagatcaac tcatccctgc agctcccaga ccgcgtgctg   1260
aacttcctca aggaccactt cctgatggac gggcaggtcc gaagccgcat gctgctgctg   1320
cagccccagg ctcgctacca gcgcgtggct gtacaccgcg tccctggcct gcaccacacc   1380
```

```
tacgatgtcc tcttcctggg cactggtgac ggccggctcc acaaggcagt gagcgtgggc   1440
ccccgggtgc acatcattga ggagctgcag atcttctcat cgggacagcc cgtgcagaat   1500
ctgctcctgg acacccacag ggggctgctg tatgcggcct cacactcggg cgtagtccag   1560
gtgcccatgg ccaactgcag cctgtacagg agctgtgggg actgcctcct cgcccgggac   1620
ccctactgtg cttggagcgg ctccagctgc aagcacgtca gcctctacca gcctcagctg   1680
gccaccaggc cgtggatcca ggacatcgag ggagccagcg ccaaggacct ttgcagcgcg   1740
tcttcggttg tgtccccgtc ttttgtacca acagggagag agccatgtga gcaagtccag   1800
ttccagccca acacagtgaa cactttggcc tgcccgctcc tctccaacct ggcgacccga   1860
ctctggctac gcaacgggc ccccgtcaat gcctcggcct cctgccacgt gctacccact   1920
ggggacctgc tgctggtggg cacccaacag ctgggggagt tccagtgctg gtcactagag   1980
gagggcttcc agcagctggt agccagctac tgcccagagg tggtggagga cggggtggca   2040
gaccaaacag atacggtgcc cacacccgg cctggagcgt gcatcaccaa cagtgcccgg   2100
gaaaggaaga tcaactcatc cctgcagctc ccagaccgcg tgctgaactt cctcaaggac   2160
cacttcctga tggacgggca ggtccgaagc cgcatgctgc tgctgcagcc ccaggctcgc   2220
taccagcgcg tggctgtaca ccgcgtccct ggcctgcacc acacctacga tgtcctcttc   2280
ctgggcactg gtgacggccg gctccacaag gcagtgagcg tgggccccg ggtgcacatc   2340 attgaggagc tgcagatctt ctcatcggga cagcccgtgc agaatctgct cctggacacc   2400
cacagggggc tgctgtatgc ggcctcacac tcgggcgtag tccaggtgcc catggccaac   2460
tgcagcctgt acaggagctg tggggactgc ctcctcgccc gggaccccta ctgtgcttgg   2520
agcggctcca gctgcaagca cgtcagcctc taccagcctc agctggccac caggccgtgg   2580
atccaggaca tcgagggagc cagcgccaag gacctttgca gcgcgtcttc ggttgtgtcc   2640
ccgtcttttg taccaacagg ggagaagcca tgtgagcaag tccagttcca gcccaacaca   2700
gtgaacactt tggcctgccc gctcctctcc aacctggcga cccgactctg ctacgcaac   2760 ggggcccccg tcaatgcctc ggcctcctgc cacgtgctac ccactgggga cctgctgctg   2820
gtgggcaccc aacagctggg ggagttccag tgctggtcac tagaggaggg cttccagcag   2880
ctggtagcca gctactgccc agaggtggtg gaggacgggg tggcaaacca aacagatgag   2940
ggtggcagtg tacccgtcat tatcagcaca tcgcgtgtga gtgcaccagc tggtggcaag   3000
gccagctggg gtgcagacag gtcctactgg aaggagttcc tggtgatgtg cacgctctt   3060 gtgctggccg tgctgctccc agtttttattc ttgctctacc ggcaccggaa cagcatgaaa   3120
gtcttcctga gcaggggga atgtgccagc gtgcacccca agacctgccc tgtggtgctg   3180
ccccctgaga cccgcccact caacggccta gggcccccta gcaccccgct cgatcaccga   3240
gggtaccagt ccctgtcaga cagccccccg ggggcccgag tcttcactga gtcagagaag   3300
aggccactca gcatccaaga cagcttcgtg gaggtatccc cagtgtgccc ccggccccgg   3360
gtccgccttg gctcggagat ccgtgactct gtggtgtga                          3399
```

<210> SEQ ID NO 34
<211> LENGTH: 1132
<212> TYPE: PRT
<213> ORGANISM: homo sapiens

<400> SEQUENCE: 34

Met Leu Arg Thr Ala Met Gly Leu Arg Ser Trp Leu Ala Ala Pro Trp
1               5                   10                  15

```
Gly Ala Leu Pro Pro Arg Pro Pro Leu Leu Leu Leu Leu Leu Leu
             20                  25                  30

Leu Leu Leu Gln Pro Pro Pro Thr Trp Ala Leu Ser Pro Arg Ile
         35                  40                  45

Ser Leu Pro Leu Gly Ser Glu Glu Arg Pro Phe Leu Arg Phe Glu Ala
     50                  55                  60

Glu His Ile Ser Asn Tyr Thr Ala Leu Leu Ser Arg Asp Gly Arg
 65                  70                  75                  80

Thr Leu Tyr Val Gly Ala Arg Glu Ala Leu Phe Ala Leu Ser Ser Asn
                 85                  90                  95

Leu Ser Phe Leu Pro Gly Gly Glu Tyr Gln Glu Leu Leu Trp Gly Ala
             100                 105                 110

Asp Ala Glu Lys Lys Gln Gln Cys Ser Phe Lys Gly Lys Asp Pro Gln
             115                 120                 125

Arg Asp Cys Gln Asn Tyr Ile Lys Ile Leu Leu Pro Leu Ser Gly Ser
 130                 135                 140

His Leu Phe Thr Cys Gly Thr Ala Ala Phe Ser Pro Met Cys Thr Tyr
145                 150                 155                 160

Ile Asn Met Glu Asn Phe Thr Leu Ala Arg Asp Glu Lys Gly Asn Val
                 165                 170                 175

Leu Leu Glu Asp Gly Lys Gly Arg Cys Pro Phe Asp Pro Asn Phe Lys
             180                 185                 190

Ser Thr Ala Leu Val Val Asp Gly Glu Leu Tyr Thr Gly Thr Val Ser
             195                 200                 205

Ser Phe Gln Gly Asn Asp Pro Ala Ile Ser Arg Ser Gln Ser Leu Arg
 210                 215                 220

Pro Thr Lys Thr Glu Ser Ser Leu Asn Trp Leu Gln Asp Pro Ala Phe
225                 230                 235                 240

Val Ala Ser Ala Tyr Ile Pro Glu Ser Leu Gly Ser Leu Gln Gly Asp
                 245                 250                 255

Asp Asp Lys Ile Tyr Phe Phe Ser Glu Thr Gly Gln Glu Phe Glu
             260                 265                 270

Phe Phe Glu Asn Thr Ile Val Ser Arg Ile Ala Arg Ile Cys Lys Gly
             275                 280                 285

Asp Glu Gly Gly Glu Arg Val Leu Gln Gln Arg Trp Thr Ser Phe Leu
 290                 295                 300

Lys Ala Gln Leu Leu Cys Ser Arg Pro Asp Asp Gly Phe Pro Phe Asn
305                 310                 315                 320

Val Leu Gln Asp Val Phe Thr Leu Ser Pro Ser Pro Gln Asp Trp Arg
                 325                 330                 335

Asp Thr Leu Phe Tyr Gly Val Phe Thr Ser Gln Trp His Arg Gly Thr
             340                 345                 350

Thr Glu Gly Ser Ala Val Cys Val Phe Thr Met Lys Asp Val Gln Arg
             355                 360                 365

Val Phe Ser Gly Leu Tyr Lys Glu Val Asn Arg Glu Thr Gln Gln Trp
 370                 375                 380

Tyr Thr Val Thr His Pro Val Pro Thr Pro Arg Pro Gly Ala Cys Ile
385                 390                 395                 400

Thr Asn Ser Ala Arg Glu Arg Lys Ile Asn Ser Ser Leu Gln Leu Pro
                 405                 410                 415

Asp Arg Val Leu Asn Phe Leu Lys Asp His Phe Leu Met Asp Gly Gln
             420                 425                 430
```

```
Val Arg Ser Arg Met Leu Leu Leu Gln Pro Gln Ala Arg Tyr Gln Arg
            435                 440                 445

Val Ala Val His Arg Val Pro Gly Leu His His Thr Tyr Asp Val Leu
            450                 455                 460

Phe Leu Gly Thr Gly Asp Gly Arg Leu His Lys Ala Val Ser Val Gly
465                 470                 475                 480

Pro Arg Val His Ile Ile Glu Glu Leu Gln Ile Phe Ser Ser Gly Gln
                485                 490                 495

Pro Val Gln Asn Leu Leu Leu Asp Thr His Arg Gly Leu Leu Tyr Ala
                500                 505                 510

Ala Ser His Ser Gly Val Val Gln Val Pro Met Ala Asn Cys Ser Leu
            515                 520                 525

Tyr Arg Ser Cys Gly Asp Cys Leu Leu Ala Arg Asp Pro Tyr Cys Ala
            530                 535                 540

Trp Ser Gly Ser Ser Cys Lys His Val Ser Leu Tyr Gln Pro Gln Leu
545                 550                 555                 560

Ala Thr Arg Pro Trp Ile Gln Asp Ile Glu Gly Ala Ser Ala Lys Asp
                565                 570                 575

Leu Cys Ser Ala Ser Ser Val Val Ser Pro Ser Phe Val Pro Thr Gly
            580                 585                 590

Glu Lys Pro Cys Glu Gln Val Gln Phe Gln Pro Asn Thr Val Asn Thr
            595                 600                 605

Leu Ala Cys Pro Leu Leu Ser Asn Leu Ala Thr Arg Leu Trp Leu Arg
            610                 615                 620

Asn Gly Ala Pro Val Asn Ala Ser Ala Ser Cys His Val Leu Pro Thr
625                 630                 635                 640

Gly Asp Leu Leu Leu Val Gly Thr Gln Gln Leu Gly Glu Phe Gln Cys
                645                 650                 655

Trp Ser Leu Glu Glu Gly Phe Gln Gln Leu Val Ala Ser Tyr Cys Pro
                660                 665                 670

Glu Val Val Glu Asp Gly Val Ala Asp Gln Thr Asp Thr Val Pro Thr
            675                 680                 685

Pro Arg Pro Gly Ala Cys Ile Thr Asn Ser Ala Arg Glu Arg Lys Ile
            690                 695                 700

Asn Ser Ser Leu Gln Leu Pro Asp Arg Val Leu Asn Phe Leu Lys Asp
705                 710                 715                 720

His Phe Leu Met Asp Gly Gln Val Arg Ser Arg Met Leu Leu Leu Gln
                725                 730                 735

Pro Gln Ala Arg Tyr Gln Arg Val Ala Val His Arg Val Pro Gly Leu
            740                 745                 750

His His Thr Tyr Asp Val Leu Phe Leu Gly Thr Gly Asp Gly Arg Leu
            755                 760                 765

His Lys Ala Val Ser Val Gly Pro Arg Val His Ile Ile Glu Glu Leu
            770                 775                 780

Gln Ile Phe Ser Ser Gly Gln Pro Val Gln Asn Leu Leu Leu Asp Thr
785                 790                 795                 800

His Arg Gly Leu Leu Tyr Ala Ala Ser His Ser Gly Val Val Gln Val
                805                 810                 815

Pro Met Ala Asn Cys Ser Leu Tyr Arg Ser Cys Gly Asp Cys Leu Leu
            820                 825                 830

Ala Arg Asp Pro Tyr Cys Ala Trp Ser Gly Ser Ser Cys Lys His Val
            835                 840                 845

Ser Leu Tyr Gln Pro Gln Leu Ala Thr Arg Pro Trp Ile Gln Asp Ile
```

-continued

```
              850             855            860
Glu Gly Ala Ser Ala Lys Asp Leu Cys Ser Ala Ser Ser Val Val Ser
865                 870                 875                 880

Pro Ser Phe Val Pro Thr Gly Glu Lys Pro Cys Glu Gln Val Gln Phe
                885                 890                 895

Gln Pro Asn Thr Val Asn Thr Leu Ala Cys Pro Leu Leu Ser Asn Leu
            900                 905                 910

Ala Thr Arg Leu Trp Leu Arg Asn Gly Ala Pro Val Asn Ala Ser Ala
        915                 920                 925

Ser Cys His Val Leu Pro Thr Gly Asp Leu Leu Leu Val Gly Thr Gln
    930                 935                 940

Gln Leu Gly Glu Phe Gln Cys Trp Ser Leu Glu Glu Gly Phe Gln Gln
945                 950                 955                 960

Leu Val Ala Ser Tyr Cys Pro Glu Val Val Glu Asp Gly Val Ala Asn
                965                 970                 975

Gln Thr Asp Glu Gly Gly Ser Val Pro Val Ile Ile Ser Thr Ser Arg
            980                 985                 990

Val Ser Ala Pro Ala Gly Gly Lys Ala Ser Trp Gly Ala Asp Arg Ser
        995                 1000                1005

Tyr Trp Lys Glu Phe Leu Val Met Cys Thr Leu Phe Val Leu Ala Val
    1010                1015                1020

Leu Leu Pro Val Leu Phe Leu Leu Tyr Arg His Arg Asn Ser Met Lys
1025                1030                1035                1040

Val Phe Leu Lys Gln Gly Glu Cys Ala Ser Val His Pro Lys Thr Cys
                1045                1050                1055

Pro Val Val Leu Pro Pro Glu Thr Arg Pro Leu Asn Gly Leu Gly Pro
            1060                1065                1070

Pro Ser Thr Pro Leu Asp His Arg Gly Tyr Gln Ser Leu Ser Asp Ser
        1075                1080                1085

Pro Pro Gly Ala Arg Val Phe Thr Glu Ser Glu Lys Arg Pro Leu Ser
    1090                1095                1100

Ile Gln Asp Ser Phe Val Glu Val Ser Pro Val Cys Pro Arg Pro Arg
1105                1110                1115                1120

Val Arg Leu Gly Ser Glu Ile Arg Asp Ser Val Val
                1125                1130
```

<210> SEQ ID NO 35
<211> LENGTH: 3366
<212> TYPE: DNA
<213> ORGANISM: homo sapiens

<400> SEQUENCE: 35

```
catagcaggc atggccttgc tcactgagca ttcactacat gccagtgttg cccgtggctt    60
tatatgtact ctctccagcc acccatgaag tgctgttcat agcactccgt cctagatgaa   120
gaagctgagg ttcagagtga ttgtgtggct tgctaaaagt ccacaaaata tggaaggtag   180
tgaattcttc tgacagaaga acctgtgtgc tcaaccactg gattctacca cttccaggag   240
caagaaaaac aagaggccgg tagcggggaa atggtttggg ggaacggaga tgaagccatt   300 tatttcatc tgttgccaga ccctgggtaa aagctgccag tgagttttga aggcagtgta    360
agtgctgacc cggggtggat gccctctgct gcagaaggcg ctgccccaag gaagctccca   420
gccctgagga cttggcagcc attggctgat ttgaaagaat acacagggtg tgccagctgg   480
tgtcgcttcc tcttcaacat gtactgatgc tgcagctgag ctgctgccca gcccctgggg   540
```

-continued

| | |
|---|---|
| agaagacatc agcagcatgc ccagccaggg cagggtggag agctgcagct gcaggtccgg | 600 |
| aggcggggc ccccggggcg actcgggggc ggaccgcggg gcggagctgc cgcccgtgag | 660 |
| tccggccgag ccacctgagc ccgagccgcg ggacaccgtc gctcctgctc tccgaatgct | 720 |
| gcgcaccgcg atgggcctga ggagctggct cgccgcccca tggggcgcgc tgccgcctcg | 780 |
| gccaccgctg ctgctgctcc tgctgctgct gctcctgctg cagccgccgc ctccgacctg | 840 |
| ggcgctcagc ccccggatca gcctgcctct gggctctgaa gagcggccat tcctcagatt | 900 |
| cgaagctgaa cacatctcca actacacagc ccttctgctg agcagggatg caggaccct | 960 |
| gtacgtgggt gctcgagagg ccctctttgc actcagtagc aacctcagct tcctgccagg | 1020 |
| cggggagtac caggagctgc tttggggtgc agacgcagag aagaaacagc agtgcagctt | 1080 |
| caagggcaag gacccacagc gcgactgtca aaactacatc aagatcctcc tgccgctcag | 1140 |
| cggcagtcac ctgttcacct gtggcacagc agccttcagc ccatgtgta cctacatcaa | 1200 |
| catggagaac ttcaccctgg caagggacga aagggaat gtcctcctgg aagatggcaa | 1260 |
| gggccgttgt cccttcgacc cgaatttcaa gtccactgcc ctggtggttg atggcgagct | 1320 |
| ctacactgga acagtcagca gcttccaagg gaatgacccg gccatctcgc ggagccaaag | 1380 |
| ccttcgcccc accaagaccg agagctccct caactggctg caagacccag cttttgtggc | 1440 |
| ctcagcctac attcctgaga gcctgggcag cttgcaaggc gatgatgaca agatctactt | 1500 |
| tttcttcagc gagactggcc aggaatttga gttctttgag aacaccattg tgtcccgcat | 1560 |
| tgcccgcatc tgcaagggcg atgagggtgg agagcgggtg ctacagcagc gctggacctc | 1620 |
| cttcctcaag gcccagctgc tgtgctcacg gcccgacgat ggcttcccct tcaacgtgct | 1680 |
| gcaggatgtc ttcacgctga gccccagccc ccaggactgg cgtgacaccc ttttctatgg | 1740 |
| ggtcttcact tcccagtggc acaggggaac tacagaaggc tctgccgtct gtgtcttcac | 1800 |
| aatgaaggat gtgcagagag tcttcagcgg cctctacaag gaggtgaacc gtgagacaca | 1860 |
| gcagtggtac accgtgaccc acccggtgcc cacaccccgg cctggagcgt gcatcaccaa | 1920 |
| cagtgcccgg gaaaggaaga tcaactcatc cctgcagctc ccagaccgcg tgctgaactt | 1980 |
| cctcaaggac cacttcctga tggacgggca ggtccgaagc cgcatgctgc tgctgcagcc | 2040 |
| ccaggctcgc taccagcgcg tggctgtaca ccgcgtccct ggcctgcacc acacctacga | 2100 |
| tgtcctcttc ctgggcactg gtgacggccg gctccacaag gcagtgagcg tgggcccccg | 2160 |
| ggtgcacatc attgaggagc tgcagatctt ctcatcggga cagcccgtgc agaatctgct | 2220 |
| cctgacacc cacaggggc tgctgtatgc ggcctcacac tcgggcgtag tccaggtgcc | 2280 |
| catggccaac tgcagcctgt acaggagctg tggggactgc ctcctcgccc ggaccccta | 2340 |
| ctgtgcttgg agcggctcca gctgcaagca cgtcagcctc taccagcctc agctggccac | 2400 |
| caggccgtgg atccaggaca tcgagggagc cagcgccaag gacctttgca gcgcgtcttc | 2460 |
| ggttgtgtcc ccgtcttttg taccaacagg ggagaagcca tgtgagcaag tccagttcca | 2520 |
| gcccaacaca gtgaacactt tggcctgccc gctcctctcc aacctggcga cccgactctg | 2580 |
| gctacgcaac gggccccccg tcaatgcctc ggcctcctgc cacgtgctac ccactgggga | 2640 |
| cctgctgctg gtgggcaccc aacagctggg ggagttccag tgctggtcac tagaggaggg | 2700 |
| cttccagcag ctggtagcca gctactgcca agaggtggtg gaggacgggg tggcagacca | 2760 |
| aacagatgag ggtggcagtg tacccgtcat tatcagcaca tcgcgtgtga gtgcaccagc | 2820 |
| tggtggcaag gccagctggg gtgcagacag gtcctactgg aaggagttcc tggtgatgtg | 2880 |
| cacgctcttt gtgctggccg tgctgctccc agttttattc ttgctctacc ggcaccggaa | 2940 |

```
cagcatgaaa gtcttcctga agcaggggga atgtgccagc gtgcacccca agacctgccc    3000
tgtggtgctg cccoctgaga cccgcccact caacggccta gggcccccta gcacccogct    3060 cgatcaccga gggtaccagt ccctgtcaga cagccccccg ggggcccgag tcttcactga    3120
gtcagagaag aggccactca gcatccaaga cagcttcgtg gaggtatccc cagtgtgccc    3180
ccggccccgg gtccgccttg gctcggagat ccgtgactct gtggtgtgag agctgacttc    3240
cagaggacgc tgccctggct tcaggggctg tgaatgctcg gagagggtca actggacctc    3300
ccctccgctc tgctcttcgt ggaacacgac cgtggtgccg cagcaacaga tggaaggcct    3360
cctggc                                                               3366
```

HUMAN SEMAPHORIN PROTEINS AND POLYNUCLEOTIDES ENCODING THE SAME

The present application claims the benefit of U.S. Provisional Application No. 60/241,194 which was filed on Oct. 17, 2000 and is herein incorporated by reference in its entirety.

1. INTRODUCTION

The present invention relates to the discovery, identification, and characterization of novel human polynucleotides encoding proteins of novel mammalian semaphorin proteins. The invention encompasses the described polynucleotides, host cell expression systems, the encoded proteins, fusion proteins, polypeptides and peptides, antibodies to the encoded proteins and peptides, and genetically engineered animals that either lack or over express the disclosed genes, antagonists and agonists of the proteins, and other compounds that modulate the expression or activity of the proteins encoded by the disclosed genes that can be used for diagnosis, drug screening, clinical trial monitoring, the treatment of diseases and disorders, and cosmetic or nutriceutical applications.

2. BACKGROUND OF THE INVENTION

Semaphorins are secreted proteins that have been implicated in a number of biological processes and anomalies such as neural development, paralysis, and axon guidance.

3. SUMMARY OF THE INVENTION

The present invention relates to the discovery, identification, and characterization of nucleotides that encode novel human proteins, and the corresponding amino acid sequences of these proteins. The novel human proteins (NHPs) described for the first time herein share structural similarity with animal semaphorin proteins and other animal proteins including, but not limited to, human secreted proteins. The novel human nucleic acid sequence described herein encode alternative proteins/open reading frames (ORFs) of 767, 1047, 1062, 838, 1150, 863, 1158, 890, 1185, 714, 994, 1009, 785, 1097, 810, 1105, and 1132 amino acids in length (see SEQ ID NOS:2, 4, 6, 8, 10, 12, 14, 16, 18, 20, 22, 24, 26, 28, 30, 32, and 34).

The invention also encompasses agonists and antagonists of the described NHPs, including small molecules, large molecules, mutant NHPs, or portions thereof, that compete with native NHP, peptides, and antibodies, as well as nucleotide sequences that can be used to inhibit the expression of the described NHPs (e.g., antisense and ribozyme molecules, and open reading frame or regulatory sequence replacement constructs) or to enhance the expression of the described NHPs (e.g., expression constructs that place the described polynucleotide under the control of a strong promoter system), and transgenic animals that express a NHP sequence, or "knock-outs" (which can be conditional) that do not express a functional NHP. Knock-out mice can be produced in several ways, one of which involves the use of mouse embryonic stem cells ("ES cells") lines that contain gene trap mutations in a murine homolog of at least one of the described NHPs. When the unique NHP sequences described in SEQ ID NOS:1–35 are "knocked-out" they provide a method of identifying phenotypic expression of the particular gene as well as a method of assigning function to previously unknown genes. In addition, animals in which the unique NHP sequences described in SEQ ID NOS:1–35 are "knocked-out" provide a unique source in which to elicit antibodies to homologous and orthologous proteins which would have been previously viewed by the immune system as "self" and therefore would have failed to elicit significant antibody responses. To these ends, gene trapped knockout ES cells have been generated in murine homologs of the described NHPs and knock-out mice have been generated using gene trap mutation of the mouse homolog of the gene described by unique NHP sequences described in SEQ ID NOS:1–35 using methods, such as those described in, U.S. Pat. Nos. 6,136,566; 6,139,833 and 6,207,371 and U.S. patent application Ser. No. 08/728,963, each of which are hereby incorporated herein by reference in their entirety and for example, "Mouse Mutagenesis", 1998, Zambrowicz et al., eds., Lexicon Press, The Woodlands, Tex., and periodic updates thereof, which are herein incorporated by reference. Homozygous NHP gene deficient mice demonstrated a decrease in body-weight as compared to control wild-type mice, however, no additional phenotypic alterations were observed.

Additionally, the unique NHP sequences described in SEQ ID NOS:1–35 are useful for the identification of protein coding sequence and mapping a unique gene to a particular chromosome (the gene encoding the described NHPs is apparently encoded on human chromosome 15, see GENBANK accession no. AC058820). These sequences identify actual, biologically relevant, exon splice junctions as opposed to those that might have been predicted bioinformatically from genomic sequence alone. The sequences of the present invention are also useful as additional DNA markers for restriction fragment length polymorphism (RFLP) analysis, and in forensic biology.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of the NHP ORFs encoding the described NHP amino acid sequences. SEQ ID NO: 35 describes a NHP ORF and flanking regions.

5. DETAILED DESCRIPTION OF THE INVENTION

The NHPs described for the first time herein are novel proteins that are expressed in, inter alia, human fetal brain, brain, pituitary, spinal cord, spleen, lymph node, bone marrow, lung, kidney, fetal liver, prostate, adrenal gland, pancreas, salivary gland, stomach, small intestine, colon, placenta, skin, bladder, cervix, pericardium, ovary, fetal lung, fetal kidney, and fetal lung. The present invention encompasses the nucleotides presented in the Sequence Listing, host cells expressing such nucleotides, the expression products of such nucleotides, and: (a) nucleotides that encode mammalian homologs of the described gene, including the specifically described NHP, and related NHP products; (b) nucleotides that encode one or more portions of a NHP corresponding to a NHP functional domain(s), and the polypeptide products specified by such nucleotide sequences, including but not limited to the novel regions of any active domain(s); (c) isolated nucleotides that encode mutant versions, engineered or naturally occurring, of the described NHP in which all or a part of at least one domain is deleted or altered, and the polypeptide products specified by such nucleotide sequences, including but not limited to soluble proteins and peptides in which all or a portion of the signal sequence is deleted; (d) nucleotides that encode chimeric fusion proteins containing all or a portion of a coding region of a NHP, or one of its domains (e.g., a receptor or ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing. As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & Sons, Inc., New York, at p. 2.10.3) and encodes a functionally equivalent expression product. Additionally contemplated are any nucleotide sequences that hybridize to the complement of the DNA sequence that encode and express an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458 herein incorporated by reference). The invention also includes degenerate nucleic acid variants of the disclosed NHP polynucleotide sequence.

Additionally contemplated are polynucleotides encoding NHP ORFs, or their functional equivalents, encoded by polynucleotide sequences that are about 99, 95, 90, or about 85 percent similar or identical to corresponding regions of the nucleotide sequences of the Sequence Listing (as measured by BLAST sequence comparison analysis using, for example, the GCG sequence analysis package using standard default settings).

The invention also includes nucleic acid molecules, preferably DNA molecules, that hybridize to, and are therefore the complements of, the described NHP gene nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1–35 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–35, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–35 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–35.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–35 provides detailed information about transcriptional changes involved in a specific pathway, potentially leading to the identification of novel components or gene functions that manifest themselves as novel phenotypes.

Probes consisting of sequences first disclosed in SEQ ID NOS:1–35 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–35 can be utilized in microarrays or other assay formats, to screen collections of genetic material from patients who have a particular medical condition. These investigations can also be carried out using the sequences first disclosed in SEQ ID NOS:1–35 in silico and by comparing previously collected genetic databases and the disclosed sequences using computer software known to those in the art.

Thus the sequences first disclosed in SEQ ID NOS:1–35 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–35. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relative to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules useful, for example, in NHP gene regulation (for and/or as antisense primers in amplification reactions of NHP gene nucleic acid sequences). With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or any combination or analog thereof.

In yet another embodiment, the antisense oligonucleotide is an a-anomeric oligonucleotide. An a-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Spring Harbor Press, NY; and Ausubel et al., 1989, Current Protocols in Molecular Biology, Green Publishing Associates and Wiley Interscience, NY.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

For example, the present sequences can be used in restriction fragment length polymorphism (RFLP) analysis to identify specific individuals. In this technique, an individual's genomic DNA is digested with one or more restriction enzymes, and probed on a Southern blot to yield unique bands for identification (as generally described in U.S. Pat. No. 5,272,057, incorporated herein by reference). In addition, the sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). Actual base sequence information can be used for identification as an accurate alternative to patterns formed by restriction enzyme generated fragments.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from human or non-human cell lines or tissue known or suspected to express an allele of a NHP gene. The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene, such as, for example, testis tissue). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP sequence can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal sequence. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, paralysis or palsy, nerve damage or degeneration, an inflammatory disorder, vision disorders, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue can be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor.) Additionally, screening can be accomplished by screening with labeled NHP fusion proteins, such as, for example, alkaline phosphatase-NHP or NHP-alkaline phosphatase fusion proteins. In cases where a NHP mutation results in an expression product with altered function (e.g., as a result of a missense or a frameshift mutation), polyclonal antibodies to NHP are likely to cross-react with a corresponding mutant NHP expression product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP sequence under the control of an exogenously introduced regulatory element (i.e., gene activation). As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, regulatable, viral (particularly retroviral LTR promoters) the early or late promoters of SV40 adenovirus, the lac system, the trp system, the TAC system, the TRC system, the tet system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of a NHP, as well as compounds or nucleotide constructs that inhibit expression of a NHP sequence (transcription factor inhibitors, antisense and ribozyme molecules, or open reading frame sequence or regulatory sequence replacement constructs), or promote the expression of a NHP (e.g., expression constructs in which NHP coding sequences are operatively associated with expression control elements such as promoters, promoter/enhancers, etc.).

The NHP or NHP peptides, NHP fusion proteins, NHP nucleotide sequences, antibodies, antagonists and agonists can be useful for the detection of mutant NHPs or inappropriately expressed NHPs for the diagnosis of disease. The NHP or NHP peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals may offer an advantage in that such systems allow not only for the identification of compounds that bind to the endogenous receptor for a NHP, but can also identify compounds that trigger NHP-mediated activities or pathways.

Finally, the NHP products can be used as therapeutics. For example, soluble derivatives such as a mature NHP, or NHP peptides/domains corresponding to the NHP, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP receptor. Soluble NHP can also be modified by proteolytic cleavage to active peptide products (e.g., any novel peptide sequence initiating at any one of the amino acids presented in the Sequence Listing and ending at any downstream amino acid). Such products or peptides can be further subject to modification such as the construction of NHP fusion proteins and/or can be derivatized by being combined with pharmaceutically acceptable agents such as, but not limited to, polyethylene glycol (PEG).

Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding a functional NHP, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences and corresponding deduced amino acid sequences of the described NHPs are presented in the Sequence Listing. The NHP nucleotides were obtained by aligning cDNAs from bone marrow, lymph node, kidney, thymus, trachea, fetal kidney, fetal brain, testis, kidney, placenta, thymus, pituitary, and fetal mRNAs (Edge Biosystems, Gaithersburg, Md., Clontech, Palo Alto, Calif.) and human genomic DNA sequence.

Several polymorphisms were identified including a C/T polymorphism at the nucleotide position represented by, for example, position 1425 of SEQ ID NOS: 1–9 (which results in a silent mutation in the amino acid sequence) and a C/T polymorphism at nucleotide position 1266 of SEQ ID NOS: 12–20 results in another silent mutation in the amino acid sequence. Additional silent mutations result from a G/A polymorphisms at the nucleotide position represented by, for example, position 2502 of SEQ ID NOS: 6 and 8; position 3387 of SEQ ID NOS: 7 and 9; position 2343 of SEQ ID NO:17; and position 3228 of SEQ ID NOS: 18 and 20. The present invention contemplates sequences incorporating any of the above polymorphisms, and any and all combinations and permutations thereof.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458 which are herein incorporated by reference in their entirety.

NHP gene products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees may be used to generate NHP transgenic animals.

Any technique known in the art may be used to introduce a NHP transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the NHP transgene in all their cells, as well as animals which carry the transgene in some, but not all their cells, i.e., mosaic animals or somatic cell transgenic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al., 1992, Proc. Natl. Acad. Sci. USA 89:6232–6236. The regulatory sequences required for such a cell-type specific activation will depend upon the particular cell type of interest, and will be apparent to those of skill in the art.

When it is desired that a NHP transgene be integrated into the chromosomal site of the endogenous NHP gene, gene targeting is preferred. Briefly, when such a technique is to be utilized, vectors containing some nucleotide sequences homologous to the endogenous NHP gene are designed for the purpose of integrating, via homologous recombination with chromosomal sequences, into and disrupting the function of the nucleotide sequence of the endogenous NHP gene (i.e., "knockout" animals).

The transgene can also be selectively introduced into a particular cell type, thus inactivating the endogenous NHP gene in only that cell type, by following, for example, the teaching of Gu et al., 1994, Science, 265:103–106. The regulatory sequences required for such a cell-type specific inactivation will depend upon the particular cell type of interest, and will be apparent to those of skill in the art.

Once transgenic animals have been generated, the expression of the recombinant NHP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of NHP gene-expressing tissue, may also be evaluated immunocytochemically using antibodies specific for the NHP transgene product.

5.2 NHPS and NHP Polypeptides

The described NHPs, NHP polypeptides, NHP peptide fragments, mutated, truncated, or deleted forms of a NHP, and/or NHP fusion proteins can be prepared for a variety of uses. These uses include but are not limited to, as secreted therapeutics, the generation of antibodies, as reagents in diagnostic assays, the identification of other cellular gene products related to a NHP, as reagents in assays for screening for compounds that can be used as pharmaceutical reagents useful in the therapeutic treatment of mental, biological, or medical disorders and diseases.

The Sequence Listing discloses the amino acid sequences encoded by the described NHP sequences. Bioinformatics analysis reveals that the NHPs are similar to, for example, semaphorins. The NHPs display initiator methionines in DNA sequence contexts consistent with translation initiation sites, and incorporate hydrophobic sequences similar to those found in membrane and secreted proteins.

The NHP amino acid sequences of the invention include the amino acid sequences presented in the Sequence Listing as well as analogues and derivatives thereof. Further, corresponding NHP homologues from other species are encompassed by the invention. In fact, any NHP product encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4–1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHP encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent expression product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, the NHP peptide or polypeptide is thought to be a soluble or secreted molecule, the peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., *Saccharomyces, Pichia*) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5 K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target expression product can be released from the GST moiety.

In an insect system, *Autographa californica* nuclear polyhedrosis virus (AcNPV) is used as a vector to express foreign polynucleotide sequences. The virus grows in *Spodoptera frugiperda* cells. A NHP coding sequence can be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J. Virol. 46: 584; Smith, U.S. Pat. No. 4,215,051).

In mammalian host cells, a number of viral-based expression systems can be utilized. In cases where an adenovirus is used as an expression vector, the NHP nucleotide sequence of interest may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter et al., 1987, Methods in Enzymol. 153:516–544).

In addition, a host cell strain may be chosen that modulates the expression of the inserted sequences, or modifies and processes the expression product in the specific fashion desired. Such modifications (e.g., glycosylation) and processing (e.g., cleavage) of protein products may be important for the function of the protein. Different host cells have characteristic and specific mechanisms for the post-translational processing and modification of proteins and expression products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the expression product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes, which can be employed in $tk^-$, $hgprt^-$ or $aprt^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the sequence of interest is subcloned into a vaccinia recombination plasmid such that the sequence's open reading frame is translationally fused to an amino-terminal tag consisting of six histidine residues. Extracts from cells infected with recombinant vaccinia virus are loaded onto $Ni^{2+}$.nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in "Liposomes:A Practical Approach", New, R.R.C., ed., Oxford University Press, New York and in U.S. Pat. Nos. 4,594,595, 5,459,127, 5,948,767 and 6,110,490 and their respective disclosures which are herein incorporated by reference in their entirety. Additionally embodied are novel protein constructs engineered in such a way that they facilitate transport of the NHP to the target site or desired organ, where they cross the cell membrane and/or the nucleus where the NHP can exert its functional activity. This goal may be achieved by coupling of the NHP to a cytokine or other ligand that provides targeting specificity, and/or to a protein transducing domain (see generally U.S. applications Ser. No. 60/111,701 and 60/056,713, both of which are herein incorporated by reference, for examples of such transducing sequences) to facilitate passage across cellular membranes and can optionally be engineered to include nuclear localization.

5.3 Antibodies TO NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP expression product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, an NHP peptide (e.g., one corresponding to a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, chitosan, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diphtheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used (see U.S. Pat. Nos. 6,075,181 and 5,877,397 both of which are herein incorporated by reference in their entirety). A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety. Also encompassed by the present invention is the use of fully humanized monoclonal antibodies as described in U.S. Pat. No. 6,150,584 and respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP expression products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or Fab fragments of such anti-idiotypes can be used in therapeutic regimens involving a NHP signaling pathway.

Additionally given the high degree of relatedness of mammalian NHPs, the presently described knock-out mice (having never seen NHP, and thus never been tolerized to NHP) have a unique utility, as they can be advantageously applied to the generation of antibodies against the disclosed mammalian NHP (i.e., NHP will be immunogenic in NHP knock-out animals). To these ends, gene trapped knockout ES cells have been generated in murine homologs of the described NHPs and knock-out mice have been generated using gene trap mutation of the mouse homolog of the gene described by unique NHP sequences described in SEQ ID NOS:1–35 using methods, such as those described in, U.S. Pat. Nos. 6,136,566; 6,139,833 and 6,207,371 and U.S. patent application Ser. No. 08/728,963, each of which are hereby incorporated herein by reference in their entirety and for example, "Mouse Mutagenesis", 1998, Zambrowicz et al., eds., Lexicon Press, The Woodlands, Tex., and periodic updates thereof, which are herein incorporated by reference. Homozygous NHP gene deficient mice demonstrated a decrease in body-weight as compared to control wild-type mice, however, no additional phenotypic alterations were observed.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule comprising a nucleotide sequence encoding the amino acid sequence drawn from the group consisting of SEQ ID NO: 16.

2. An isolated cDNA molecule comprising the nucleotide sequence of SEQ ID NO: 15.

3. An isolated cDNA molecule comprising a nucleotide sequence that:

(a) encodes the amino acid sequence of SEQ ID NO: 16, and (b) hybridizes to a nucleotide sequence that is the complement of SEQ ID NO: 15.

4. A recombinant expression vector comprising a nucleotide sequence encoding the amino acid sequence of SEQ ID NO: 16.

5. The isolated nucleic acid of claim 1, wherein said nucleotide sequence is that of SEQ ID NO: 15.

6. The recombinant expression vector of claim 4, wherein said vector comprises the nucleotide sequence of SEQ ID NO: 15.

7. A cultured or isolated cell comprising the vector of claim 4.

8. The host cell of claim 7, wherein the nucleotide sequence is that of SEQ ID NO: 15.

* * * * *